(12) United States Patent
Grainger et al.

(10) Patent No.: US 6,262,079 B1
(45) Date of Patent: *Jul. 17, 2001

(54) PREVENTION AND TREATMENT OF CARDIOVASCULAR PATHOLOGIES

(75) Inventors: David J. Grainger; James C. Metcalfe, both of Cambridge (GB); Lawrence L. Kunz, Redmond; Robert W. Schroff, Edmonds, both of WA (US); Peter L. Weissberg, Cambridge (GB)

(73) Assignee: NeoRx Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/306,606

(22) Filed: May 6, 1999

Related U.S. Application Data

(60) Continuation of application No. 09/082,643, filed on May 21, 1998, which is a division of application No. 08/486,334, filed on Jun. 7, 1995, now Pat. No. 5,770,609, which is a continuation-in-part of application No. 08/242,161, filed on May 12, 1994, now Pat. No. 5,847,007, which is a continuation-in-part of application No. 08/061,714, filed on May 13, 1993, now abandoned, and a continuation-in-part of application No. 08/241,844, filed on May 12, 1994, now abandoned, which is a continuation-in-part of application No. 08/062,451, filed on May 13, 1993, now abandoned, which is a continuation-in-part of application No. 08/011,669, filed on Jan. 28, 1993, now abandoned, which is a continuation-in-part of application No. PCT/US92/08220, filed on Sep. 25, 1992.

(51) Int. Cl.$^7$ .................. A61K 31/445; A61K 31/40; A61K 31/38; A61K 31/135

(52) U.S. Cl. .................. 514/319; 514/324; 514/422; 514/428; 514/444; 514/448; 514/451

(58) Field of Search .................. 514/319, 324, 514/422, 428, 444, 448, 651

(56) References Cited

U.S. PATENT DOCUMENTS

| | | | |
|---|---|---|---|
| Re. 32,944 | 6/1989 | Harita et al. | 562/455 |
| 2,914,563 | 11/1959 | Allen et al. | 260/570 |
| 3,010,965 | 11/1961 | Elpern | 260/293 |

(List continued on next page.)

FOREIGN PATENT DOCUMENTS

| | | | |
|---|---|---|---|
| 4401554 | 8/1994 | (DE) | A61K/31/135 |
| 4320896 | 1/1995 | (DE) | A61K/31/40 |
| 4320898 | 1/1995 | (DE) . | |

(List continued on next page.)

OTHER PUBLICATIONS

Gulino, A., et al., "Heterogeneity of Binding Sites for Tamoxifen and Tamoxifen Derivatives in Estrogen Target and Nontarget Fetal Organs of Guinea Pig", *Cancer Research*, 42, 1913–1921 (1982).

Gylling, H., et al., "Tamoxifen Decreases Serum Cholesterol by Inhibiting Cholesterol Synthesis", *Atherosclerosis*, 96, 245–247 (1992).

Hehrlein, C., et al., "Low–Dose Radiative Endovascular Stents Prevent Smooth Muscle Cell Proliferation and Neointimal Hyperplasia in Rabbits", *Circulation*, 92, 1570–1575 (1995).

Jordan, V.C., "Long–Term Tamoxifen Therapy to Control or to Prevent Breast Cancer: Laboratory Concept to Clinical Trials", *Hormones, Cell Biology and Cancer: Perspectives and Potentials;* Alan R. Liss, Inc., 105–123 (1988).

Lambert, C.R., et al., "Local Drug Delivery Catheters: Functional Comparison of Porous and Microporous Designs", *Coronary Artery Disease*, 4, 469–475 (1993).

Ribeiro, G., et al., "Adjuvant Tamoxifen for Male Breast Cancer (MBC)", *Br. J. Cancer*, 65, 252–254 (1992).

(List continued on next page.)

*Primary Examiner*—Raymond Henley, III
(74) *Attorney, Agent, or Firm*—Schwegman, Lundberg, Woessner & Kluth, P.A.

(57) ABSTRACT

A method for treating or preventing cardiovascular pathologies by administering a compound of the formula (I):

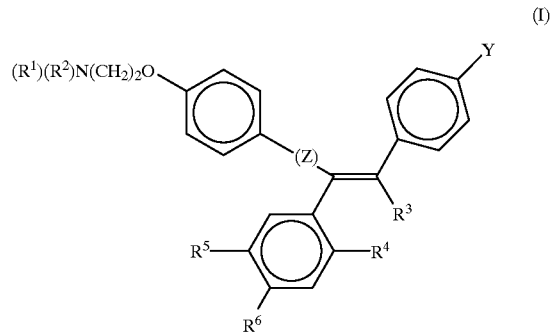

wherein Z is C=O or a covalent bond; Y is H or $O(C_1–C_4)$ alkyl, $R^1$ and $R^2$ are individually $(C_1–C_4)$ allyl or together with N are a saturated heterocyclic group, $R^3$ is ethyl or chloroethyl, $R^4$ is H or together with $R^3$ is —$CH_2$—$CH_2$— or —S—, $R^5$ is I, $O(C_1–C_4)$ alkyl or H and $R^6$ is I, $O(C_1–C_4)$ alkyl or H with the proviso that when $R^4$ $R^5$, and $R^6$ are H, $R^3$ is not ethyl; or a pharmaceutically acceptable salt thereof, effective to activate or stimulate production of TGF-beta to treat and/or prevent conditions such as atherosclerosis, thrombosis, myocardial infarction, and stroke is provided. Useful compounds include idoxifene and salts thereof. Further provided is a method for identifying a compound that is a TGF-beta activator or production stimulator is provided. Another embodiment of the invention is an assay or kit to determine TGF-beta in vitro. Also provided is a therapeutic method comprising inhibiting smooth muscle cell proliferation associated with procedural vascular trauma employing the administration of tamoxifen or structural analogs thereof, including compounds of formula (I).

23 Claims, 2 Drawing Sheets

U.S. PATENT DOCUMENTS

| | | | |
|---|---|---|---|
| 3,168,565 | 2/1965 | Palopoli et al. | 260/570.7 |
| 3,288,806 | 11/1966 | DeWald et al. | 260/326.5 |
| 3,634,517 | 1/1972 | Palopoli et al. | 260/590 |
| 3,940,422 | 2/1976 | Harita et al. | 260/340 |
| 4,070,484 | 1/1978 | Harita et al. | 424/319 |
| 4,093,709 | 6/1978 | Choi et al. | 424/19 |
| 4,133,814 | 1/1979 | Jones et al. | 260/326 |
| 4,230,862 | 10/1980 | Suarez et al. | 546/237 |
| 4,235,988 | 11/1980 | Fildes et al. | 528/79 |
| 4,239,778 | 12/1980 | Venton et al. | 424/305 |
| 4,307,111 | 12/1981 | Crawley | 424/278 |
| 4,310,523 | 1/1982 | Neumann | 424/240 |
| 4,323,707 | 4/1982 | Suarez et al. | 564/324 |
| 4,380,635 | 4/1983 | Peters | 546/324 |
| 4,418,068 | 11/1983 | Jones | 424/267 |
| 4,442,119 | 4/1984 | Magarian et al. | 424/274 |
| 4,485,096 | 11/1984 | Bell | 424/95 |
| 4,485,097 | 11/1984 | Bell | 424/95 |
| 4,487,780 | 12/1984 | Scheinberg | 424/294 |
| 4,491,574 | 1/1985 | Seifter et al. | 424/10 |
| 4,512,762 | 4/1985 | Spears | 604/21 |
| 4,536,516 | 8/1985 | Harper et al. | |
| 4,675,189 | 6/1987 | Kent et al. | 424/490 |
| 4,696,949 | 9/1987 | Toivola et al. | 514/648 |
| 4,824,436 | 4/1989 | Wolinsky | 604/53 |
| 4,826,672 | 5/1989 | Milius et al. | 424/1 |
| 4,835,002 | 5/1989 | Wolf et al. | 426/590 |
| 4,839,155 | 6/1989 | Mccague | 424/1 |
| 4,859,585 | 8/1989 | Sonnenschein et al. | 435/29 |
| 4,879,315 | 11/1989 | Magarian et al. | 514/754 |
| 4,929,602 | 5/1990 | Harker et al. | 514/18 |
| 4,962,091 | 10/1990 | Eppstein et al. | 514/2 |
| 4,968,350 | 11/1990 | Bindschaedler et al. | 106/170 |
| 4,973,755 | 11/1990 | Grafe et al. | 564/324 |
| 4,990,538 | 2/1991 | Harris et al. | 514/648 |
| 4,994,033 | 2/1991 | Shockey et al. | 604/101 |
| 4,996,225 | 2/1991 | Toivola et al. | 514/428 |
| 4,997,652 | 3/1991 | Wong | 424/428 |
| 5,008,279 | 4/1991 | Franckowiak et al. | 514/345 |
| 5,009,659 | 4/1991 | Hamlin et al. | 606/159 |
| 5,015,666 | 5/1991 | Magarian et al. | 514/754 |
| 5,026,537 | 6/1991 | Daddona et al. | 424/1.1 |
| 5,032,679 | 7/1991 | Brandley et al. | 536/21 |
| 5,043,335 | 8/1991 | Kleinschroth et al. | 514/211 |
| 5,047,431 | 9/1991 | Schickaneder et al. | 514/648 |
| 5,049,132 | 9/1991 | Schaffer et al. | 604/101 |
| 5,053,033 | 10/1991 | Clarke et al. | 606/3 |
| 5,059,166 | 10/1991 | Fischell et al. | 600/3 |
| 5,066,789 | 11/1991 | Srinivasan et al. | 530/388 |
| 5,075,321 | 12/1991 | Schreiber | 514/317 |
| 5,098,903 | 3/1992 | Magarian et al. | 514/255 |
| 5,102,402 | 4/1992 | Dror et al. | 604/265 |
| 5,108,989 | 4/1992 | Amento et al. | 514/12 |
| 5,112,305 | 5/1992 | Barath et al. | 704/96 |
| 5,114,719 | 5/1992 | Sabel et al. | 424/422 |
| 5,116,864 | 5/1992 | March et al. | 514/455 |
| 5,120,535 | 6/1992 | Marquardt et al. | 424/85.5 |
| 5,140,012 | 8/1992 | McGovern et al. | 514/19 |
| 5,166,143 | 11/1992 | Ondetti et al. | 514/89 |
| 5,171,217 | 12/1992 | March et al. | 604/53 |
| 5,176,617 | 1/1993 | Fischell et al. | 600/3 |
| 5,180,366 | 1/1993 | Woods | 604/96 |
| 5,185,260 | 2/1993 | Crissman et al. | 435/244 |
| 5,189,046 | 2/1993 | Burch et al. | 514/330 |
| 5,189,212 | 2/1993 | Ruenitz | 562/468 |
| 5,192,525 | 3/1993 | Yang et al. | 424/11 |
| 5,199,939 | 4/1993 | Dake et al. | 600/3 |
| 5,208,019 | 5/1993 | Hanson et al. | 424/85 |
| 5,213,576 | 5/1993 | Abiuso et al. | 604/96 |
| 5,213,580 | 5/1993 | Slepian et al. | 623/1 |
| 5,216,126 | 6/1993 | Cox et al. | 530/350 |
| 5,219,548 | 6/1993 | Yang et al. | 424/1 |
| 5,221,620 | 6/1993 | Purchio et al. | 435/69 |
| 5,226,430 | 7/1993 | Spears et al. | 128/898 |
| 5,229,495 | 7/1993 | Ichijo et al. | 530/350 |
| 5,232,444 | 8/1993 | Just et al. | 604/96 |
| 5,238,714 | 8/1993 | Wallace et al. | 427/213 |
| 5,238,950 | 8/1993 | Clader et al. | 514/360 |
| 5,242,397 | 9/1993 | Barath et al. | 604/96 |
| 5,248,764 | 9/1993 | Flanagan et al. | 530/324 |
| 5,254,594 | 10/1993 | Niikura et al. | 514/648 |
| 5,268,358 | 12/1993 | Fretto et al. | 514/12 |
| 5,270,047 | 12/1993 | Kauffman et al. | 424/422 |
| 5,280,016 | 1/1994 | Conrad et al. | 514/56 |
| 5,280,109 | 1/1994 | Miyazono et al. | 530/399 |
| 5,282,785 | 2/1994 | Shapland et al. | 604/21 |
| 5,283,257 | 2/1994 | Gregory et al. | 514/458 |
| 5,284,763 | 2/1994 | Derynk et al. | 435/240 |
| 5,284,869 | 2/1994 | Bisaccia et al. | 514/455 |
| 5,288,711 | 2/1994 | Mitchell et al. | 514/36 |
| 5,296,492 | 3/1994 | Shiozawa et al. | 514/337 |
| 5,304,325 | 4/1994 | Kaufman et al. | 252/312 |
| 5,304,541 | 4/1994 | Purchio et al. | 514/12 |
| 5,308,622 | 5/1994 | Casscells et al. | 424/422 |
| 5,308,862 | 5/1994 | Ohlstein et al. | 514/411 |
| 5,314,679 | 5/1994 | Lewis et al. | 424/9 |
| 5,316,766 | 5/1994 | Baldus et al. | 424/94 |
| 5,324,736 | 6/1994 | Magarin et al. | 514/317 |
| 5,326,757 | 7/1994 | Demopoulos | 514/167 |
| 5,328,471 | 7/1994 | Slepian | 604/101 |
| 5,332,584 | 7/1994 | Scher et al. | 424/408 |
| 5,340,925 | 8/1994 | Lioubin et al. | 530/395 |
| 5,346,702 | 9/1994 | Na et al. | 424/490 |
| 5,346,993 | 9/1994 | Miyazono et al. | 530/399 |
| 5,354,562 | 10/1994 | Platz et al. | 424/489 |
| 5,354,774 | 10/1994 | Deckelbaum t al. | 514/455 |
| 5,354,801 | 10/1994 | O'toole et al. | 524/461 |
| 5,356,713 | 10/1994 | Charmot et al. | 428/407 |
| 5,362,424 | 11/1994 | Lee et al. | 264/4.3 |
| 5,364,632 | 11/1994 | Benita et al. | 424/450 |
| 5,380,716 | 1/1995 | Conrad et al. | 514/56 |
| 5,384,332 | 1/1995 | Fontana | 514/648 |
| 5,385,935 | 1/1995 | Tamai et al. | 514/535 |
| 5,389,670 | 2/1995 | Fontana | 514/443 |
| 5,391,557 | 2/1995 | Cullinan et al. | 514/324 |
| 5,393,763 | 2/1995 | Black et al. | 514/333 |
| 5,393,772 | 2/1995 | Yue et al. | 514/410 |
| 5,393,785 | 2/1995 | Labrie et al. | 514/622 |
| 5,395,842 | 3/1995 | Labrie et al. | 514/320 |
| 5,401,730 | 3/1995 | Sauvage et al. | 514/165 |
| 5,407,609 | 4/1995 | Tice et al. | 264/46 |
| 5,418,252 | 5/1995 | Williams | 514/443 |
| 5,423,885 | 6/1995 | Williams | 623/1 |
| 5,424,331 | 6/1995 | Shlyankevich | 514/456 |
| 5,426,123 | 6/1995 | Fontana | 514/651 |
| 5,429,634 | 7/1995 | Narcisco, Jr. | 604/890.1 |
| 5,434,166 | 7/1995 | Glasebrook | 514/317 |
| 5,436,243 | 7/1995 | Sachs et al. | 514/231 |
| 5,439,923 | 8/1995 | Cullinan | 514/324 |
| 5,439,931 | 8/1995 | Sales | 514/443 |
| 5,441,947 | 8/1995 | Dodge et al. | 514/179 |
| 5,441,964 | 8/1995 | Bryant et al. | 514/324 |
| 5,441,965 | 8/1995 | Sall et al. | 514/324 |
| 5,441,966 | 8/1995 | Dodge | 514/324 |
| 5,441,986 | 8/1995 | Thompson | 514/648 |
| 5,444,164 | 8/1995 | Purchio et al. | 536/23.5 |
| 5,445,941 | 8/1995 | Yang | 435/6 |
| 5,446,053 | 8/1995 | Keohane | 514/324 |
| 5,447,941 | 9/1995 | Zuckerman | 514/324 |
| 5,453,442 | 9/1995 | Bryant et al. | 514/408 |
| 5,455,275 | 10/1995 | Fontana | 514/648 |

| | | | |
|---|---|---|---|
| 5,457,113 | 10/1995 | Cullinan et al. ............... 514/319 |
| 5,457,116 | 10/1995 | Black et al. ............... 514/324 |
| 5,457,117 | 10/1995 | Black et al. ............... 514/337 |
| 5,458,568 | 10/1995 | Racchini et al. ............... 604/19 |
| 5,462,937 | 10/1995 | Cullinan et al. ............... 514/212 |
| 5,466,810 | 11/1995 | Godfrey ............... 546/202 |
| 5,468,746 | 11/1995 | Casagrande et al. ............... 514/235.5 |
| 5,470,883 | 11/1995 | Stromberg ............... 514/648 |
| 5,472,985 | 12/1995 | Grainger et al. ............... 514/651 |
| 5,478,847 | 12/1995 | Draper ............... 514/333 |
| 5,480,888 | 1/1996 | Kodama et al. ............... 514/320 |
| 5,480,904 | 1/1996 | Bryant et al. ............... 514/443 |
| 5,482,949 | 1/1996 | Black et al. ............... 514/324 |
| 5,482,950 | 1/1996 | Bryant et al. ............... 514/324 |
| 5,484,795 | 1/1996 | Bryant et al. ............... 514/319 |
| 5,484,796 | 1/1996 | Bryant et al. ............... 514/319 |
| 5,484,798 | 1/1996 | Bryant et al. ............... 514/324 |
| 5,484,808 | 1/1996 | Grinnell ............... 514/443 |
| 5,489,587 | 2/1996 | Fontana ............... 514/233.5 |
| 5,491,159 | 2/1996 | Malamas ............... 514/374 |
| 5,491,173 | 2/1996 | Toivola et al. ............... 514/648 |
| 5,492,921 | 2/1996 | Bryant et al. ............... 514/324 |
| 5,492,922 | 2/1996 | Palkowitz ............... 514/324 |
| 5,492,926 | 2/1996 | Cullinan et al. ............... 514/422 |
| 5,492,927 | 2/1996 | Gitter et al. ............... 514/443 |
| 5,496,828 | 3/1996 | Cullinan ............... 514/324 |
| 5,498,775 | 3/1996 | Novak et al. ............... 514/25 |
| 5,508,292 | 4/1996 | Sall et al. . |
| 5,510,370 | 4/1996 | Hock et al. . |
| 5,516,781 | 5/1996 | Morris et al. ............... 514/291 |
| 5,516,807 | 5/1996 | Hupe et al. ............... 514/673 |
| 5,519,042 | 5/1996 | Morris et al. ............... 514/378 |
| 5,521,171 | 5/1996 | Sorenson ............... 514/188 |
| 5,521,191 | 5/1996 | Greenwald ............... 514/262 |
| 5,527,337 | 6/1996 | Stack et al. ............... 606/198 |
| 5,534,527 | 7/1996 | Black et al. ............... 514/333 |
| 5,541,174 | 7/1996 | Sorenson ............... 514/186 |
| 5,545,409 | 8/1996 | Laurencin et al. . |
| 5,545,569 | 8/1996 | Grainger et al. ............... 436/518 |
| 5,552,415 | 9/1996 | May ............... 514/324 |
| 5,563,054 | 10/1996 | Briggs et al. ............... 435/127 |
| 5,567,713 | 10/1996 | Cullinan et al. ............... 514/324 |
| 5,571,714 | 11/1996 | Dasch et al. ............... 435/240.27 |
| 5,574,047 | 11/1996 | Bumol et al. ............... 514/324 |
| 5,595,722 | 1/1997 | Grainger et al. ............... 424/9.2 |
| 5,597,578 | 1/1997 | Brown et al. ............... 424/422 |
| 5,599,844 | 2/1997 | Grainger et al. ............... 514/651 |
| 5,610,166 | 3/1997 | Singh ............... 514/324 |
| 5,610,168 | 3/1997 | Draper ............... 514/333 |
| 5,622,975 | 4/1997 | Singh et al. ............... 514/324 |
| 5,639,274 | 6/1997 | Fischell et al. ............... 604/96 |
| 5,641,790 | 6/1997 | Draper ............... 514/333 |
| 5,681,835 | 10/1997 | Willson ............... 514/237.5 |
| 5,686,467 | 11/1997 | Bumol et al. ............... 514/324 |
| 5,688,813 | 11/1997 | Sall et al. ............... 514/324 |
| 5,726,186 | 3/1998 | Grese ............... 514/321 |
| 5,747,510 | 5/1998 | Draper ............... 514/333 |
| 5,770,609 | 6/1998 | Grainger et al. ............... 514/319 |
| 5,773,479 | 6/1998 | Grainger et al. ............... 514/651 |
| 5,811,447 | 9/1998 | Kunz et al. ............... 514/411 |
| 5,847,007 | 12/1998 | Grainger et al. ............... 514/651 |
| 5,945,456 | 8/1999 | Grainger et al. ............... 514/651 |

FOREIGN PATENT DOCUMENTS

| | | | |
|---|---|---|---|
| 54168A1 | 6/1982 | (EP) | ............... C07C/93/06 |
| 0095875 | 12/1983 | (EP) | ............... C07C/33/26 |
| 0260066B1 | 3/1988 | (EP) | ............... C07C/217/54 |
| 0365863 B1 | 5/1990 | (EP) . |
| 0374044 B1 | 6/1990 | (EP) . |
| 0451202 B1 | 10/1991 | (EP) . |
| 0577215 | 1/1993 | (EP) . |
| 0 526 102 | 2/1993 | (EP) | ............... A61M/29/02 |
| 0542679 | 5/1993 | (EP) . |
| 0588518A1 | 2/1994 | (EP) . |
| 0584952A1 | 3/1994 | (EP) | ............... A61K/31/445 |
| 0606613 | 7/1994 | (EP) | ............... G01N/33/531 |
| 0629697 | 12/1994 | (EP) . |
| 0 635 270 A1 | 1/1995 | (EP) . |
| 0 664 121 | 7/1995 | (EP) | ............... A61K/31/445 |
| 0 664 122 | 7/1995 | (EP) | ............... A61K/31/445 |
| 0670162 | 9/1995 | (EP) | ............... A61K/31/445 |
| 0674903 | 10/1995 | (EP) | ............... A61K/31/445 |
| 0675121 | 10/1995 | (EP) | ............... C07D/333/56 |
| 0699673 | 3/1996 | (EP) | ............... C07D/333/56 |
| 1015787 | 1/1966 | (GB) . |
| 2273873 | 6/1994 | (GB) | ............... A61K/31/48 |
| 85/00107 | 1/1985 | (WO) | ............... A61K/31/13 |
| 88/10259 | 12/1988 | (WO) | ............... C07D/313/00 |
| 90/01969 | 3/1990 | (WO) . |
| 90/13293 | 11/1990 | (WO) | ............... A61K/31/40 |
| 91/15219 | 10/1991 | (WO) . |
| 91/15222 | 10/1991 | (WO) . |
| 92/00330 | 1/1992 | (WO) | ............... C07K/15/28 |
| 92/06068 | 4/1992 | (WO) | ............... C07C/217/18 |
| 92/08480 | 5/1992 | (WO) . |
| 92/11890 | 7/1992 | (WO) | ............... A61M/25/00 |
| 92/11895 | 7/1992 | (WO) | ............... A61K/31/00 |
| 92/18546 | 10/1992 | (WO) . |
| 92/19273 | 11/1992 | (WO) . |
| 92/21363 | 12/1992 | (WO) . |
| 93/07748 | 4/1993 | (WO) . |
| 93/09228 | 5/1993 | (WO) . |
| 93/09790 | 5/1993 | (WO) . |
| 93/10808 | 6/1993 | (WO) . |
| 93/11757 | 6/1993 | (WO) | ............... A61K/31/135 |
| 93/16724 | 9/1993 | (WO) | ............... A61K/39/00 |
| 93/19746 | 10/1993 | (WO) . |
| 94/04164 | 3/1994 | (WO) . |
| 94/04178 | 3/1994 | (WO) . |
| 94/07529 | 4/1994 | (WO) | ............... A61K/39/00 |
| 94/08604 | 4/1994 | (WO) . |
| 94/08605 | 4/1994 | (WO) . |
| 94/09764 | 5/1994 | (WO) | ............... A61K/31/00 |
| 94/09812 | 5/1994 | (WO) . |
| 94/10187 | 5/1994 | (WO) . |
| 94/15589 | 7/1994 | (WO) | ............... A61K/9/50 |
| 94/15590 | 7/1994 | (WO) | ............... A61K/9/51 |
| 94/15646 | 7/1994 | (WO) | ............... A61K/48/00 |
| 94/16706 | 8/1994 | (WO) . |
| 94/17786 | 8/1994 | (WO) | ............... A61K/9/16 |
| 94/18967 | 9/1994 | (WO) | ............... A61K/31/415 |
| 94/18968 | 9/1994 | (WO) | ............... A61K/31/415 |
| 94/19000 | 9/1994 | (WO) | ............... A61K/37/02 |
| 94/19001 | 9/1994 | (WO) | ............... A61K/37/02 |
| 94/19003 | 9/1994 | (WO) | ............... A61K/37/02 |
| 94/20096 | 9/1994 | (WO) | ............... A61K/31/40 |
| 94/20097 | 9/1994 | (WO) | ............... A61K/31/40 |
| 94/21679 | 9/1994 | (WO) | ............... A07K/13/00 |
| 94/23068 | 10/1994 | (WO) | ............... C12Q/1/68 |
| 94/23699 | 10/1994 | (WO) | ............... A61K/9/14 |
| 94/25588 | 11/1994 | (WO) . |
| 94/26291 | 11/1994 | (WO) | ............... A61K/37/02 |
| 94/26303 | 11/1994 | (WO) | ............... A61K/39/00 |
| 94/28721 | 12/1994 | (WO) | ............... A01N/43/42 |
| 95/03036 | 2/1995 | (WO) . |
| 95/04544 | 2/1995 | (WO) | ............... A61K/38/22 |
| 95/10611 | 4/1995 | (WO) | ............... C12N/15/12 |
| 94/26888 | 10/1995 | (WO) . |
| 96/24356 | 8/1996 | (WO) | ............... A61K/31/55 |

OTHER PUBLICATIONS

Rutqvist, L.E., et al., "Cardiac and Thromboembolic Morbidity Among Postmenopausal Women with Early–Stage Breast Cancer in a Randomized Trial of Adjuvant Tamoxifen", *Journal of the National Cancer Institute*, 85, 1398–1406, (1993).

Standley, P.R., et al., "Tamoxifen (an Antiestrogen) Reduces $K^+$– and Agonist–Induced Vascular Contractility in Rat Resistance Vessels", Abstract No. 159 (Source and Date Unavailable).

Thompson, N.L., et al., "Expression of Transforming Growth Factor β1 in Specific Cells and Tissues of Adult and Neonatal Mice", *Journal of Cell Biology*, 108, 661–669 (1989).

Wilensky, R.L., et al., "Regional and Arterial Localization of Radioactive Microparticles after Local Delivery by Unsupported or Supported Porous Balloon Catheters", *American Heart Journal*, 129, 852–859 (1995).

"Breast Cancer Prevention Trial Should Resume, ODAC Says", *The Breast Cancer Letter*, 20, 4–5(1994).

"Coronary Artery Disease: Restenosis and Reocclusion After Surgical and Nonsurgical Inverventions, Part I", *Drug & Market Development*, 5, 121–129 (Sep. 26, 1994).

"Nolvadex Tamoxifene Citrate", *ICI Pharma*, 64033–02, Rev. L/07/92.

"Prevention of Coronary Heart Disease", In: *Avery's Drug Treatment—Principles and Practice of Clinical Pharmocology and Therapeutics*, Speight, T. M., (ed.), Williams and Wilkins, Baltimore, 594–595, (1987).

Shiga Medical Center for Adult Diseases, "The Impact of Tranilast on Restenosis Following Coronary Angioplasty: The Tranilast Restenosis Following Angioplasty Trial (TREAT)", *Circulation*, 90, I–82, Abstract No. 0, (Oct. 1988).

AinMelk, Y., et al., "Tamoxifen Citrate Therapy in Male Fertility", *Fertility and Sterility*, 48, 113–117. (Jul. 1987).

Alleman, et al., "Distribution, Kinetics, and Elimination of Radioactivity after Intravenous and Intramuscular Injection of 14C–Savoxepoine Loaded Poly (D,L–lactic acid) Nanospheres to Rats", *J. Controlled Release*, 29, 97–104 (1994).

Alleman, E., et al., "Drug Loaded Poly(lactic acid) Nanoparticles Produced by a Versible Salting–out Process: Purification of an Injectable Dosage Form", *Eur. J. Pharm. Biopharm*, 39, 13–18, (1993).

Anderson, et al., "Effects of Acetate Dialysate on Transforming Growth Factor B1–interluekin and B2–micorglobulin Plasma Levels", *Kidney International*, 40, 1110–1117, (1991).

Anker, et al., "Plasma Levels of the Atherogenic Amino Acid Homocysteine in Post–Menopausal Women with Breast Cancer Treated with Tamoxifen", *Int. J. Cancer*, 60, 363–368, (1995).

Assoian, et al., "Type Beta Transforming Growth Factor in Human Platelets: Release During Platelet Degranulation and Action on Vascular Smooth Muscle Cells", *J. Cell. Biol.*, 102, 1217–1223, (Apr. 1986).

Attwood, et al., "A Light Scattering Study on Oil–in–Water Microemulsions", *Int'l J. Pharm*, 52, 165–171 (1989).

Bagdade, J.D., et al., "Effects of Tamoxifen Treatment on Plasma Lipids and Lipoprotein Lipid Composition", *J. Clinical Endocrinology and Metabolism*, 70, 1132–1135, (1990).

Barath, et al., "Low Dose of Antitumor Agents Prevents Smooth Muscle Cell Proliferation After Endothelial Injury", *JACC*, 13, 252A(Feb. 1989).

Barbacid, et al., "Binding of [acetyl–14C]Trichodermin to the Peptidyl Transferase Center of Eukaryotic Ribosomes", *Eur. J. Biochem*, 44, 437–444 (1974).

Beck et al., "Poly(DL–lactide–co–glycolide)/norethisterone microacapsules: an injectible biodegradable contraceptive", *Biol. Reprod.*, 28, 186–195 (1983).

Benita, et al., "Submicron Emulsions as Colloidal Drug Carriers for Intravenous Administration: Comprehensive Physicochemical Characterization", *J. of Pharmaceutical Sciences*, 82 1069–1079 (Nov. 1993).

Bertelli, et al., "Adjuvant Tamoxifen in Primary Breast Cancer: Influence on Plasma Lipids and Antitrhombin III Levels", *Breast Cancer Res. and Treatment*, 12, 307–310 (1988).

Bier, et al., "Arterial Remodeling: Importance in Primary Versus Restenoic Lesions", *JACC*, p. 139A, Abstract No. 875–96 (Feb. 1994).

Bluming, "Hormone Replacement Therapy: Benefits and Risks for the General Postmenopausal Female Population and for Women with a History of Prevously Treated Breast Cancer", *Seminars in Oncology*, 20, 662–674 (Dec. 1993).

Brott, et al., "Vessel Remodeling After Angioplasty: Comparative Anatomic Studies", *JACC*, p. 138A, Abstract No. 878–43, (Feb. 1994).

Bruengger, et al., "Smooth Muscle Cell of the Canine Prostate in Spontaneous Benign Hyperplasia, Steroid Induced Hyperplasia and Estrogen or Tamoxifen Treated Dogs", *J. Urology*, 130, 1208–1210 (Dec. 1983).

Bruning, et al., "Tamoxifen, Serum Lipoproteins and Cardiovascular Risk", *Br. J. Cancer*, 58, 497–499 (1988).

Butta, A., et al., "Induction of Transforming Growth Factor Beta1 in Human Breast Cancer in Vivo Following Tamoxifen Treatment", *Cancer Research*, 52, 4261–4164, (1992).

Casscells, W., et al., "Elimination of Smooth Muscle Cells in Experimental Restenosis: Targeting of Fibroblast Growth Factor Receptors", *Proc. Natl. Acad. Sci. USA*, 89, 7159–7163, (Aug. 1992).

Chander, et al., "Pyrrolidino–4–iodotamoxifen and 4–iodotamoxifen, New Analogues of the Antiestrogen Tamoxifen for the Treatment of Breast Cancer", *Cancer Res.*, 51, 5851–5858, (Nov. 1, 1991).

Chao, et al., "Altered Cytokine Release in Peripheral Blood Mononuclear Cell Cultures from Patients with the Chronic Fatigue Syndrome", *Cytokine*, 3, 292–298, (Jul. 1991).

Chapman, G.D., et al., "A Bioabsorbable Stent: Initial Experimental Results", *Supplement III Circulation*, 82, p. III–72, Abstract No.0283 (Oct. 1990).

Charlier, et al., "Tamoxifen in the Treatment of Breast Cancer", *J. Gynecol. Obstet Biol. Reprod.*, 23, 751–756 (1994).

Chauhan, et al., "Activation of Transforming Growth Factor B is Inversely Correlated with Three Major Risk Factors for Cornary Artery Disease: Lipoprotein(a), LDL–Cholesterol and Plasminogen Activator Inhibitor–I", *Circulation*, 90 p. I–623, Abstract No. 3354 (Oct. 1994).

Clowes, et al., "Kinetics of Cellular Proliferation after Arterial Injury—III. Endothelium and Smooth Muscle Growth in Chronically Denuded Vessels", *Laboratory Investigation*, 54, 295–303 (1986).

Clowes, et al., "Kinetics of Cellular Proliferation after Artterial Injury—I. Smooth Muscle Growth in the Absence of Endothelium", *Laboratory Investigation,* 49, 327–333 (1983).

Clowes, et al., "Mechanisms of Stenosis after Arterial Injury", *Laboratory Investigation,* 49, 208–215 (1983).

Clowes, et al., "Significance of Quiescent Smooth Muscle Migration in the Injured Rat Carotid Artery", *Cir. Res.,* 56, 139–145 (Jan. 1985).

Cohen, et al., "Controlled Delivery Systems for Proteins Based on Poly(lactic/glycolic acid) Microspheres", *Pharmaceutical Research,* 8, 713–720 (1991).

Colletta, A.A., et al., "Anti–oestrogens induce the secretion of active transforming growth factor beta from human fetal fibroblasts", *Br. J. Cancer,* 62, 405–409, (1990).

Coombes, R.C., et al., "Idoxifene: Report of a Phase I Study in Patients with Metastatic Breast Cancer", *Cancer Research,* 55, 1070–1074, (Mar. 1, 1995).

Cotton, "Restenosis Trials Suggest Role for Remodeling, Medical News and Perspective", *JAMA,* 271, 1302–1305 (1994).

Cowsar, et al., "Poly(actide–co–glycolide) Microcapsules for Controlled Release of Steroids", *Methods Enzymology,* 112, 101–116 (1985).

Craig, et al., "Anticoagulant Drugs", *Modern Pharmacology,* p. 399, Little, Brown and Company (1982).

Currier, "Restenosis After Percutaneous Transluminal Coronary Angioplasty: Have We Been Aiming at the Wrong Target?", *JACC,* 25, 516–20 (Feb. 1995).

Danielpour, "Improved Sandwich Enzyme–linked Immunosorbent Assays Transforming Growth Factor B1",*J. Immunol. Methods,* 158, 17–25 (1993).

Danielpour, D., et al., "Evidence for Differential Regulation of TGF–Beta1 and TGF–Beta2 Expression in Vivo by Sandwich Enzyme–linked Immunosorbent Assays", *Annals N.Y. Acad. Sci.,* 593, 300–302, (1990).

Danielpour, D., et al., "Immunodetection and Quantitation of the Two Forms of Transforming Growth Factor–Beta (TGF–Beta1 and TFG–Beta2) Secreted by Cells in Culture", *J. Cell. Physiol.,* 138, 79–86, (1989).

Dasch, J.R., et al., "Capture Immunoassays Specific for TGF–Beta1 and TGF–Beta2: Use in Pharmacokinetic Studies", *Annals N.Y. Acad. Sci.,* 593, 303–305, (1990).

Davies, A.M., et al., "Peroxidase Activation of Tamoxifen and Toremifene Resulting in DNA Damage and Covalently Bound Protein Adducts", *Carcinogenesis,* 16, 539–545, (1995).

DiMario, et al., "Is the Mechanism of Restenosis Device-independent? Serial Assessment with Intracoronary Ultrasound", *Circulation,* 90, p. I–24, Abstract No. 115 (1994).

Dimond, P.F., "TGF–Beta Shows Potential as Therapeutic Agent for Macular Holes", *Genetic Engineering News,* p. 7, 19, (Feb. 1, 1993).

Dowsett, M., "New Developments in the Hormonal Treatment of Breast Cancer", In: The Treatment of Cancer: Beyond Chemotherapy, Conference Documentation, The Glouster Hotel, London, 7 p., (Mar. 13–14, 1995).

Ebner, et al., "Cloning of a Type I TGF–B Receptor and Its Effect on TGF–B Binding to the Type II Receptor", *Science,* 260, 1344–1348 (May 28, 1993).

Eldridge, J.H., et al., "Biodegradable and Biocompatible Poly(DL–Lactide–Co–Glycolide) Microspheres as an Adjuvant for Staphylococcal Enterotoxin B Toxoid Which Enhances the Level of Toxin–Neutralizing Antibodies", *Infection and Immunity,* 59, 2978–2986, (Sep. 1991).

Fanelli, et al., "Restenosis Following Coronary Angioplasty", *Amer. Heart J.,* 119, 357–368 (Feb. 1990).

Farhat, et al., "In Vitro Effect of Oestradiol on Thymidine Uptake in Pulmonary Vascular Smooth Muscle Cell: Role of the Endothelium.", *Br. J. Pharmacol.,* 107, 679–683 (1992).

Faxon, et al., "Restenosis Following Transluminal Angioplasty in Experimental Atherosclerosis.", *Arteriosclerosis,* 4, 189–195 (May/Jun. 1984).

Fischell, T.A., et al., "Low–Dose, beta–Particle Emission From 'Stent' Wire Results in Complete, Localized Inhibition of Smooth Muscle Cell Proliferation", *Circulation,* 90, 2956–2963, (Dec., 1994).

Fischer, et al., "A Possible Mechanism in Arterial Wall for Mediation of Sex Difference in Atherosclerosis Experimental and Molecular Pathology", *Exp. Mol. Pathol.,* 43, 288–296 (1985).

Fischman, D.L., et al., "A Randomized Comparison of Coronary–Stent Placement and Balloon Angioplasty in the Treatment of Coronary Artery Disease", *The New England Journal of Medicine,* 331, 496–501, (Aug., 1994).

Forrester, et al., "A Paradigm for Restenosis Based on Cell Biology: Clues for the Development of New Preventive Therapies\", *JACC,* 17, 758–69 (Mar. 1, 1991).

Frazier–Jessen, et al., "Estrogen odulation of JE/Monocyte Chemoattractant Protein–1 mRNA Expression in Murine Macrophages", *J. Immunol.,* 1828–1845, (Nov. 1, 1994).

Friberg, et al., "Microemulsions and Solubilization by Nonionic Surfactants", *Prog. Colloid and Polymer Sci.,* 56, 16–20 (1975).

Furr, B.J., et al., "The Pharmacology and Clinical Uses of Tamoxifen", *Pharm. Ther.,* 25, 127–205, (1984).

Gasco, et al., "In Vitro Permeation of Azelaic Acid from Viscosized Microemulsions", *International Journal of Pharmaceutics,* 69, 193–196 (1991).

Gasco, M.R., et al., "Long–acting Delivery Systems for Peptides: Reduced Plasma Testosterone Levels in Male Rats after a Single Injection", *Int. J. of Pharmaceut,* 62, 119–123, (1990).

Gertz, et al., "Geometric Remodeling Is Not the Principal Pathogenic Process in Restenosis After Balloon Angioplasty", *Circulation,* 90, 3001–3008 (Dec. 1994).

Gianchelli, et al., "Osteopontin is Elevated during Neointima Formation in Rat Arteries and is a Novel Component of Human Atherosclerosis Plaques.", *J. Clin. Invest.,* 92, 1686–1696, (1993).

Gibbons, et al., "The Emerging Concept of Vascular Remodeling", *New Engl. J. of Medicine,* 330, 1431–1438, (1994).

Glagov, "Intimal Hyperplasia, Vascular Modeling, and the Restenosis Problem", *Circulation,* 89, 2888–2891 (1994).

Glagov, et al., "Compensatory Enlargement of Human Atherosclerotic Coronary Arteries", *New. Engl. J. Med.,* 316, 1371–1375 (May 28, 1987).

Goldman, et al., "Influence of Pressure on Permeability of Normal and Diseased Muscular Arteries to Horseradish Peroxidase.", *Atherosclerosis,* 65, 215–225 (1987).

Grainger, et al., "A large accumulation of non–muscle myosin occurs at first entry into M phase in rat vascular smooth–muscle cells.", *Biochem. J.,* 277, 145–151 (1991).

Grainger, et al., "Activation of transforming growth factor B is inhibited by apoliiopoprotein (a) in vivo", *Circulation*, 90, p. I–623, Abstract No. 3353 (Oct. 1994).

Grainger, et al., "Activation of transforming growth factor B is inhibited in transgenic apolipoprotein(a) mice", *Nature*, 370, 460–462 (Aug. 11, 1994).

Grainger, et al., "Active and acid activatable TGF–B in human sera, platelets and plasma", *Clin. Chem. Acta.*, 235, 11–31 (1995).

Grainger, et al., "Active TGF–B is Depressed Five–Fold in Tripple Vessel Disease Patients Compared with Syndrom X Patients", *J. of Cell. Biochem*, 18A, p. 267, Abstract No. E111 (1994).

Grainger, et al., "Active Transforming Growth Factor B is Depressd in Patients with Three Vessel Coronary Artery Disease", *Circulation*, 90, p. I–512, Abstract No. 2754 (Oct. 1994).

Grainger, et al., "Heparin Decreases the Rate Vascular Smooth Muscle Cells by Releasing Transforming Growth Factor B–like Activity from Serum.", *Cardiovasc. Res.*, 27, 2238–2247 (1993).

Grainger, et al., "Mitogens for Adult Rat Aortic Vascular Smooth Muscle Cells in Serum–Free Primary Culture.", *Cardiovascular Res.*, 28, 1238–1242 (1994).

Grainger, et al., "The Serum Concentration of Active Transforming Growth Factor (beta) is Severly Depressed in Advanced Atherosclerosis", *Nature Medicine,*, vol. 1, No. 1, pp. 74–80, (Jan. 1995).

Grainger, et al., "Transforming growth factor beta; the key to understanding lipoprotein(a)", *Current Opinion In Lipidology*, 6, 81–85 (1995).

Grainger, D.J., "Tamoxifen: Teaching an old drug new tricks?—", *Nature Medicine*, vol. 2, No. 4, pp. 381–385, (Apr. 1996).

Grainger, D.J., et al., "A Pivotol Role for TGF–Beta in Atherogenesis?", *Biol. Rev.*, 70, 571–596, (1995).

Grainger, D.J., et al., "Effect of Tamoxifen in the Rat Carotid Injury Model In Vivo", Manuscript in Preparation, (1996).

Grainger, D.J., et al., "Proliferation of Human Smooth Muscle Cells Promoted by Lipoprotein(a)", *Science*, 260, 1655–58, (Jun. 1993).

Grainger, D.J., et al., "Tamoxifen Decreases the Rate of Proliferation of Rat Vascular Smooth–Muscle Cells in Culture by Inducing Production of Transforming Growth Factor Beta", *Biochem J.* 294, 109–112, (1993).

Grainger, D.J., et al., "Transforming growth factor Beta decreases the rate of proliferation of rat vascular smooth muscle cells by extending the G2 phase of the cell cycle and delays the rise in cyclic AMP before entry into M phase", *Biochem J.*, 299, 227–235, (1994).

Gref, et al., "Biodegradable Long–Circulating Polymeric Nanoshoeres.", *Science*, 263, 1600–1603 (Mar. 18, 1994).

Grey, A.B., et al., "The Effect of the Anti–Estrogen Tamoxifen on Cardiovascular Risk Factors in Normal Postmenopausal Women", *J. Clinical Endocrinology and Metabolism*, 80, 3191–3195, (1995).

Hall, I.H., et al., "Hypolipidemic Activity of Tetrakis–mu–(trimethylamine–boranecarboxylato)–bis(trimethylamine–carboxyboran e)–dicopper(II) in Rodents and Its Effect on Lipid Metabolism", *J. Pharmaceut. Sci.*, 73, 973–977, (Jul. 1984).

Hanke, Hartmut, Md, et al., "Inhibition of Cellular Proliferation After Experimental Balloon Angioplasty by Low–Molecular–Weight Heparin", *Circulation*, 85, 1548–56, (Apr. 1992).

Harpel, et al., "Plasmin Catalysis Binding of Lipoprotein (A) to Immobilized Fibrinogen and Fibrin.", *Proc. Natl. Acad. Sci. USA*, 86, 384793851 (1989).

Heldin, et al., "Demonstration of an Antibody Against Platelet–Derived Growth Factor.", *Exp. Cell. Res.*, 136, 255–261 (Dec. 1981).

Heller, et al., "Preparation of Polyacetals by the Reaction of Divinyl Ethers and Polyols.", *J. Polymer Science, Polymer Letters Edition*, 18, 293–297 (Apr. 1980).

Henriksson, et al., "Hormonal Regulation of Serum Lp (a) Levels.", *J. Clin. Invest.*, 89, 1166–1171 (Apr. 1992).

Hofmann, et al., "Enhancement of the Antiproliferative Effect of cis–Diamminedichloroplatinum(II) and Nitrogen Mustard by Inhibitors of Protein Kinase C", *Int. J. Cancer*, 42, 382–388 (1988).

Holmes, "Remodeling Versus Smooth Muscle Cell Hyperpasia.", Restenosis Summit VI, The Cleveland Clinic Foundation, 222–223 (May 1994).

Hwang, et al., "Effects of Platelet–Contained Growth Factors (PDGF, EGF, IGF–1, and TGF–B) on DNA Synthesis in Porcine Aortic Smooth Muscle Cells in Culture.", *Exp. Cell Res.*, 200, 358–360, (1992).

Isner, "Vascular Remodeling: Honey, I Think I Shrunk the Artery", *Circulation*, 89, 2937–2841 (Jun. 1994).

Johnson, et al., "Coronary Atherectomy: Light Microscopic and Immunochemical Study of Excised Tissues", *Supp. II Circulation*, 78, p. 11–82, Abstract No. 0327 (Oct. 1988).

Kakuta, et al., "The Impact of Arterial Remodeling on the Chronic Lumen Size After Angioplasty in the Atherosclerotic Rabbit.", *JACC*, p. 138A, Abstract No. 875–95 (Feb. 1994).

Kemp, et al., "Inhibition of PDGF BB Stimulated DNA Synthesis in Rat Aortic Vascular Smooth Muscle Cells by the Expression of a Truncated PDGF Receptor.", *FEBS Letters*, 336, 119–123 (Dec. 1993).

Kemp, et al., "The Id gene is activated by serum but is not required for de–differentiation in rat vascular smooth muscle cells", *Biochem J.*, 277, 285–288 (1991).

Kirschenlohr, et al., "Proliferation of Human Aortic Vascular Smooth Muscle Cells in Culture is Modulated by Active TGF–Beta", *Cardiovascular Res.*, 29, 848–855 (1995).

Kirschenlohr, H.L., et al., "Adult Human Aortic Smooth Muscle Cells in Culture Produce Active TFG–Beta", *Amer. J. Physiol*, 265, C571–C576, (1993).

Knabbe, C., et al., "Evidence That Transforming Growth Factor beta is a Hormonally Regulated Negative Growth Factor in Human Breast Cancer Cells", *Cell*, 48, 417–428, (Feb., 1987).

Knabbe, C., et al., "Induction of Transforming Growth Factor Beta by the Antiestrogens Droloxifene, Tamoxifen, and Toreifene in MCF–7 Cells", *Am. J. Clin. Oncol. (CCT)*, 14, S15–S20, (1991).

Koff, et al., "Negative Regulation of G1 in Mammalian Cells: Inhibition of Cyclin E–Dependent Kinase by TGF–B.", *Science*, 260, 536–538 (Apr. 23, 1993).

Kotoulas, I.G., et al., "Tamoxifen Treatment in Male Infertility. I. Effect on Spermatozoa", *Fertility and Sterility*, 61, 911–914, (May 1994).

Kovach, et al., "Serial Intravascular Ultrasound Studies Indicates that Chronic Recoil is an Important Mechanism of Restenosis Following Transcathereter Therapy.", *JAAC*, 21, p. 484A, Abstract No. 835–3 (1993).

Koyama, N., et al., "Regulation of Smooth Muscle Cells Migration by a New Autocrine Migration Factor and TGF-beta", *Circulation*, 84, Abstract No. 1829, p. II–459, (1991).

Kreuzer, et al., "Lipoprotein(a) Displays Increased Accumulation Compared with Low–Density Lipoprotein in the Murine Arterial Wall", *Chemistry and Physics of Lipids*, 67/68, 175–190 (1990).

Kuntz, et al., "Defining Coronary Restenosis Newer Clinical and Angiographic Paradigms.", *Circulation*, 88, 1310–1323 (Sep. 1993).

Kunz, et al., "Inhibition of Microfilament Reorganization Following Balloon Angioplasty Decreases Extent of Geometric Remodeling in Restenosis", *J. of Amer. Coll. of Cardiology*, American College of Cardiology 44th Annual Scientific Session, Abstract No. 122292 (Mar. 19–22, 1995).

Kunz, et al., "Sustained Dilation and Inhibition of Restenosis in a Pig Femoral Artery Injury Model", *Circulation*, 90, p. I–297, Abstract No. 1598(Oct. 1994).

Kunz, L.L., et al., "Efficacy of Cytochalasin B in Inhibiting Coronary Restenosis Caused by Chronic Remodeling After Balloon Trauma in Swine", *Journal of the American College of Cardiology*, Supplement A, Abstract No. 984–23, p. 302, (Mar. 1995).

Labhsetwar, V., "Nanoparticles for site specific delivery of U–86983 in restenosis on pig coronary arteries", *Proc. Intern. Symp. Control. Rel. Bioact. Mater.*, 22, 182–183, (1995).

Lafont, et al., "Post–Angioplasty Restenosis in the Atherosclerotic Rabbit: Proliferative Response or Chronic Constriction", *Circulation*, 88, p. I–521, Abstract No. 2806 (1993).

Langbein, W., "Too many drugs, too little value in CV conditions", *In Vivo, The Business and Medicine Report*, 14–20, (Jun. 1995).

Lazier, C.B., et al., "Comparison of the Effects of Tamoxifen and of a Tamoxifen Analogue that Does Not Bind the Estrogen Receptor on Serum Lipid Profiles in the Cockerel", *Biochem. Cell Biol.*, 68, 210–217, (1990).

Lefer, "Role of Transforming Growth Factor Beta is Cardioprotection of the Ischemic–Reperfused Myocardium", *Growth Factors and the Cardiovascular System*, P. Cummins, ed., Kluwer Academic Publishers, pp. 249–260 (1993).

Lefer, et al., "Mechanisms of the Cardioprotective Effect of Transforming Growth Factor B1 in Feline Myocardial Ischemia and Reperfusion", *PNAS (USA)*, 90, 1018–1022, (Feb. 1993).

Lefer, A.M., et al., "Mediation of Cardioprotection by Transforming Growth Factor Beta", *Science*, 249, 61–64, (Jul. 1990).

Lehmann–Bruinsma, et al., "Transforming Growth Factor B2(TGF–B) Suppression of Smooth Muscle Cell (SMC) Proliferation After Balloon Angioplasty of Rat Carotid Arteries", *Clin. Res. 42*, Abstract No. 4A, (Feb. 9–12, 1994).

Leroux, et al., "New Approach for the Preparation of Nanoparticles by an Emulsification–Diffusion Method", *Eur. J. Pharm. Biopharm*, 41, 14–18 (1995).

Leroux, J.C., et al., "Interanalization of poly(D L–lactic acid) nanoparticles by isolated human leukocytes and analysis of plasma proteins adsorbed onto the particles", *J. Biomed. Mater. Res.*, 28, 471–481, (1994).

Levy, M.Y., "Drug Release from Submicronized O/W Emulsion: A New In Vitro Kinetic Evaluation Model", *Intl. J. Pharmaceut*, 66, 29–37, (1990).

Levy, R.J., et al., "Strategies for Treating Arterial Restonosis Using Polymeric Controlled Release Implants", Abstract, Proc. Am. Chem. Soc. Symp. In: *Biotechnol Bioact. Poly*, C.G. Gebelein, (ed.), 259–268, (1994).

Li, et al., "Structure and Dynamics of Microemulsions which Mimic the Lipid Phase of Low–Density Lipoproteins", *Biochimica et Biophysica Acta*, 1042, 42–50 (1990).

Liaw, et al., "Osteopontin Promotes Vascular Cell Adhesion and Spreading and is Chemotactic for Smooth Muscle Cells in Vitro", *Cir. Res.*, 74, 214–224 (Feb. 21, 1992).

Lin, et al., "Expression Cloning of the TGF–B Type II Receptor, a Functional Transmembrane Serine/Threonine Kinase.", *Cell*, 68, 775–785 (Feb. 21, 1992).

Lincoff, et al., "Local Drug Delivery for the Prevention of Restenosis", *Circulation*, 90, 2070–2084 (Oct. 1994).

Linn, et al., "Microemulsion for the Intradermal Delivery of Cetyl Alcohol and Octyl Dimethyl Paba", *Drug Development and Industrial Pharmacy*, 16, 899–920 (1990).

Liu, M.D., et al., "Restenosis After Coronary Angioplasty—Potential Biologic Determinants and Role of Intimal Hyperplasia", *Circulation*, 79, 1374–87, (Jun. 1989).

Lopez–Casillas, et al., "Beta–glycan Presents Ligand to the TGFBeta Signaling Receptor", *Cell*, 73, 1435–1444, (Jul. 2, 1993).

Love, et al., "Effects of Tamoxifen on Cardiovascular Risk Factors in Postmenopausal Women.", *Annals of Internal Medicine*, 115, 860–864 (Dec. 1, 1991).

Love, et al., "Effects of Tamoxifen Therapy on Lipid and Lipoprotein Levels in Postmenopausal Patients with Node–Negative Breast Cancer", *J. Natl. Cancer Ins.*, 82, 1327–1332 (Aug. 15, 1990).

Luo, et al., "Chronic Vessel Constriction is an Important Mechanism of Restenosis After Balloon Angioplasty: An Intravascular Ultrasound Analysis", *Circulation*, 90, p. I61, Abstract No. 318 (1994).

Macander, et al., "Balloon Angioplasty for Treatment of In–Stent Restenosis: Feasibility, Safety, and Efficacy", *Catheterization and Cardiovascular Diagnosis*, 37, 125–131 (1990).

Magarian, "The Medicinal Chemistry of Nonsteroidal Anti-estrogens: A Review", *Current Medicinal Chemistry*, 1, 61–104, (1994).

Majack, R.A., et al., "Role of PDGF–A Expresion in the Control of Vascular Smooth Muscle Cell Growth by Transforming Growth Factor–B", *The Journal of Cell Biology*, vol. 111, pp. 239–247, (1990).

Majesky, M.W., et al., "Production of Transforming Growth Factor beta1 During Repair of Arterial Injury", *J. Clin. Invest.*, 88, 904–910, (1991).

Malcolmson, et al., "A Comparison Between Nonionic Micelles and Microemulsions as a Means of Incorporating the Poorly Water Soluble Drug Diazepam", *J. Pharm. Pharmacol*, 42, 6P (1990).

Marx, "CMV–p.53 Interaction May Help Explain Clogged Arteries", *Science*, 265, 320(Jul. 15, 1994).

Marzocchi, A. et al., "Restenosis After Coronary Angioplasty: Its Pathogenesis and Prevention", *Cardiologia,* 36, Translation, 309–320, (Dec., 1991).

Massague, "The transforming growth factor–B family", *Ann. Rev. Cell Biol.,* 6, 597–641 (1990).

McAuslan, B.R., et al., "Cellular and Molecular Mechanisms in Angiogenesis", *Trans. Ophthal. Soc. U.K.,* 100, 354–358, (1980).

McCaffrey, T.A., et al., "Fucoidan is a Non–Anticoagulant Inhibitor of Intimal Hyperplasia", *Biochemical and Biophysical Research Communications,* 184, 773–781, (Apr. 1992).

McCaffrey et al., "Transforming Growth Factor–Beta/Alpha2– Activity is Potentiated by Heparin via Dissociation of the Transforming Growth Factor–beta–macroglobulin Inactive Complex", *J. Cell. Biol.,* 109, 441–448, (1989).

Mccague, et al., "An Efficient, Large Scale Synthesis of Idoxifene ((E)–1(4–(2–(N–pyrrolidino)ethoxy)–1–(4–iodophenyl)–2–phenyl–1–butene)", *Organic Preparations and Proc. Int.,* 26, 343–346 (1994).

Mccague, et al., "Synthesis of 4–Stannylated Tamoxifen Analogues: Useful Precursors to Radiolabelled Idoxifene Axiridinyl 4–Iodotamoxifen.", *J. Labelled Compounds and Pharmaceuticals,* 34, 297–302 (1994).

Mccaroll, et al., "Preliminary Studies on the Regulation of Secretion of Latent Transforming Growth Factor–B (TGF–B) by Endothelial Cells in Culture.", *Clin. Chem.,* 36, p. 1152, Abstract No. 0934 (1990).

Mccormick, et al., "Retinoid–Tamoxifen Interaction in Mammary Cancer Chemoprevention", *Carcinogenesis,* 7, 193–196 (1986).

Mcdonald, et al., "Fatal Myocardial Infarction in the Scottish Adjuvant Tamoxifen Trial.", *B. Med. J.,* 303, 435–437 (Aug. 24, 1991).

Mclean, et al., "cDNA sequence of human apolipoprotein (a) is homologous to plasminogen", *Nature,* 330, 132–137 (1987).

Mcquiggan, J.D., "Tissue Distribution of Cytochalasin B After Intraperitoneal Bolus and Microencapsulated Injection in Mice and its Effect on B–N–Acetylglucosaminidase Activity in Cultured B16–BL6 Melanoma Cells", Masters' Thesis, University of Syracuse, New York (1983).

Merrilees, et al., "Synthesis of TGF–B1 by Vascular Endothelial Cells is Correlated with Cell Spreading.", *J. Vasc. Res.,* 29, 376–384 (1992).

Metcalfe, et al., "Protein Markers of Lesion Development in the Vessels of Transgenic Apo(a) Mice", Inflammation, Growth Regulatory Molecules & Atherosclerosis, *J. Cellular Biochem.,* Supplement 18A, p. 208, Abstract No. E212 (1994).

Metcalfe, J.C., et al., "Transforming Growth Factor–B and the Protection From Cardiovascular Injury Hypothesis", *Biochem. Soc. Trans.,* 23, 403–406, (1995).

Mintz, et al., "Chronic Compensatory arterial dilation following coronary angioplasty: an intravscular untrasound study", *JACC,* p. 138A, Abstract 875–97 (Feb. 1994).

Mintz, et al., "Geometric Remodeling is the Predominant Mechanism of Clinical Restenosis After Coronary Angioplasty.\", *JACC,* p. 138 A, Abstract No. 875–42 (Feb. 1994).

Mintz, et al., "Mechanisms of Late Aterial Response to Transcatheter Therapy: A Serial Quantitative Angiographic and Intravascular Ultrasound Study.\", *Circulation,* 90, p. I–24, Abstract No. 117 (Oct. 1994).

More, R.S., et al., "A Targeted Antithrobotic Conjugate with Antiplatelet and Fibrinolytic Properties which Reduces in vivo Thrombus Formation", *Cardiovasc. Res.,* 27, 2200–2204, (1993).

Morisaki, et al., "Effects of transforming growth factor–B, on growth of aortic smooth muscle cells", *Atherosclerosis,* 88, 227–234, (1991).

Mosedale, et al., "Transforming Growth Factor–beta is Correlated with Smooth Muscle Cell Differentiation in Vivo", *Circulation,* p. 90, p. I–296, Abstract No. 1590 (Oct. 1994).

Nakagawa et al., "A Case of Acute Myocardinal Infarction Intracoronary Arteries Due To Hormone Therapy.", *Angiology,* 45, 333–338 (1994).

Navaro, et al., "Notes from Transcatheter Cardiovascular Therapeutics 1995 Conference", *USB Securities, Medical Technol.,* (Mar. 3, 1995).

Nikol, S., et al., "Expression of Transforming Growth Factor Beta 1 is Increased in Human Vascular Restenosis Lesions", *J. Clin. Invest.,* 90, 1582–1592, (1992).

Nunes, et al., "Vitamins C and E Improve the Response to Coronary Balloon Insert in the Pig: Effect of Vascular Remodeling.", *Circulation,* 88, p. I–372, Abstract No. 1991 (Oct. 1993).

O'brien, et al., "Osteopontin mRNA and Protein are Overexposed in Human Coronary Atherectomy Specimens: Clues to Lesion and Calcification.", *Circulation,* 88, p. I–619, Abstract No. 3330 (1993).

O'connor–mccourt, et al., "Latent Transforming Growth Factor–B in Serum: A Specific Complex with a2–macroglobin", *J. Biol. Chem.* 262, 14090–14099 (Oct. 15, 1987).

Osborne, et al., "Microemulsions as Topical Drug Delivery Vehicles: In Vitro Trandermal Studies of a Model Hydrophilic Drug", *J. Pharm. Pharmacol.,* 43, 451–454 (1991).

Osipow, "Transparent Emulsion", *J. Soc. Cosmetic Chemists,* 277–285 (1963).

Owens, G.K., et al., "Transforming Growth Factor–B–induced Growth Inhibition and Cellular Hypertrophy in Cultured Vascular Smooth Muscle Cells", *The Journal of Cell Biology,* 107, 771–780, (Aug. 1988).

Ozer, et al., "New Roles of low density lipoproteins and vitamin E in the pathogenesis of atherosclerosis", *Biochem Mol. Biol. Intern,* 35, 117–124, (Jan. 1995).

Palmaz, J.C., et al., "Intravascular Stents", In: *Advances in Vascular Surgery,* vol. 1, Mosby–Year Book Inc.,, pp. 107–135, (1993).

Parthasarathy, S., et al., "A Role for Endothelial Cell Lipoxygenase in the Oxidative Modification of Low Density Lipoprotein", *Proc. Natl. Acad. Sci. USA,* 86, 1046–1050, (Feb. 1989).

Pathak, et al., "Enhanced Stability of Physostigmine Salicylate in Submicron o/w Emulsion", *International Journal of Pharmaceutics,* 65, 169–175(1990).

Perez, J.R., et al., "Regulation of Adhesion and Growth of Fibrosarcoma Cells by NF–kb RelA Involves Transforming Growth Factor Beta", *Molecular and Cellular Biology,* 14, 5326–5332, (Aug. 1994).

Podzimek, et al., "O/W Microemulsions", *J. Dispersion Science and Technology,* I, 341–359 (1980).

Popma, et al., "Factors Influencing Restenosis after Coronary Angioplasty.", *Am. J. of Med.,* 88, 1–16N–1–24N (Jan. 1990).

Post, et al., "Restenosis is Partly Due to Intimal Hyperplasia and Partly to Remodeling of the Injured Arterial Wall", *Eur. Heart J.*, p. 201, Abstract No. P1164 (1993).

Post, et al., "The Relative Importance of Arterial Remodeling Compared with Intimal Hyperplasia in Lumen Renarrowing After Balloon Angioplasty", *Circulation*, 89, 2816–2821 (Jun. 1994).

Post, et al., "Which Part of the Angiographic Diameter Reduction After Balloon Dilation is Due to Intimal Hyperplasia?", *JACC*, 21, p. 36A, Abstract No. 851–95 (Feb. 1993).

Potter, et al., "A Mechanism Hypothesis for DNA Adduct Formation Following Hepatic Oxidative Metabolism.", *Carcinogenesis*, 15, 439–442, (1994).

Pouton, C.W., "Self–Emulsifying Drug Delivery Systems: Assessment of the Efficiency of Emulsification", *International Journal of Pharmaceutics*, 27, 335–348, (1985).

Raloff, "Tamoxifen Puts Cancer on Starvation Diet", *Science News*, 146, 292, (Nov. 5, 1994).

Rauterberg, et al., "Collagens in Atherosclerotic Vessel Wall Lesions", *Current Topics in Pathology*, 87, 163–192(1993).

Reid et al., "Fragmentation of DNA in P388D1 Macrophages Exposed to Oxidized Low–Density Lipoprotein", *FEBS Letters*, 332, 218–220 (1993).

Reiner, Z., et al., "Antiestogen Tamoxifen Reduces Lipoprotein(a)", Abstracts, The Second International Conference on Lipoprotein (a), New Orleans, LA, p. 124, (Nov. 12–14, 1992).

Riessen, R., et al., "Prospects for Site–Specific Delivery of Pharmacologic and Molecular Therapies", *Journal of the American College of Cardiology*, 23, 1234–1244, (Apr. 1994).

Ross, R., et al., "Chronic Inflammation, PGF, TGFbeta, and Smooth Muscle Proliferation", *J. Cell. Biochem.*, S15C, Abstract No. H006, p. 142, (1991).

Rutsch, W., et al., "Benestent–II Pilot Study: 6 Months Follow Up of Phase 1", Abstract, Society of Cardiology, (1995).

Sagitani, et al., "Microemulsion Systems with a Nonionic Cosurfant", *J. Dispersion Science and Technology*, 1 (2), 151–164(1980).

Sanders, et al., "Controlled Release of a Lutenizing Hormone–Releasing Hormone Analogue from Poly(d,l–lactide–co–glycolide) Microspheres.", *J. Pharmaceutical Science*, 73, 1294–1297 (Sep. 1984).

Sanderson, et al., "Antibody–coated microspheres for drug delivery to prevent restenosis", *Circulation*, 90, p. I–508, Abstract No. 2734 (Oct. 1994).

Schatz, R.A., et al., "A View of Vascular Stents", *Circulation*, 79, 445–457, (Feb., 1989).

Schneiderman, et al., "Increased Type 1 Plasminogen Activator Inhibitor Gene Expression in Atherosclerotic Human Arteries.", *PNAS (USA)*, 89, 6998–7002 (Aug. 1992).

Schoenemanne, et al., "The Differential Diagnoses of Spontaneous Pneumothorax and Pulmonary Lymphangioleimyomatosis Clinical Picture Diagnoses and Theory.", *Chirag*, 61, 301–303 (1990) English Abstract only, reported in *Biosis*, 90, 432367 (1990).

Schwartz, et al., "Restenosis After Balloon Angioplasty–A Practical Proliferative Model in Porcine Coronary Arteries", *Circulation*, 82, 2190–2200 (Dec. 1990).

Schwartz, et al., "The Restenosis Paradigm Revisted: An Alternative Proposal for Cellular Mechanisms", *JACC*, 20, 1284–1293 (Nov. 1, 1992).

Sedlacek, S., "Estrogenic Properties of Tamoxifen on Serum Lipids in Postmenopausal Women with Breast Cancer (BCA)", *Breast Cancer Research and Treatment*, 14, Abstract No. 82, p. 153, (1989).

Serruys, P.W., et. al., "A Comparison of Balloon–Expandable–Stent Implantation with Balloon Angioplasty in Patients with Coronary Artery Disease", *The New England Journal of Medicine*, 331, 489–495, (Aug., 1994).

Shanahan, et al., "High Expression of Genes for Calcification–regulating Proteins in Human Atherosclerotic Plaques", *J. Clin. Invest.*, 93, 2393–2402 (Jun. 1994).

Shanahan, C.M., et al., "Isolation of gene markers of differentialted and proliferating vascular smooth muscle cells", *Circulation Res.*, 73, 193–204, (1993).

Shewmon, et al., "Tamoxifen and Estrogen Lower Circulating Lipoprotein(a) Concentrations in Healthy Postmenopausal Women", *Arteriosclerosis and Thrombosis*, 14, 1589–1593, (Oct., 1992).

Shewmon, et al., "Tamoxifen Decreases Lipoprotein (a) in Patients with Breast Cancer.", *Metabolism*, 43, 531–532 (May 1994).

Shewmon, D.A., et al., "Tamoxifen Lowers Lp(a) in Males with Heart Disease", *Supplement I Circulation*, 86, 1345, (Oct., 1992).

Shoji, et al., "Enhancement of Anti–Inflammatory Effects of Biphenylylactic Acid by its Incorporation into Lipid Microspheres.", *J. Pharm. Pharmacol*, 38, 118–121 (1986).

Siebenlist, U., et al., "Structure, Regulation and Function of NF–kB", *Annu. Rev. Cell. Biol.*, 10, 405–455, (1994).

Singh, et al., "Phylogenetic Analysis of Platelet–derived Growth Factor by Radio–Receptor Assay.", *J. Cell Biol.*, 95, 667–671 (Nov. 1982).

Sismondi, et al., "Metabolic Effects of Tamoxifen in Postmenopause.", *Anticancer Res.*, 14, 2237–2244 (1994).

Snow, A.D., et al., "Heparin Modulates the Composition of the Extracellular Matrix Domain Surrounding Arterial Smooth Muscle Cells", *Am. J. Path.*, 137, 313–330, (Aug. 1990).

Song, C., "Dexamethasine–nanoparticles for intra–arterial localization in restenosis in rats", Proceec. Intern. Symp. Control. Rel. Mater, 22, 444–445, (1995).

Speir, et al., "Potential Role of Human Cytomegalovirus and p53 Interaction in Coronary Restenosis", *Science*, 265, 391–394(Jul. 15, 1994).

Steele, P.M., et al., "Balloon Angioplasty—Nature History of the Pathophysiological Response to Injury in a Pig Model", *Circ. Res.*, 57, 105–112, (Jul. 1985).

Stouffer, et al., "TGF beta Has a Biphasic, Concentration Dependent Effect on EFG and PDGR–BB Induced Smooth Muscle Cell Proliferation, Inflammation, Growth Regulatory Molecules and Atherosclerosis.", *J. Cellular Biochem*, Supplement 18A, p. 288, Abstract No. A321 (1994).

Streuli, C.H., et al., "Extracellular Matrix Regulates Expression of the TGF–Beta 1 Gene", *J. Cell Biol.*, 120, 253–260, (Jan. 1993).

Suckling, "Atherosclerosis Patents: Clues to the Next Drug Generation", *Bio/Tech*, 12, 1379–1380, (Dec. 1994).

Suckling, "Emerging Strategies for the Treatment of Atherosclerosis as Seen from Patent Literature", *Biochem. Soc. Trans.*, 21, 660–662, (Mar. 1993).

Tanaka, et al., "Prominent Inhibitory Effects of Tranilast on Migration and Proliferation of and Collagen Synthesis by Vascular Smooth Muscle Cells.", *Atherosclerosis*, 107, 179–185 (1994).

Tice, et al., "Biodegradable controlled–release parental systems", *Pharmaceutical Technology,* 26–35 (Nov. 1984).

Topol, "The Restenosis Antitheory", *Mayo Clin. Proc.,* 68, 88–90 (Jan. 1993).

Vanhoutte, "Hypercholesterolaemia, Atherosclerosis and Release of Endothelium–Derived Relaxijng Factor by Aggregating Platelets", *Eur. Heart J.,* 12, Suppl. E, 25–32 (1991).

Vargas, et al., "Oestradiol Inhibits Smooth Muscle Cell Proliferation of Pig Coronary Artery.", *Br. J. Pharmacol.,* 109, 612–617 (1993).

Wakefield, et al., "Latent Transforming Growth Factor–B from Human Platelets: A High Molecular Weight Complex Containing Precursor Sequences.", *J. Biol. Chem.,* 263, 7646–7654 (Jun. 5, 1988).

Wakefield, et al., "Recombinant Latent Transforming Growth Factor–B, has a Longer Plasma Half–Line in Rats thatn Active Transforming Growth Factor–B, and a Different Tissue Distribution.", *J. Clin. Invest.,* 86, 1976–1984 (Dec. 1990).

Watson, et al., "TGF–B1 and 25–Hydroxcholesterol Stimulate Osteoblast–Like Vascular Cells to Calcify", *J. Clin. Invest.,* vol. 93, 2106–2113, (May 1994).

Weissberg, et al., "The Endothelium Peptides ET–1, ET–2, ET–3 and Sarafotoxin Sob are Comitogenic with Platelet Derived Growth Factor for Vascular Smoth Muscle Cells.", *Atherosclerosis,* 85, 257–262 (1990).

Weissberg, P.L., et al., "Approaches to the Development of Selective Inhibitors of Vascular Smooth Muscle Cell Proliferation", *Cardiovascular Res.,* 27, 1191–1198.

Weissberg, P.L., et al., "Effects of TGF–Beta on Vascular Smooth Muscle Cell Growth", *Growth Factors and the Cardiovascular System,* Cummins, P. (ed.), Kluward Academic Publishers, 189–205, (1993).

Weissberg, P.L., et al., "Is Vascular Smooth Muscle Cell Proliferation Beneficial?", *Lancet,* 347, 305–307, (1996).

Wilensky, R.L., et al., "Direct Intraarterial Wall Injection of Microparticles via a Catheter: A Potential Drug Delivery Strategy Following Angioplasty", *American Heart Journal,* 122, 1136–1140, (Oct., 1991).

Wiseman, H., "Tamoxifen as an Antioxidant and Cardioprotectant", *Biochem. Soc. Symp.,* 61, 209–219, (1995).

Wolf et al., "Antibodies Against Transforming Growth Factor–B1 Suppress Intimal Hyperplasia in a Rat Model", *J. Clin. Invest.,* 93, 1172–1178 (1994).

Wolinsky, et al., "Use of a Perforated Balloon Catheter to Deliver Concentrated Heparin Into the Wall of the Normal Canine Artery.", *JACC,* 15, 475–481 (Feb. 1990).

Wrana, et al., "Mechanism of Actuation of the TGF–B Receptor", *Nature,* 370, 341–347, (Aug. 4, 1994).

Yang, N.N., et al., "Estrogen Receptor: One Transcription Factor, Two Genomic Pathways", *Calcified Tissue Intl.,* 54, 342, (1994).

Young, H., et al., "Pharmacokinetics and Biodistribution of Radiolabelled Idoxifene: Prospects for the Use of PET in the Evaluation of a Novel Antioestrogen for Cancer Therapy", *Nucl. Med. Biol.,* 22, 405–411, (May 1995).

Zuckerman, et al., "Cytokine Regulation of Macrophage apo E. Secretion: Opposing Effects of GM–CSF and TGF–B.", *Atherosclerosis,* 96, 203–214 (1992).

Zuckerman, et al., "Exogenous Glucocorticoids Increase Macrophage Section of apo E by Cholesterol Independent Pathways.", *Atherosclerosis,* 103, 43–54 (1993).

PREVENTION AND TREATMENT OF CARDIOVASCULAR PATHOLOGIES

RELATED APPLICATIONS

This application is a continuation of U.S. Ser. No. 09/082,643, filed May 21, 1998, which is a division of U.S. Ser. No. 08/486,334, filed Jun. 7, 1995, now U.S. Pat. No. 5,770,609, which is a continuation-in-part of U.S. Ser. No. 08/242,161, filed May 12, 1994, now U.S. Pat. No. 5,847,007, which is a continuation-in-part of U.S. Ser. No. 08/061,714, filed May 13, 1993, now abandoned and a continuation-in-part of U.S. Ser. No. 08/241,844, filed May 12, 1994, now abandoned, which is a continuation-in-part of U.S. Ser. No. 08/062,451, filed May 13, 1993, now abandoned, which is a continuation-in-part of U.S. Ser. No. 08/011,669, filed Jan. 28, 1993, now abandoned, which is a continuation-in-part of PCT/US92/08220, filed Sep. 25, 1992, which are incorporated by reference herein.

FIELD OF THE INVENTION

This invention relates generally to the prevention and treatment of cardiovascular pathologies. More specifically, a method for treating or preventing atherosclerosis is provided.

BACKGROUND OF THE INVENTION

Many pathological conditions have been found to be associated with smooth muscle cell proliferation. Such conditions include restenosis, atherosclerosis, coronary heart disease, thrombosis, myocardial infarction, stroke, smooth muscle neoplasms such as leiomyoma and leiomyosarcoma of the bowel and uterus, uterine fibroid or fibroma, and obliterative disease of vascular grafts and transplanted organs. The mechanisms of abnormal smooth muscle cell proliferation are not yet well understood.

For example, percutaneous transluminal coronary angioplasty (PTCA) is widely used as the primary treatment modality in many patients with coronary artery disease. PTCA can relieve myocardial ischemia in patients with coronary artery disease by reducing lumen obstruction and improving coronary flow. The use of this surgical procedure has grown rapidly, with 39,000 procedures performed in 1983, nearly 150,000 in 1987, 200,000 in 1988, 250,000 in 1989, and over 500,000 PTCAs per year are estimated by 1994. Stenosis following FICA remains a significant problem, with from 25% to 35% of the patients developing restenosis within 1 to 3 months. Restenosis results in significant morbidity and mortality and frequently necessitates further interventions such as repeat angioplasty or coronary bypass surgery. No surgical intervention or post-surgical treatment (to date) has proven effective in preventing restenosis.

The processes responsible for stenosis after PTCA are not completely understood but may result from a complex interplay among several different biologic agents and pathways. Viewed in histological sections, restenotic lesions may have an overgrowth of smooth muscle cells in the intimal layers of the vessel. Several possible mechanisms for smooth muscle cell proliferation after PTCA have been suggested. For example, Barath et al. (U. S. Pat. No. 5,242,397) disclose delivering cytotoxic doses of protein kinase C inhibitors, including tamoxifen, locally by catheter to the site of the atherosclerotic lesion.

Compounds that reportedly suppress smooth muscle proieration in vitro may have undesirable pharmacological side effects when used in vivo. Heparin is an example of one such compound, which reportedly inhibits smooth muscle cell proliferation in vitro but when used in vivo has the potential adverse side effect of inhibiting coagulation. Low molecular weight fragments of heparin, while having reduced anti-coagulant activity, have the undesirable pharmacological property of a short pharmacological half-life. Attempts have been made to solve such problems by using a double balloon catheter, i.e., for regional delivery of the therapeutic agent at the angioplasty site (e.g., U.S. Pat. No. 4,824,436), and by using biodegradable materials impregnated with a drug, i.e., to compensate for problems of short half-life (e.g., U.S. Pat. No. 4,929,602).

In general, atherosclerosis is a cardiovascular disease in which the vessel wall is remodeled, compromising the lumen of the vessel. The atherosclerotic remodeling process involves accumulation of cells, both smooth muscle cells and monocyte/macrophage inflammatory cells, in the intima of the vessel wall. These cells take up lipid, likely from the circulation, to form a mature atherosclerotic lesion. Although the formation of these lesions is a chronic process, occurring over decades of an adult human life, the majority of the morbidity associated with atherosclerosis occurs when a lesion ruptures, releasing thrombogenic debris that rapidly occludes the artery. When such an acute event occurs in the coronary artery, myocardial infarction can ensue, and in the worst case, can result in death.

The formation of the atherosclerotic lesion can be considered to occur in five overlapping stages such as migration, lipid accumulation, recruitment of inflammatory cells, proliferation of vascular smooth muscle cells, and extracellular matrix deposition. Each of these processes can be shown to occur in man and in animal models of atherosclerosis, but the relative contribution of each to the pathology and clinical significance of the lesion is unclear.

Thus, a need exists for therapeutic methods and agents to treat cardiovascular pathologies, such as atherosclerosis and other conditions related to coronary artery disease.

SUMMARY OF THE INVENTION

A therapeutic method for preventing or treating a cardiovascular indication characterized by a decreased lumen diameter is provided. The method comprises administering to a mammal at risk of, or afflicted with, said cardiovascular indication, a cytostatic dose of a TGF-beta activator or production -stimulator. The cytostatic dose is effective to activate or stimulate production of TGF-beta and the effective amount inhibits smooth muscle cell proliferation, inhibits lipid accumulation, increases plaque stability, or any combination thereof.

A therapeutic method is provided for treating or preventing cardiovascular pathologies, such as conditions selected from the group consisting of atherosclerosis, thrombosis, myocardial infarction, and stroke. The method comprises the systemic or local administration of an amount of a compound of formula (I)

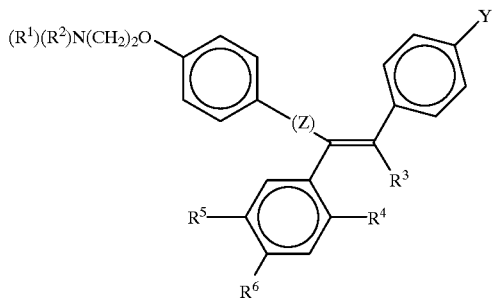

(I)

wherein Z is C=O or a covalent bond; Y is H or O($C_1$–$C_4$) alkyl, $R^1$ and $R^2$ are individually ($C_1$–$C_4$)alkyl or together with N are a saturated heterocyclic group, $R^3$ is ethyl or chloroethyl, $R^4$ is H or together with $R^3$ is —$CH_2$—$CH_2$— or —S—, $R^5$ is I, O($C_1$–$C_4$)alkyl or H and $R^6$ is I, O($C_1$–$C_4$) alkyl or H with the proviso that when $R^4$, $R^5$, and $R^6$ are H, $R^3$ is not ethyl; or a pharmaceutically acceptable salt, including mixtures thereof, effective to activate or stimulate production of TGF-beta in a mammal afflicted with one of these conditions. Thus, in this embodiment of the invention, the compound of formula (I) does not include tamoxifen.

The administered compound of formula (I) can act on vascular smooth muscle cells (VSMC) to inhibit the pathological activity of these smooth muscle cells and can inhibit lipid proliferative lesions. Preferably, the compound significantly reduces the rate of completion of the cell cycle and cell division, and preferably is administered at cytostatic, as opposed to cytotoxic, doses. A preferred embodiment of the invention comprises treatment of atherosclerosis, wherein the compound of formula (I), such as idoxifene or idoxifene salt, inhibits lipid accumulation by vascular smooth muscle cells and/or stabilizes an arterial lesion associated with atherosclerosis, i.e., increases plaque stability, to prevent rupture or growth of the lesion. As exemplified hereinbelow, orally administered tamoxifen significantly inhibits the formation of lipid lesions, induced by a high fat diet, in C57B16 mice and in the transgenic apo(a) mouse. The 90% reduction in lesion area and number in both of these mouse models indicates that tamoxifen affects the accumulation of lipid in the cells and stroma of the vessel wall. The inhibition of lipid accumulation and lesion development in these treated mice indicates that tamoxifen and analogs thereof, as well as compounds of formula (I), may inhibit the development of atherosclerotic lesions in humans by inhibiting lipid accumulation, in addition to decreasing smooth muscle cell proliferation.

Other preferred embodiments of the invention comprise the local administration of the compound of formula (I) to an arterial lesion associated with atherosclerosis, and a kit to accomplish said administration.

A further embodiment of the invention is a method for preventing cardiovascular pathologies in a mammal at risk of such a condition. Such conditions include atherosclerosis, thrombosis, myocardial infarction, and stroke. The method comprises the administration of an amount of the compound of formula (I) to a mammal, such as a human, effective to activate or stimulate production of TGF-beta. The amount of the compound is administered over time as a preventative measure. Preferably, the compound is administered orally, in a series of spaced doses.

A further embodiment of the invention is a method for inhibiting smooth muscle cell (SMC) proliferation associated with procedural vascular trauma as by the systemic or localized catheter or non-catheter administration to a mammal, such as a human patient, subjected to said procedure, an effective cytostatic SMC proliferation inhibitory amount of tamoxifen (TMX), a compound of formula (I), a combination thereof, or a pharmaceutically acceptable salt thereof. The systemic administration can be accomplished by oral or parenteral administration of one of more suitable unit dosage forms, which, as discussed below, may be formulated for sustained release. The administration may be essentially continuous over a preselected period of time or may be in a series of spaced doses, either before, during, or after the procedural vascular trauma, or both before and after the procedural trauma, including during the procedure causing the trauma.

As used herein, the term "procedural vascular trauma" includes the effects of surgical/mechanical interventions into mammalian vasculature, but does not include vascular trauma due to the organic vascular pathologies listed hereinabove.

Thus, procedural vascular traumas within the scope of the present treatment method include (1) organ transplantation, such as heart, kidney, liver and the like, e.g., involving vessel anastomosis; (2) vascular surgery, such as coronary bypass surgery, biopsy, heart valve replacement, atheroectomy, thrombectomy, and the like; (3) transcatheter vascular therapies (TVT) including angioplasty, e.g., laser angioplasty and PTCA procedures discussed hereinbelow, employing balloon catheters, and indwelling catheters; (4) vascular grafting using natural or synthetic materials, such as in saphenous vein coronary bypass grafts, dacron and venous grafts used for peripheral arterial reconstruction, etc.; (5) placement of a mechanical shunt, such as a PIFE hemodialysis shunt used for arteriovenous communications; and (6) placement of an intravascular stent, which may be metallic, plastic or a biodegradable polymer. See U.S. patent application Ser. No. 08/389,712, filed Feb. 15, 1995, which is incorporated by reference herein. For a general discussion of implantable devices and biomaterials from which they can be formed, see H. Kambic et al., "Biomatedals in Artificial Organs", *Chem. Eng. News.* 30 (Apr. 14, 1986), the disclosure of which is incorporated by reference herein.

In the case of organ transplantation, the entire organ, or a portion thereof, may be infused with a solution of TMX and/or the compound of formula (I), prior to implantation. Likewise, in vascular surgery, the termini of the vessels subject to anastomosis can be infused with TMX and/or the compound of formula (I), or the antiproliferative agents can be delivered from pretreated sutures or staples.

The delivery of TGF-beta activators or production stimulators to the lumen of a vessel via catheter, before, during or after angioplasty, is discussed in detail below. A stent or shunt useful in the present method can comprise a biodegradable coating or porous non-biodegradable coating, having dispersed therein the sustained-release dosage form. In the alternative embodiment, a biodegradable stent or shunt may also have the therapeutic agent impregnated therein, i.e., in the stent or shunt matrix. Utilization of a biodegradable stent or shunt with the therapeutic agent impregnated therein is further coated with a biodegradable coating or with a porous non-biodegradable coating having the sustained release-dosage form dispersed therein is also contemplated. This embodiment of the invention would provide a differential release rate of the therapeutic agent, i.e., there would be a faster release of the therapeutic agent from the coating followed by delayed release of the therapeutic agent that was impregnated in the stent or shunt matrix upon degradation of the stent or shunt matrix. The intravascular stent or shunt thus provides a mechanical means of maintaining or providing an increase in luminal area of a vessel and the antiproliferative agent inhibits the VSMC proliferative response induced by the stent or shunt, which can cause occlusion of blood flow and coronary failure.

For local administration during grafting, the ex vivo infusion of the antiproliferative agent into the excised vessels (arteries or veins) to be used for vascular grafts can be accomplished. In this aspect of the invention, the vessel that is to serve as the graft is excised or isolated and subsequently distended by an infusion of a solution of the therapeutic agent, preferably by pressure infusion. Of course, grafts of synthetic fiber can be precoated with TMX and/or compounds of formula (I) prior to in vivo placement.

A further aspect of the invention is a method comprising inhibiting vascular smooth muscle cell proliferation associated with procedural vascular trauma due to organ transplantation, vascular surgery, angioplasty, shunt placement, stent placement or vascular grafting comprising administration to a mammal, such as a human, subjected to said procedural trauma an effective antiproliferative amount of a compound of formula (I) or a pharmaceutically acceptable salt thereof. Administration may be systemic, as by oral or parenteral administration, or local, as to the site of the vascular trauma, or both.

Yet a further aspect of the invention provides a method comprising inhibiting non-aortal vascular smooth muscle cell proliferation associated with procedural vascular trauma comprising administering an effective cytostatic antiproliferative amount of tamoxifen or a structural analog thereof, including the pharmaceutically acceptable salts thereof, to a mammal, such as a human, subjected to said procedural vascular trauma. Said administration can be systemic or by local, catheter or non-catheter delivery to the site of the trauma.

Also provided is a kit comprising packing material enclosing, separately packaged, a catheter, a stent, a shunt or a synthetic graft and a unit dosage form of an amount of a compound of formula (I) and/or tamoxifen effective to accomplish these therapeutic results when delivered locally, as well as instruction means for its use, in accord with the present methods.

Another embodiment of the present invention is a method for identifying a compound which is a TGF-beta activator or production stimulator. Human vascular smooth muscle cells (hVSMC) are cultured with an amount of the compound effective to reduce the normal rate of hVSMC proliferation, due to TGF-beta activation or production stimulation by said compound. Then the hVSMC are contacted with an amount of an antibody which neutralizes TGF-beta activity. The method can also include the culture of rat aortic vascular smooth muscle cells (rVSMC) with an amount of the same compound effective to reduce the normal rate of proliferation of rVSMC, due to TGF-beta activation or production stimulation by said compound. The rVSMC are then contacted with the neutralizing antibody. The restoration of a normal rate of proliferation in treated rVSMC and treated hVSMC after contact with the TGF-beta neutralizing antibody indicates that the reduction of proliferation is due to TGF-beta activation or production stimulation in rVSMC and hVSMC by said compound, and suggests that hVSMC would be amenable to treatment by the administration of said compound in vivo.

Useful compounds of formula (I) are TGF-beta activators and TGF-beta production stimulators. These compounds, including their salts and mixtures thereof, may be employed in the practice of the present invention to prevent or treat other conditions characterized by inappropriate or pathological activity of vascular smooth muscle cells. Such TGF-beta activators and production stimulators inhibit abnormal activity of vascular smooth muscle cells. Preferred compounds of formula (I) include those wherein Z is a covalent bond, Y is H, $R^3$ is $ClCH_2CH_2$ or ethyl, $R^5$ or $R^6$ is iodo, $R^4$ is H or with $R^3$ is —$CH_2CH_2$— or —S—, $R^1$ and $R^2$ are each $CH_3$ or together with N are pyrrolidino, hexamethyleneimino or piperdino. These compounds can include structural analogs of tamoxifen (including derivatives of TMX and derivatives of said analogs) having equivalent bioactivity. Such analogs include idoxifene (IDX)(E-1-[4-[2-N-pyrrolidino)ethoxy]phenyl]-4 iodophenyl)-2-phenyl-1-butene), raloxifene, 3-iodotamoxifen, 4iodotamoxifen, tomremifene, and the pharmaceutically acceptable salts thereof.

Also provided are a method and a kit to determine the presence and amount of TGF-beta in a sample containing TGF-beta. The method for the determination of TGF-beta in vitro can be used to identify a patient at risk for atherosclerosis and/or monitor a recipient that has received one or more administrations of a TGF-beta activator or production stimulator. Blood serum or plasma from a patient or recipient is contacted with a capture moiety to form a capture complex of said capture moiety and TGF-beta. Preferably, the capture moiety is an immobilized capture moiety. The capture complex is then contacted with a detection moiety capable of binding TGF-beta comprising a detectable label, or a binding site for a detectable label, to form a detectable complex. The presence and amount, or absence, of the detectable complex is then determined, thereby determining the presence and amount, or absence, of TGF-beta in the blood of the patient or recipient.

A test kit for determining TGF-beta in vitro includes packaging material enclosing (a) a capture moiety capable of binding TGF-beta, and (b) a detection moiety capable of binding to TGF-beta, where the detection moiety has a detectable label or a binding site for a detectable label. The capture moiety and the detection moiety are separately packaged in the test kit. Preferably, the capture moiety is solid substrate-immobilized. Preferably, the capture moiety is the TGF-beta type II receptor extracellular domain. More preferably, the TGF-beta type II receptor extracellular domain is derived from a bacterial expression system. The kit can also comprise instruction means for correlation of the detection or determination of TGF-beta with the identification of the patients or monitoring discussed above.

Further provided is a method for upregulating cellular mRNA coding for TGF-beta. Cells (e.g., smooth muscle cells) amenable to such manipulation of mRNA accumulation are identified in the manner described herein and are exposed to an effective amount of a TGF-beta mRNA regulator (i.e., a subset of TGF-beta production stimulators), either free or in a sustained-release dosage form. In this manner, TGF-beta production is stimulated.

In addition, methods for using TGF-beta to maintain and increase vessel lumen diameter in a diseased or injured mammalian vessel are described.

DETAILED DESCRIPTION OF THE INVENTION

Figure 1:
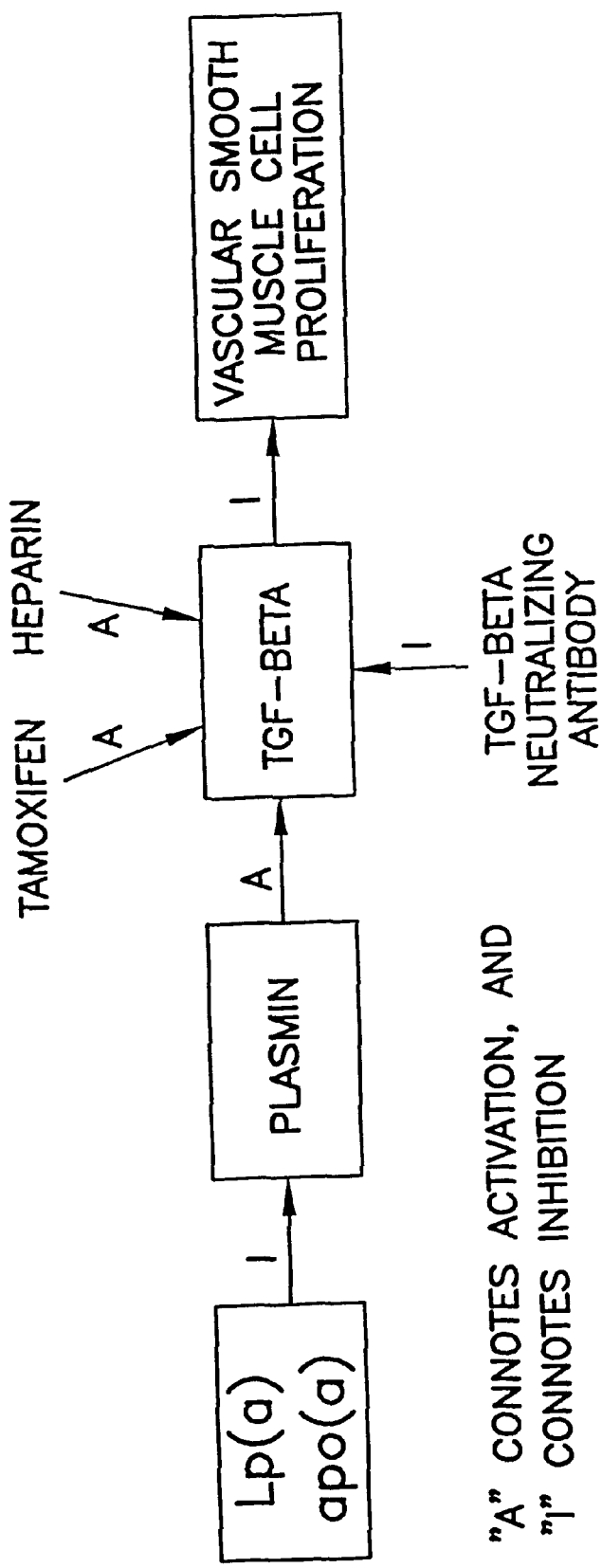
FIGS. 1 and 2 depict pathways for the modulation of vascular smooth muscle cell proliferation in vivo.

As used herein the following terms have the meanings as set forth below:

"Proliferation," means an increase in cell number, i.e., by mitosis of the cells.

"Abnormal or Pathological or Inappropriate Activity or Proliferation" means division, growth or migration of cells occurring more rapidly or to a significantly greater extent than typically occurs in a normally functioning cell of the same type, or in lesions not found in healthy tissues.

"Expressed" means mRNA trascription and translation with resultant synthesis, glycosylation, and/or secretion of a polypeptide by a cell, e.g., chondroitin sulfate proteoglycan (CSPG) synthesized by a vascular smooth muscle cell or pericyte.

The term "tamoxifen", as used herein, includes trans-2-[4(1,2diphenyl-1-butenyl)phenoxy]-N,N dimethylethylamine, and the pharmaceutically acceptable salts thereof, which are capable of enhancing the production or activation of TGF-beta. The activated form of TGF-beta, in turn, inhibits vascular smooth muscle cell activity. Isomers and derivatives of the aforementioned chemical compound are also included within the scope of the term "tamoxifen" for the purposes of this disclosure.

The term "structural analogs thereof" with respect to tamoxifen includes, but is not limited to, all of the compounds of formula (I) which are capable of enhancing production or activation of TGF-beta. See, for example, U.S. Pat. No. 4,536,516, and U.K. Patent 1,064,629.

Because tamoxifen I causes liver carcinogenicity in rats and has been correlated with an increased risk of endometrial cancer in women and may increase the risk of certain gut cancers, other tamoxifen analogs may be considered safer to administer if they are less carcinogenic. The carcinogenicity of TMX has been attributed to the formation of covalent DNA adducts. Of the TMX analogs and derivatives, only TMX and toremifene have been studied for long-term carcinogenicity in rats and these studies provide strong evidence that covalent DNA adducts are involved in rodent hepatocarcinogenicity of TMX. Toremifene, which exhibits only a very low level of hepatic DNA adducts, was found to be non-carcinogenic. See Potter et al., *Carcinogenesis*, 15, 439 (1994).

It is postulated that 4-hydroxylation of TMX yields electrophilic alkylating agents which alkylate DNA through the ethyl group of TMX. This mechanistic hypothesis explains the low level of DNA adduct formation by the non-TMX analogs of formula (I), including the TMX analog toremifene and the absence of DNA adducts detected for the analogs 4-iodotamoxifen and idoxifene. Thus, all of these analogs are likely to be free from the risk of carcinogenesis in long term use. See Potter et al., supra. Idoxifene includes (E)-1-[4-[2-(N-pyrrolidino)ethoxy]phenyl]-1-(4-iodophenyl)-2-phenyl-1-butene and its pharmaceutically acceptable salts and derivatives. See R McCague et al., *Organic Preparations and Procedures Int.*, 26, 343 (1994) and S. K. Chandler et al., *Cancer Res.*, 51, 5851 (1991). Besides its lower potential for inducing carcinogenesis via formation of DNA adducts which can damage DNA, other advantages of IDX compared with TMX are that IDX has reduced residual-oestrogenic activity in rats and an improved metabolic profile. IDX is the preferred embodiment of the present invention.

Also included within the scope of the term tamoxifen are the TMX structural analogs toremifene and raloxifene, metabolites or pharmaceutically acceptable salts thereof. Other "antisteroids" or "steroidal antagonists" can also be useful as TGF-beta activators or production stimulators or lead compounds, including other known stilbene-type antisteroids including cis- and trans-clomiphene, droloxifene, (1-[4(2dimethylaminoethoxy)phenyl]-1-(3-hydroxyphenyl)-2-phenyl-2-butene (see U.S. Pat. No. 5,384,332), 1-nitro-1-phenyl-2-(4-hydroxyphenyl or anisyl)-2-[4-(2-pyrrol-N-ylethoxy)-phenyl]ethylene(CN-55,945),trans-1,2-dimethyl-1,2-(4-hydroxyphenyl)ethylene(trans-dimethylstilboestrol), trans-diethylstilboestrol, and 1-nitro-1-phenyl-2-(4hydroxyphenyl)-2-[4(3-dimethylaminopropyloxy)phenyl ethylene (GI680).

Known 1,2diphenylethane-type antisteroids include cis-1,2-anisyl-1-[4-(2-diethylaminoethoxy)phenyl]ethane (MRL-37), 1-(4-chlorophenyl) 1-[4-(2-diethylaminoethoxy)phenyl]-2-phenylethanol (WSM-4613); 1-phenyl-1[4-(2-diethylaminoethoxy)phenyl]-2-anisylethanol (MER-25); 1-phenyl-1-[4-(2-diethylaminoethoxy)phenyl)-2-anisyl-ethane, mesobutoestrol (trans-1,2-dimethyl-1,2-(4-hydroxyphenyl)-ethane), meso-hexestrol, (+)hexestrol and (−)-hexestrol.

Known naphthalene-type antisteroids include nafoxidine, 1-[4-(2,3-dihydroxypropoxy)phenyl]-2-phenyl-6-hydroxy-1,2,3,4-tetrahydrohthalene, 1-(4-hydroxyphenyl)2-phenylhydroxy-1,2,3,4tetrhydronaphthalene, 1-t4M(2-pyol-N-ylethoxy)-phenyl]-2-phenylmethoxy-3, diydronaphthalene (U11, 100A), and 1-[4 (2,3 (hydroxypropoxy)phenyl]-2-phenyl-6methoxy-3, 4dihydronaphthalene(U-23, 469).

Known antisteroids which do not fall anywhere within these structural classifications include coumetstrol, biochanin-A, genistein, methallenstril, phenocyctin, and 1-[4(2-dimethylaminoethoxy)phenyl]-2-phenyl-5-methoxyindene (U, 11555). In the nomenclature employed hereinabove, the term "anisyl" is intended to refer to a 4methoxyphenyl group.

The pharmaceutically acceptable inorganic and organic acid amine salts of the amino group-containing antisteroids are also included within the scope of the term "antisteroid", as used herein, and include citrates, tartrates, acetates, hydrochlorides, hydrosulfates and the like.

"TGF-beta" includes transforming growth factor-beta as well as functional equivalents, derivatives and analogs thereof. The TGF-beta isoforms are a family of multifunctional, disulfide-linked dimeric polypeptides that affect activity, proliferation and differentiation of various cells types. TGF-beta is a polypeptide produced in a latent propeptide form having, at this time, no identified biological activity. To be rendered active and, therefore, capable of inhibiting vascular smooth muscle cell proliferation, the propeptide form of TGF-beta must be cleaved to yield active TGF-beta.

"TGF-beta activator" includes moieties capable of directly or indirectly activating the latent form of TGF-beta to the active form thereof. A number of the compounds of formula (I) are believed to be TGF-beta activators.

"TGF-beta production stimulator" includes moieties capable of directly or indirectly stimulating the production of TGF-beta (generally the latent form thereof). Such TGF-beta production stimulators may be TGF-beta mRNA regulators (i.e., moieties that increase the production of TGF-beta mRNA), enhancers of TGF-beta mRNA expression or the like.

"Direct" action implies that the TGF-beta activator acts on the latent form of TGF-beta. Such direct action, when applied to TGF-beta production stimulators, indicates that cells upon which the production stimulator acts increase TGF-beta mr,NA production or exprzssion of TGF-beta.

"Indirect" action implies that the TGF-beta activator acts on a moiety that itself or through one or more other moieties acts on latent TGF-beta. Such indirect action, when applied to TGF-beta production stimulators, indicates that the stimulators act on a moiety that itself or through one or more other moieties acts on a population of cells to stimulate the production of TGF-beta mRNA or the expression of TGF-beta.

"Sustained release" means a dosage form designed to release a therapeutic agent therefrom for a time period ranging from about 3 to about 21 days. Release over a longer time period is also contemplated as a "sustained release" dosage form of the present invention.

For the purposes of this description, the prototypical cells, upon which the effects of TGF-beta activators or production stimulators are felt, are smooth muscle cells and percytes derived from the medial layers of vessels which proliferate in intimal hyperplastic vascular sites following injury, such as that caused during PTCA. TGF-beta activators and production stimulators are not restricted in use for therapy following angioplasty; rather, the usefulness thereof will be proscribed by their ability to inhibit abnormal cellular proliferation, for example, of smooth muscle cells and pericytes in the vascular wall. Thus, other aspects of the invention include TGF-beta activators or production stimulators used in early therapeutic intervention for reducing, delaying, or eliminating (and even reversing) atherosclerotic plaque formation and areas of vascular wall hypertrophy and/or hyperplasia TGF-beta activators and production stimulators also find utility for early intervention in pre-atherosclerotic conditions, e.g., they are useful in patients at a high risk of developing atherosclerosis or with signs of hypertension resulting from atherosclerotic changes in vessels or vessel stenosis due to hypertrophy of the vessel wall.

TGF-beta activators or production stimulators of the invention are useful for inhibiting the pathological proliferation of vascular smooth muscle cells, e.g., for reducing, delaying, or eliminating stenosis following angioplasty. As used herein the term "reducing" means decreasing the intimal thickening that results from stimulation of smooth muscle cell proliferation following angioplasty, either in an animal model or in man. "Delaying" means delaying the time until onset of visible intimal hyperplasia (e.g., observed histologically or by angiographic examination) following angioplasty and may also be accompanied by "reduced" restenosis. "Eliminating" restenosis following angioplasty means completely "reducing" intimal thickening and/or completely "delaying" intimal hyperplasia in a patient to an extent which makes it no longer necessary to surgically intervene, i.e., to reestablish a suitable blood flow through the vessel by repeat angioplasty, atheroectomy, or coronary artery bypass surgery. The effects of reducing, delaying, or eliminating stenosis may be determined by methods routine to those skilled in the art including, but not limited to, angiography, ultrasonic evaluation, fluoroscopic imaging, fiber optic endoscopic examination or biopsy and histology.

The amount of TGF-beta activator or production stimulator administered is selected to treat vascular trauma of differing severity, with smaller doses being sufficient to treat lesser vascular trauma such as in the prevention of vascular rejection following graft or transplant. TGF-beta activators or production stimulators that are not characterized by an undesirable systemic toxicity profile at a prophylactic dose are also amenable to chronic use for prophylactic purposes with respect to disease states involving proliferation of vascular smooth muscle cells over time (e.g., atherosclerosis, coronary heart disease, thrombosis, myocardial infarction, stroke, smooth muscle neoplasms such as leiomyoma and leiomyosarcoma of the bowel and uterus, uterine fibroid or fibroma and the like), preferably via systemic administration.

For prevention of restenosis, a series of spaced doses, optionally, in sustained release dosage form, is preferably administered before and after the traumatic procedure (e.g., angioplasty). The dose may also be delivered locally, via catheter delivered to the afflicted vessel during the procedure. After the traumatic procedure is conducted, a series of follow-up doses are administered over time, preferably in a sustained release dosage form, systemically to maintain an anti-proliferative effect for a time sufficient to substantially reduce the risk of or to prevent restenosis. A preferred therapeutic protocol duration after angioplasty for this purpose is from about 3 to about 26 weeks.

High levels of lipoprotein Lp(a) are known to constitute a substantial risk factor for atherosclerosis, coronary heart disease and stroke. One symptom associated with such conditions and other problems, such as restenosis following balloon angioplasty and other pathogenic conditions, is the proliferation or the migration of smooth muscle cells. No direct link between Lp(a) and proliferation of vascular smooth muscle cells had been established in the prior art.

An in vivo pathway for the modulation of vascular smooth muscle cell proliferation is shown in FIG. 1. TGF-beta is believed to contribute to the inhibitory mechanism that maintains vascular smooth muscle cells in a non-proliferative state in healthy vessels.

Vascular smooth muscle cell proliferation is inhibited by an active form of TGF-beta. Tamoxifen has been shown by the experimentation detailed in Example 1 hereof to stimulate both the production and the activation of TGF-beta. Heparin stimulates the activation of TGF-beta by affecting the release of the active form of TGF-beta from inactive complexes present in serum. TGF-beta neutralizing antibodies inhibit the activity of TGF-beta, thereby facilitating the proliferation of vascular smooth muscle cells. An apparent in vivo physiological regulator of the activation of TGF-beta is plasmin. Plasmin is derived from plasminogen through activation by, for example, TPA (tissue plasminogen activator). Plasmin activity is inhibited by the lipoprotein Lp(a) or apolipoprotein(a) (apo(a)), thereby decreasing the activation of the latent form of TGF-beta and facilitating proliferation of vascular smooth muscle cells.

Figure 2:
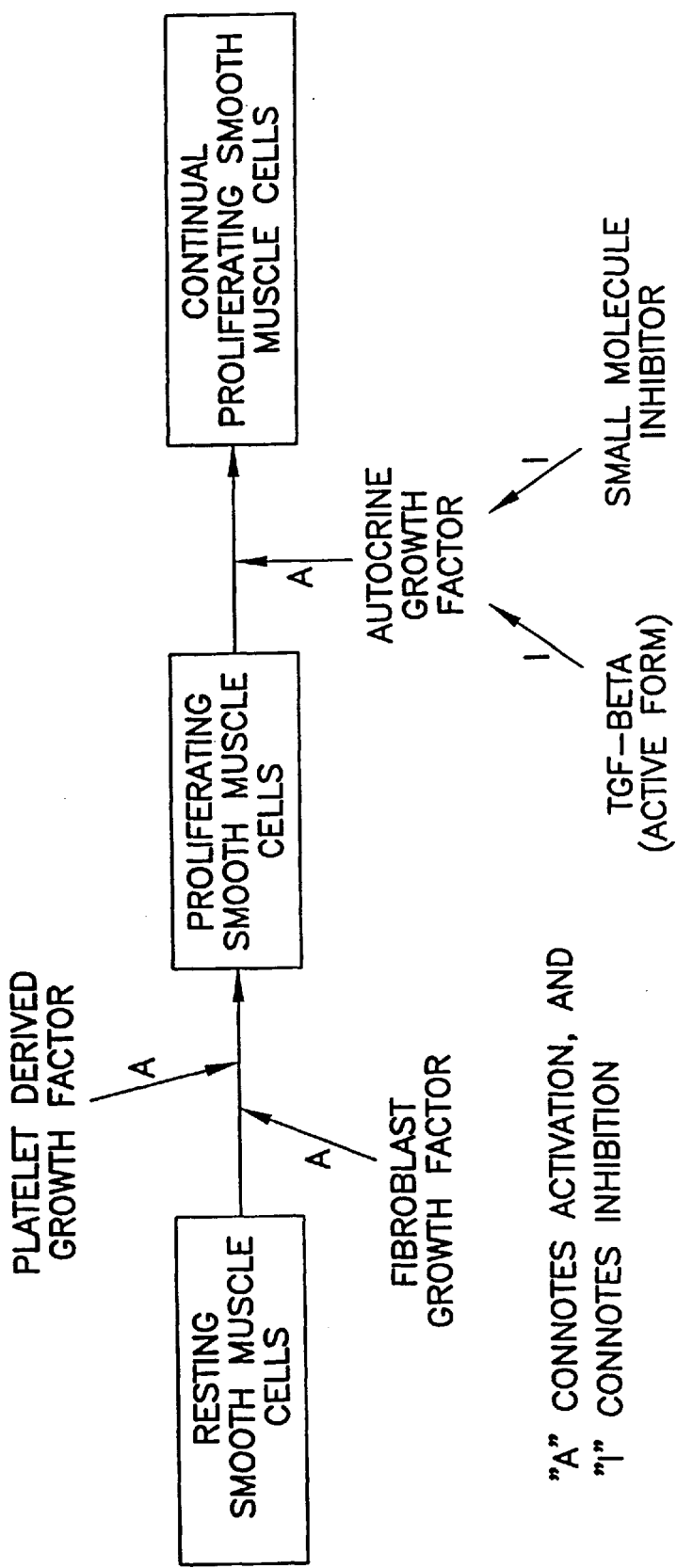

An additional pathway for the modulation of vascular smooth muscle cell proliferation is shown in FIG. 2. Resting smooth muscle cells constitute cells in their normal, quiescent non-proliferative state. Such resting smooth muscle cells may be converted to proliferating smooth muscle cells through activation by platelet derived growth factor (PDGF), fibroblast growth factor (FGF) or other stimulatory moieties. The proliferating smooth muscle cells may be converted to continual proliferating smooth muscle cells (i.e., smooth muscle cells capable of generating a pathological state resulting from over-proliferation thereof) by an autocrine growth factor. This growth factor is believed to be produced by proliferating smooth muscle cells. An increased level of autocrine growth factor, which can be inhibited by the active form of TGF-beta or an appropriately structured (i.e., designed) small molecule inhibitor, is believed to mediate the production of continual proliferating smooth muscle cells.

Lp(a) consists of low density lipoprotein (LDL) and apo(a). Apo(a) shares approximately 80% amino acid identity with plasminogen (see MacLean et al., *Nature* 330: 132, 1987). Lp(a) has been found to inhibit cell-associated plasmin activity (see, for example, Harpel et al., *Proc. Natl.*

*Acad. Sci. USA*, 86: 3847, 1989). Experiments conducted on human aortic vascular smooth muscle cells derived from healthy transplant donor tissue, cultured in Dulbecco's modified Eagles medium (DMEM)+10% fetal calf serum (FCS) as described in Kirschenlohr et al., *Am. J. Physiol.*, 265 C571 (1993), indicated the following:

1) Addition of Lp(a) to sub-confluent human vascular smooth muscle cells stimulated their proliferation in a dose dependent manner (addition of 500 nM Lp(a) to human vascular smooth muscle cells caused a reduction in doubling time from 82+/−4 hours to 47+/−4 hours);

2) Addition of apo(a) had a similar effect, although a higher concentration of apo(a) appeared to be required therefor;

3) Addition of LDL at varying concentrations up to 1 micromolar had no effect on proliferation.

One possible mode of action for Lp(a) and apo(a) is competitive inhibition of surface-associated plasminogen activation, which in turn inhibits the subsequent activation of TGF-beta by plasmin TGF-beta is a potent growth inhibitor of a number of anchorage-dependent cells, including smooth muscle cells. TGF-beta is produced as a latent propeptide having a covalently linked homodimer structure in which the active moiety is non-covalendy linked to the amino-terminal portion of the propeptide. Latent TGF-beta must be cleaved (e.g., in vitro by acid treatment or in vivo by the serine protease plasmin) in order to become capable of inhibiting the proliferation of vascular smooth muscle cells. Plasmin is therefore a leading candidate to be a physiological regulator of TGF-beta.

The hypothesis that Lp(a) and apo(a) were acting on cultured human vascular smooth muscle cells by interfering with activation of latent TGF-beta was tested. In support of this hypothesis, an observation was made that plasmin activity associated with vascular smooth muscle cells was reduced 7-fold by Lp(a) and 5-fold by apo(a). The plasmin activity in the conditioned medium was also reduced by Lp(a) and apo(a) by about 2-fold, but was much lower than cell-associated plasmin activity in vascular smooth muscle cell cultures. These observations are consistent with previous findings that Lp(a) is a more potent inhibitor of surface-associated, rather than fluid phase, plasminogen activation.

To exclude the possibility that Lp(a) was affecting the synthesis of plasminogen activators rather than plasminogen activation, plasminogen activator levels in human vascular smooth muscle cell cultures were measured in the presence and absence of the lipoproteins and in the presence of a large excess of plasminogen, so that the lipoproteins present would not significantly act as competitive inhibitors. Total plasminogen activator activity was not affected by the presence of any of the lipoproteins in the vascular smooth muscle cell cultures. For example, plasminogen activator activity in the conditioned medium remained at 0.7+/−0.6 mU/ml with Lp(a) additions up to 500 nM.

Lp(a) and apo(a) both reduced the level of active TGF-beta by more than 100-fold compared to control or LDL-treated cultures. The level of total latent plus active TGF-beta measured by ELISA as described in Example 8 was unaffected by the presence of Lp(a) or apo(a), however. These facts lead to the conclusion that Lp(a) stimulates proliferation of human vascular smooth muscle cells by inhibiting plasmin activation of latent TGF-beta to active TGF-beta.

To further test this conclusion and exclude the possibility that Lp(a) was acting by binding active TGF-beta as well as reducing plasmin activity, human vascular smooth muscle cells were cultured in the presence of Lp(a). These cells had a population doubling time of 47+/−3 hours. Addition of plasmin was able to overcome the population doubling time reducing effect of Lp(a) and reduce the cell number to control levels, with the population doubling time increased to 97+/−4 hours.

The role of plasmin in the pathway was confirmed by studies in which inhibitors of plasmin activity were added to human vascular smooth muscle cells. Like Lp(a), these protease inhibitors increased cell number. Aprotinin for example, decreased the population doubling time from 82+/−4 hours in control cultures to 48+/−5 hours, and alpha2-antiplasmin decreased the population doubling time to 45+/−2 hours. 500 nM Lp(a) and aprotinin addition resulted in only a slight additional stimulation of proliferation, with the population doubling time for cultures of this experiment being 45+/−6 hours. Neutralizing antibodies to TGF-beta similarly decreased population doubling time in vascular smooth muscle cells (see, for example, Example 1). In summary, Lp(a), plasmin inhibitors and neutralizing antibody to TGF-beta stimulate proliferation of vascular smooth muscle cells, while plasmin nullifies the growth stimulation of Lp(a). These results support the theory that the mode of action of Lp(a) and apo(a) is the competitive inhibition of plasminogen activation.

Experimentation conducted to ascertain the impact of tamoxifen on TGF-beta and vascular smooth muscle cell proliferation is set forth in detail in Example 1. The results of those experiments are summarized below.

1) Addition of tamoxifen decreased the rate of proliferation, with maximal inhibition observed at concentrations above 33 micromolar. 50 micromolar tamoxifen concentrations produced a cell number 96 hours following the addition of serum that was reduced by 66%+/−5.2% (n=3) as compared to cells similarly treated in the absence of tamoxifen.

2) Tamoxifen did not significantly reduce the proportion of cells completing the cell cycle and dividing. Inhibition of vascular smooth muscle cells caused by tamoxifen therefore appears to be the result of an increase in the cell cycle time of nearly all (>90%) of the proliferating cells.

3) Tamoxifen decreases the rate of proliferation of serum-stimulated vascular smooth muscle cells by increasing the time taken to traverse the $G_2$ to M phase of the cell cycle.

4) Tamoxifen decreased the rate of proliferation of vascular smooth muscle cells by inducing TGF-beta activity.

5) Vascular smooth muscle cells produced TGF-beta in response to tamoxifen. Tamoxifen appears to increase TGF-beta activity in cultures of rat vascular smooth muscle cells by stimulating the production of latent TGF-beta and increasing the proportion of the total TGF-beta which has been activated.

6) Tamoxifen, unlike heparin, does not act by releasing TGF-beta from inactive complexes present in serum.

7) TGF-beta mRNA was increased by approximately 10-fold by 24 hours after addition of tamoxifen (10 micromolar). This result suggests that the expression of TGF-beta mRNA by the smooth muscle cels will be increased, thereby facilitating decreased proliferation thereof by activated TGF-beta.

8) Tamoxifen is a selective inhibitor of vascular smooth muscle proliferation with an ED50 (a concentration resulting in 50% inhibition) at least 10-fold lower for vascular smooth muscle ceUs than for adventitial fibroblasts.

Additional experimentation has shown that the addition of Lp(a) or apo(a) substantially reduced the rat vascular smooth muscle cell proliferation inhibitory activity of tamoxifen, with the population doubling time in the presence of tamoxifen and Lp(a) being 42+/−2 hours (as compared to a population doubling time of 55+/−2 hours for tamoxifen alone, and a time of 35+/−2 hours for the control). Also, the presence of Lp(a) reduced the levels of active TGF-beta produced in response to the addition of tamoxifen by about 50-fold. Addition of plasmin to rat vascular smooth muscle cells treated with tamoxifen and Lp(a) resulted in most of the TGF-beta being activated, and proliferation was again slowed (with the population doubling time being 57+/−3 hours). These observations are consistent with the theory that Lp(a) acts by inhibiting TGF-beta activation.

Identification of therapeutic agents (direct or indirect TGF-beta activators or production stimulators) -that act to inhibit vascular smooth muscle cell proliferation by the pathway shown in FIG. 1 can be identified by a practitioner in the art by conducting experiments of the type described above and in Example 1. Such experimental protocols facilitate the identification of therapeutic agents useful in the practice of the present invention and capable of one of the following activities:

1) production or activation of TGF-beta;
2) having TGF-beta-like activity;
3) activation of plasminogen;
4) increase in plasmin activity; or
5) reduction of Lp(a) or apo(a) level or levels of π-I or other inhibitors of TGF-beta activation.

Identification of therapeutic agents (direct or indirect TGF-beta activators or production stimulators) that act to inhibit vascular smooth muscle cell proliferation by the pathway shown in FIG. 2 can be identified by a practitioner in the art by conducting experimentation using known techniques that are designed to identify growth factors made by proliferating smooth muscle cells, which growth factors also act on those cells (i.e., autocrine growth factors). Rational drug design can then used to screen small molecules for the ability to inhibit the production or activity of such autocrine growth factors as lead compounds for drug design. Such experimental protocols facilitate the identification of therapeutic agents useful in the practice of the present invention and capable of one of the following activities:

1) production or activation of TGF-beta;
2) having TGF-beta-like activity; or
3) inhibit the activity or production of an autocrine growth factor produced by proliferating smooth muscle cells.

Smooth muscle cell proliferation is a pathological factor in myocardial infarctions, atherosclerosis, thrombosis, restenosis and the like. Therapeutic/prophylactic agents of the present invention, including tamoxifen and the like, having at least one of the activities recited above and therefore being capable of inhibiting proliferation of vascular smooth muscle cells, are useful in the prevention or treatment of these conditions. Manipulation of the proliferation modulation pathway for vascular smooth muscle cells to prevent or reduce such proliferation removes or reduces a major component of the arterial lesions of atherosclerosis and the restenosed arteries following angioplasty, for example.

More specifically, chronically maintaining an elevated level of activated TGF-beta reduces the probability of atherosclerotic lesions forming as a result of vascular smooth muscle cell proliferation. Consequently, administration of TGF-beta activators or TGF-beta production stimulators protects against atherosclerosis and subsequent myocardial infarctions that are consequent to coronary artery blockage.

Also, substantially increasing the activated TGF-beta level for a short time period allows a recipient to at least partially offset the strong stimulus for vascular smooth muscle cell proliferation caused by highly traumatic injuries or procedures such as angioplasty. Continued delivery to the traumatized site further protects against restenosis resulting from vascular smooth muscle cell proliferation in the traumatized area.

Prevention or treatment relating to a traumatized or diseased vascular site, for example, the TGF-beta activators or production stimulators may also be administered in accordance with the present invention using an infusion catheter, such as produced by C. R. Bard Inc., Billerica, Mass., or that disclosed by Wolinsky (U.S. Pat. No. 4,824,436) or Spears (U.S. Pat. No. 4,512,762). In this case, a therapeutically/prophylactically effective dosage of the TGF-beta activator or production stimulator will be typically reached when the concentration thereof in the fluid space between the balloons of the catheter is in the range of about $10^{-3}$ to $10^{-12}$ M. It is recognized by the present inventors that TGF-beta activators or stimulators may only need to be delivered in an anti-proliferative therapeutic/prophylactic dosage sufficient to expose the proximal (6 to 9) cell layers of the intimal or tunica media cells lining the lumen thereto. Also, such a dosage can be determined empirically, e.g., by a) infusing vessels from suitable animal model systems and using immunohistochemical methods to detect the TGF-beta activator or production stimulator and its effects; and b) conducting suitable in vitro studies.

It will be recognized by those skilled in the art that desired therapeutically/prophylactically effective dosages of a TGF-beta activator or production stimulator administered by a catheter in accordance with the invention will be dependent on several factors, including, e.g.: a) the atmospheric pressure applied during infusion; b) the time over which the TGF-beta activator or production stimulator administered resides at the vascular site; c) the nature of the therapeutic or prophylactic agent employed; and/or d) the nature of the vascular trauma and therapy desired. Those skilled practitioners trained to deliver drugs at therapeutically or prophylactically effective dosages (e.g., by monitoring drug levels and observing clinical effects in patients) will determine the optimal dosage for an individual patient based on experience and professional judgment. In a preferred embodiment, about 0.3 atm (i.e., 300 mm of Hg) to about 5 atm of pressure applied for 15 seconds to 3 minutes directly to the vascular wall is adequate to achieve infiltration of a TGF-beta activator or production stimulator into the smooth muscle layers of a mammalian artery wall. Those skilled in the art will recognize that infiltration of the TGF-beta activator or production stimulator into intimal layers of a diseased human vessel wall in free or sustained-release form will probably be variable and will need to be determined on an individual basis.

While two representative embodiments of the invention relate to prophylactic or therapeutic methods employing an oral dosage form or infusion catheter administration, it will be recognized that other methods for drug delivery or routes of administration may also be useful, e.g., injection by the intravenous, intralymphatic, intrathecal, intraarterial, local delivery by implanted osmotic pumps or other intracavity routes. Administration of TGF-beta activators or production stimulators in accordance with the present invention may be continuous or intermittent, depending, for example, upon the recipient's physiological condition, whether the purpose of the administration is therapeutic or prophylactic and other factors known to skilled practitioners.

In the practice of certain embodiments of the present invention, catheter administration routes including systemic and localized delivery to the target site are preferably conducted using a TGF-beta activator or production stimulator dispersed in a pharmaceutically acceptable carrier. Tamoxifen and its structural analogs and salts, including the compounds of formula (I) can be administered by a variety of routes including oral, rectal, transdermal, subcutaneous, intravenous, intramuscular, and intranasal. These compounds preferably are formulated prior to administration, the selection of which will be decided by the attending physician. Typically, TMX and its structural analogs and salts, including the compounds of formula (I), or a pharmaceutically acceptable salt thereof, is combined with a pharmaceutically acceptable carrier, diluent or excipient to form a pharmaceutical formulation, or unit dosage form.

The total active ingredients in such formulations comprises from 0.1 to 99.9% by weight of the formulation. By "pharmaceutically acceptable" it is meant the carrier, diluent, excipient, and/or salt must be compatible with the other ingredients of the formulation, and not deleterious to the recipient thereof.

Pharmaceutical formulations containing TMX and its structural analogs and salts, including the compounds of formula (I), can be prepared by procedures known in the art using well known and readily available ingredients. For example, the compounds of formula (I) can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds also can be formulated as elixirs or solutions for convenient oral administration or as solutions appropriate for parenteral administration, for example, by intramuscular, subcutaneous or intravenous routes.

The present invention also contemplates therapeutic methods and therapeutic dosage forms involving sustained release of the TGF-beta activator or production stimulator to target cells. Preferably, the target cells are vascular smooth muscle cells, cancer cells, somatic cells requiring modulation to ameliorate a disease state and cells involved in immune system-mediated diseases that are accessible by local administration of the dosage form. Consequently, the methods and dosage forms of this aspect of the present invention are useful for inhibiting vascular smooth muscle cells in a mammalian host, employing a therapeutic agent that inhibits the activity of the cell (e.g., proliferation, formation of lipid proliferative lesions, contraction, migration or the like) but does not kill the cell and, optionally, a vascular smooth muscle cell binding protein. Sustained released dosage forms for systemic administration as well as for local administration are also employed in the practice of the present method. Formulations intended for the controlled release of pharmaceutically-active compounds in vivo include solid particles of the active ingredient that are coated or tabletted with film-forming polymers, waxes, fats, silica, and the like. These substances are intended to inhibit the dissolution, dispersion or absorption of the active ingredient in vivo. Hydroxypropylmethyl cellulose is one example of an ingredient that can provide a slow or controlled release of the active ingredient. The compounds can also be delivered via patches for transdermal delivery, subcutaneous implants, infusion pumps or via release from implanted sustained release dosage forms.

Another embodiment of the invention relates to prophylactic or therapeutic "sustained release" methods from the surface of an intravascular device employing an excipient matrix which will release the TGF-beta activators over a one-week to two-year or longer period. The surface coating and the impregnated forms of the article can be a biodegradable or nonbiodegradable polymer or ceramic material which will slowly release the TGF-beta activator at a dose rate that will inhibit the proliferation of fibromuscular cells and/or lipid accumulation which would impair the function of the device. The accumulation of fibromuscular cells, including VSMC, and their associated matrix, along with lipid containing foam cells can decrease the lumenal area of intravascular stents, synthetic grafts and indwelling catheters to an extent that blood flow is critically impaired and the device can fail functionally. The inhibition of this proliferation would extend the clinically functional life of these devices and be of significant clinical benefit to the patients.

The sustained release dosage forms of this embodiment of the invention needs to deliver a sufficient anti-proliferative, preferably cytostatic, dosage to expose cells immediately adjacent to the device surface to be therapeutic. This would inhibit cellular attachment, migration and proliferation of the fibromuscular cells and foam cells. This dosage is determinable empirically by implanting a specific device intravascularly with variable amounts of the TGF-beta activator and modification of the polymer excipient, both of which would affect the rate and duration of the drug release required to achieve the cytostatic dosing which has been demonstrated in vascular smooth muscle cell tissue culture experiments. Different types of devices may require different periods of therapeutic drug release. For example, the use in grafts and stents are considered permanently implanted devices; however, it may not be necessary to have the active agent continuously released from the device. It appears from initial observations that if excessive proliferation is prevented until the graft or stent is surrounded by quiescent tissue and covered by intact endothelium then continued release of cytostatic agents may be unnecessary. Devices such as indwelling catheters, however, do not become embedded in quiescent vascular wall tissue and overgrown with endothelium. These devices may require the continual release of drugs to suppress the proliferation of tissue over their external and lumenal surfaces. To achieve this prolonged period of sustained drug release, larger amounts of agent and different types of, or modification of, the polymer or excipient are preferable.

The sustained release dosage forms of the present invention, particularly, for local administration, are preferably either non-degradable microparticulates or nanoparticulates or biodegradable microparticulates or nanoparticulates. More preferably, the microparticles or nanoparticles are formed of a polymer containing matrix that biodegrades by random, nonenzymatic, hydrolytic scissioning. A particularly preferred structure is formed of a mixture of thermoplastic polyesters (e.g., polylactide or polyglycolide) or a copolymer of lactide and glycolide components. The lactide/glycolide structure has the added advantage that biodegradation thereof forms lactic acid and glycolic acid, both normal metabolic products of mammals.

Therapeutic dosage forms (sustained release-type) of the present invention exhibit the capability to deliver therapeutic agent to target cells over a sustained period of time. Such dosage forms are disclosed in co-pending U.S. patent application Ser. No. 08/241,844, filed May 12, 1994, which is a continuation-in-part of Ser. No. 08/62,451, filed May 13, 1993, which is in turn a continuation-in-part of Ser. No. 08/011,669, which is in turn a continuation-in-part of PCT application US 92/08220, filed Sep. 25, 1992. These applications are incorporated by reference herein. Therapeutic dosage forms of this aspect of the present invention may be of any configuration suitable for this purpose. Preferred sustained release therapeutic dosage forms exhibit one or more of the following characteristics:

microparticulate (e.g., from about 0.5 micrometers to about 100 micrometers in diameter, with from about 0.5 to about 2 micrometers more preferred) or nanoparticulate (e.g., from about 1.0 nanometer to about 1000 nanometers in diameter, with from about 50 to about 250 nanometers more preferred), free flowing powder structure;

biodegradable structure designed to biodegrade over a period of time between from about 3 to about 180 days, with from about 10 to about 21 days more preferred, or nonbiodegradable structure to allow therapeutic agent diffusion to occur over a time period of between from about 3 to about 180 days, with from about 10 to about 21 days preferred;

biocompatible with target tissue and the local physiological environment into which the dosage form is being administered, including biocompatible biodegradation products;

facilitate a stable and reproducible dispersion of therapeutic agent therein, preferably to form a therapeutic agent-polymer matrix, with active therapeutic agent release occurring through one or both of the following routes: (1) diffusion of the therapeutic agent through thedosage form (when the therapeutic agent is soluble in the polymer or polymer mixture forming the dosage form); or (2) release of the therapeutic agent as the dosage form biodegrades; and capability to bind with one or more cellular and/or interstitial matrix epitopes, with from about 1 to about 10,000 binding protein/peptide-dosage form bonds preferred and with a maximum of about 1 binding peptide-dosage form per 150 square angstroms of particle surface area more preferred. The total number bound depends upon the particle size used. The binding proteins or peptides are capable of coupling to the particulate therapeutic dosage form through covalent ligand sandwich or non-covalent modalities as set forth herein.

For example, nanoparticles containing a compound of the formula (I) may be prepared using biodegradable polymers including poly(D,L-lactic acid)PLA, poly(D,L-lactic-coglycolic) PLGA, methacrylic acid copolymer, poly(epsilon-caprolactone), using either 1) n-solvent emulsification-evaporation techniques or 2) emulsification—precipitation techniques. These processes involve dispersion of polymer in an organic solvent (e.g., acetone or benzyl alcohol) with or without a co-solvent, typically methylene chloride. The compound of formula (I) is contained in the organic solvent. In some cases, solvents are then mixed and then added dropwise to an aqueous solution containing stabilizing hydrocolloid [e.g., poly(vinyl alcohol) or gelatin] (i.e., oil in water) with mechanical agitation or sonication. Following formation of the stable emulsion, the chlorinated solvent is removed via evaporation of the stirred emulsion, yielding nanoparticles that then can be freed of organic solvents by tangential filtration or repeated washings by centrigation/resuspension. The resultant aqueous suspension can then be frozen with or without saccharide or other cryoprotectants and lyophilized to yield nanoparticles capable of resuspension in physiological salt solutions with simple agitation or sonication.

Alternatively, the aqueous solution can be added with agitation or sonication to the organic phase lacking chlorinated solvent (i.e., water-in-oil emulsion) followed by further addition of aqueous solution to achieve a phase inversion, to precipitate the nanoparticles. Alternatively, precipitation can be augmented by addition to salting-out agents in the aqueous solvent. Typically, for emulsification-evaporation technique 750 mg PLGA can be dissolved in 30 mL of methylene chloride. Five mL of methylene chloride containing 75 mg of a compound of formula (I), for example, tamoxifen, is added. This organic phase is added dropwise to 180 mL of aqueous solution of 2.5% poly(vinyl alcohol, PVP) (20–70 kD mol Wt.) with sonication using a Branson 450 sonifier at 15–55 watt output, for approximately 10 minutes to form a soluble emulsion. Sonication is performed in an ice bath at a temperature not exceeding 15° C. the emulsion is then further stirred at room temperature for 24 hours to allow for evaporation of the chlorinated solvent. The resultant nanoparticles are purified further using a Sartorius targeted filtration device fitted with a 100 mm pore polyolefin cartridge filter. For the emulsification-precipitation technique, 10 mL of aqueous PMP (10–30% w/w) is added, under mechanical stirring at 1200–5000 rpm, to 5 mL of benzyl alcohol containing 10–15% w/w polymer PLA or PLGA and 10–15 w/w of a compound of the formula (I), for example, tamoxifen, following oil-in-water emulsion formation over 5 minutes. Water (160 mL) is then added to effect a phase inversion, resulting in diffusion of organic solvent into the water with concomitant precipitation of polymer as solid nanoparticles in the ensuing 10 minutes.

For TGF-beta activators or production stimulators, such as compounds of the formula (I), several exemplary dosing regimens are contemplated, depending upon the condition being treated and the stage to which the condition has progressed. For prophylactic purposes with resect to atherosclerosis, for example, a low chronic dose sufficient to elevate in vivo TGF-beta production is contemplated. An exemplary dose of this type is about 0.1 mg/kg/day (ranging between about 0.1 and about 10 mg/kg/day), preferably about 0.1–1.0 mg/kg/day, most preferably about 0.3 mg/kg/day. Another exemplary dose range is from about 0.01 to about 1000 micrograms/ml. Such low doses are also contemplated for use with respect to ameliorating stenosis following relatively low trauma injury or intervention, such as vein grafts or transplants or organ allografts, for example.

For prevention of restenosis following angioplasty, an alternative dosing regimen is contemplated which involves a single "pre-loading" dose (or multiple, smaller pre-loading doses) given before or at the time of the intervention, with a chronic smaller (follow up) dose delivered daily for two to three weeks or longer following intervention. For example, a single pre-loading dose may be administered about 24 hours prior to intervention, while multiple preloading doses may be administered daily for several days prior to intervention. Alternatively, one or more pre-loading doses may be administered about 14 weeks prior to intervention. These doses will be selected so as to maximize TGF-beta activator or production stimulator activity, while minimizing induction of synthesis and secretion of extracellular matrix proteins. Such a dosing regimen may involve a systemic preloading dose followed by a sustained release chronic dose, or the sustained release dosage form may be designed to deliver a large dose over a short time interval as well as a smaller chronic dose for the desired time period thereafter. Some nausea may be encountered at the higher dose; however, the use of a sustained release or other targeted dosage form is expected to obviate this side effect, because the recipient will not be subjected to a high systemic dose of the therapeutic agent The local particulate dosage form administration may also localize to normal tissues that have been stimulated to proliferate, thereby reducing or eliminating such pathological (i.e., hyperactive) conditions. An example of this embodiment of the present invention involves intraocular administration of a particulate dosage form coated with a binding protein or peptide that localizes to pericytes and smooth muscle cells of neovascularizing tissue. Proliferation of these pericytes causes degenerative eye disease. Preferred dosage forms of the present invention release compounds capable of suppressing the pathological proliferation of the target cell population. The preferred dosage forms can also release compounds that increase vessel lumen area and blood flow, reducing the pathological alterations produced by this reduced blood supply.

It will be recognized that where the TGF-beta activator or production stimulator is to be delivered with an infusion catheter, the therapeutic dosage required to achieve the desired inhibitory activity can be anticipated through the use of in vitro studies. In a preferred aspect, the infusion catheter may be conveniently a double balloon or quadruple balloon catheter with a permeable membrane. In one representative embodiment, a therapeutically effective dosage of a TGF-beta activator or production stimulator is useful in treating vascular trauma resulting from disease (e.g., atherosclerosis, aneurysm, or the like) or vascular surgical procedures such as angioplasty, atheroectomy, placement of a stent (e.g., in a vessel), thrombectomy, and grafting. Atheroectomy may be performed, for example, by surgical excision, ultrasound or laser treatment, or by high pressure fluid flow. Grafting may be, for example, vascular grafting using natural or synthetic materials or surgical anastomosis of vessels such as, e.g., during organ grafting. Those skilled in the art will recognize that the appropriate therapeutic dosage for a given vascular surgical procedure (above) is determined in in vitro and in vivo animal model studies, and in human preclinical trials.

Sustained release dosage forms of an embodiment of the invention may only need to be delivered in an antiproliferative therapeutic dosage sufficient to expose the proximal (6 to 9) cell layers of the tunica media smooth muscle cells lining the lumen to the dosage form This dosage is determinable empirically, e.g., by a) infusing vessels from suitable animal model systems and using immunohistochemical, fluorescent or electron microscopy methods to detect the dosage form and its effects; and b) conducting suitable in vitro studies.

In a representative example, this therapeutically effective dosage is achieved by determining in smooth muscle cell tissue culture the pericellular agent dosage, which at a continuous exposure results in-a therapeutic effect between the toxic and minimal effective doses. This therapeutic level is obtained in vivo by determining the size, number and therapeutic agent concentration and release rate required for particulates infused between the smooth muscle cells of the artery wall to maintain this pericellular therapeutic dosage.

Human vascular smooth muscle cells (VSMC) are more difficult to grow in culture than VSMC derived from other species, such as rat. Medium conditioned on human VSMC decreased the proliferation of rat VSMC in vitro. Entry of rat VSMC into S phase of the cell cycle was not affected. However, the duration of $G_2$ and/or M phase was extended. Anti-TGF-beta antibody reversed the delayed entry into M phase caused by exposure to human VSMC conditioned medium (HCM). An examination of the HCM showed that 64±12% of the TGF-beta present in the medium was already activated. In contrast, rat VSMC conditioned medium displayed very low levels of latent TGF-beta and no detectable TGF-beta activity. Human VSMC were found to produce tissue plasminogen activator (TPA) activity in culture. The TPA leads to an increase in plasmin activity, which in turn activates TGF-beta. This was confirmed by culturing human VSMC in the presence of aprotinin, a plasmin inhibitor. Aprotinin increased the rate of proliferation of human VSMC to almost the same extent as neutraling anti-TGF-beta antibodies and $\alpha_2$-antiplasmin. Thus, growth of human VSMC in culture is determined by the production of TGF-beta activated by plasmin, which feeds back in an autocrine loop to increase the duration of the cell cycle.

Subcultured human aortic VSMC remain more differentiated in culture than rat aorta VSMC (i.e., they contain higher levels of the smooth muscle-specific isoforms of myosin heavy chain (SM-MHC) and α-actin). TGF-beta likely plays a role in maintaining SM-MHC and α-actin content, and thus may be responsible for maintaining cells in a more differentiated phenotype. In view of these data, heparin, which is believed to release TGF-beta from inactive complexes in the serum, would be predicted to have little effect on the rate of proliferation of human VSMC, which is already inhibited by endogenous active TGF-beta production. Such observations may explain why human clinical trials of heparin administered after PICA have failed to demonstrate any beneficial effect.

Freshly dispersed rat aortic VSMC lose SM-MHC and α-SM actin as they start to proliferate. After 7 days in culture when the cells reach confluence, serum is removed, and approximately 40% of the VSMC reexpress SM-MHC and α-SM actin at levels comparable to those present in freshly dispersed cells. If the cells were subcultured for more than five passages and allowed to reach confluence, less than 1% reexpress SM-MHC even after prolonged serum withdrawal. These cells represent proliferating de-differentiated VSMC.

When primary cultures of rat aortic VSMC are exposed to TGF-beta, the loss of the 204 kD (SM-1) and 200 kD (SM-2) SM-MHC isoforms is substantially inhibited. However, TGF-beta did not induce rexpression of SM-MHC in subcultured cells that have very low levels of this protein. Therefore, TGF-beta can maintain a cell's differentiated state (as defined by SM-MHC content), but cannot induce redifferentiation in a de-differentiated proliferating cell. Since TGF-beta extends the $G_2$ phase of the cell cycle in both primary and passaged VSMC cultures, the data suggest that the pathways that mediate proliferation and differentiation are regulated independently.

Specific markers of both differentiated and proliferating VSMCs have been isolated. Four cell populations were probed using generated cDNAs: (a) freshly dispersed rat aortic cells; (b) freshly dispersed rat aortic VSMC after 7 days in culture (D7 cells); (c) freshly dispersed rat aortic VSMC after subculturing 12 times (S12 cells); and (d) rat fibroblasts. Five classes of gene markers were defined. Class 1 cDNAs were expressed to a similar level in all of the RNAs. Class 2 cDNAs were highly expressed in RNA from freshly dispersed aortic cells, but were barely detectable in D7 or S12 cells and were not detectable in rat fibroblasts. Class 3 cDNAs were expressed at similar levels in freshly dispersed aortic, D7 and S12 cells. Class 4 cDNAs showed higher expression in freshly dispersed aortic and D7 cells than in S12 cells and fibroblasts. Class 5 cDNAs were expressed more strongly in S12 cells than in freshly dispersed aortic cells, D7 cells and fibroblasts. Class 4 genes included α-SM actin, γ-SM actin, SM22α, calponin, tropoelastin, phospholamban and CHIP28. In addition, previously defined markers of the differentiated phenotype include SM-MHC, integrin and vinculin. Class 5 genes included matrix Gla (MGP) and osteopontin. When passaged cells were made quiescent by removal of serum, the levels of MGP and osteopontin did not change significantly, indicating that high expression of these two genes occurs in VSMC that have undergone proliferation, but does not depend on the cells being in the cell cycle.

Such studies of gene expression provide insight into the processes of de-differentiation that occur during proliferation of VSMC. In situ hybridization analysis of balloon-injured rat carotid arteries suggests that dividing intimal cells present 7 days after injury express high levels of both osteopontin and MGP RNA. In contrast, osteopontin is only weakly expressed in the media of intact rat aorta and carotid arteries. Osteopontin and MGP may play a role in regulating calcification, which can occur rapidly in vascular lesions.

In the course of investigating potential heterogeneity of cells from rat aortas, three groups of VSMC clones have been identified. One group consists of small cells that have an epithelioid or cobblestone morphology and proliferate without the need for added growth factors, suggesting production of an autocrine growth factor(s). The second group consists of intermediate size, spindle shaped cells that grow in a characteristic "hills and valleys" pattern and are dependent on exogenous growth factors. These cells resemble the predominant cell morphology in standard cultures of adult aortic VSMC. The third group consists of large, often multinucleate, cells with limited proliferative capacity. These large cells express high quantities of smooth muscle specific proteins.

All three types of cells could be isolated from neonatal and adult rat aortae. However, aortas from young rats yielded high proportions of the small cell clones, while those from adult rats yielded high proportions of intermediate and large cell clones. Clones of small VSMC can be induced to convert to intermediate sized cells by treatment with TGF-beta. A proportion of these cells, in turn, converts to large cells if plated at low density. The small cells may represent a progenitor cell and the large, non-proliferating cells may represent mature VSMC.

VSMC derived from neonatal rat aortas differ from normal adult VSMC in several ways: (a) they do not require exogenous growth factors for sustained growth; (b) they secrete PDGF-like growth factors; (c) they grow with a characteristic epithelioid morphology; and (d) they express high levels of cytochrome P450IA1, elastin and osteopontin (*J. Biol. Chem.* 266:3981–86, 1991; *Biochem. Biophys. Res. Comm.* 177:867–73, 1991; *Nature* 311:669–71, 1984). After intimal damage, neointiral lesions grow with an epithelioid morphology, secrete a PDGF-like protein and display increased expression of osteopontin in the vascular wall (*Proc. Natl. Acad. Sci. USA* 83:7311–15, 1986). These data are consistent with the presence in vivo of a subpopulation of VSMC that comprises a diminishing proportion of the total cell population with age and which proliferates preferentially.

TGF-beta is released by platelets, macrophages and VSMC at sites of vascular injury. Since VSMC and endothelial cells at the site of vascular injury can synthesize and release t-PA, a local mechanism for activating secreted TGF-beta exists. The level of t-PA activity depends on expression of plasminogen activator inhibitor-1 (PAI-1) which is also synthesized in the vessel wall, and may be up-regulated by TGF-beta. In addition, TGF-beta binds with high affinity to α2-macroglobulin. Such binding renders TGF-beta unable to bind to cell surface receptors for TGF-beta. Polyanionic glycosaminoglycans, such as heparin, are also normally present in the vessel wall, and these moieties can reverse the association of TGF-beta with α2-macroglobulin. The phenotypic state of the VSMC may affect the VSMC response to activated TGF-beta. The phenotypic state of the VSMC may be influenced by their extracellular environment. Accordingly, the biological effects of TGF-beta are subject to a variety of regulatory mechanisms.

TGF-beta inhibits DNA synthesis in rat aortic VSMC stimulated with either PDGF or EGF. In serum stimulated cells, however, TGF-beta has little effect on DNA synthesis. Instead, TGF-beta exerts its anti-proliferative effect by prolonging the $G_2$ phase of the cell cycle. Likewise, heparin inhibits proliferation of serum-stimulated rat VSMC by extending the $G_2$ phase of the cell cycle. This effect of heparin can be eliminated by anti-TGF-beta antibody. These observations suggest that the anti-proliferative effect of heparin on VSMC in vitro and possibly in vivo may be exerted through the release of TGF-beta.

When VSMC are dispersed in cell culture, they lose contractile proteins and modulate to a "synthetic" phenotype as they proliferate. The majority of VSMC in atheromatous plaques appear to have this synthetic phenotype also. Since loss of smooth muscle-specific proteins occurs spontaneously in cell culture in the absence of mitogens where no proliferation occurs, this phenotypic change is not attributable to mitogenic stimulation, but rather to removal of the cells from their extracellular matrix. The matrix contains large quantities of collagen and glycosaminoglycans that may maintain VSMC in a contractile state. TGF-beta does not exert its anti-proliferative effect through inhibition of phenotypic modulation, however, since it is effective at slowing proliferation of passaged cells that can no longer express contractile proteins. Thus, TGF-beta displays the independent properties of (1) maintaining differentiated adult VSMC in the contractile phenotype; (2) causing maturation of small VSMC to intermediate size, spindle-shaped VSMC; and (3) inhibiting VSMC proliferation regardless of phenotype. Change from a contractile to synthetic phenotype is not obligatory for proliferation.

Cultured VSMC synthesize and secrete large quantities of extracellular matrix proteins. TGF-beta enhances production of extracellular matrix proteins, which favors maintenance of the synthetic phenotype in cells that have been allowed to modulate. In addition, TGF-beta increases expression of numerous protease inhibitors, which also increase accumulation of extracellular matrix proteins.

In hypertension, there is increased thickness of the vessel media, with a consequent decrease in maximum lumen diameter, leading to increased vascular resistance. The increased thickness of the vessel media is due to growth of VSMC within the media. In large conductance vessels, such as the aorta, the VSMC growth is believed to be attributable primarily to VSMC hypertrophy (i.e., enlargement of the cell without proliferation). In hypertensive animals, these vessels display an increased incidence of polyploid cells within the aortic media. In resistance vessels, such as the mesenteric arteries, however, VSMC proliferation may contribute to the increased thickness of the vessel media. Previously, VSMC growth in hypertension was believed to result from elevated blood pressure. Current data suggest that increased vascular tone and VSMC hypertrophy and/or hyperplasia may be caused independently by a common stimulus. For instance, under certain circumstances, the vasoconstrictor peptide AII may be mitogenic for VSMC. Further, VSMC stimulated with AII also synthesize TGF-beta. Thus, any mitogenic effect of AII might be inhibited by TGF-beta, with the net effect of AII stimulation being arrest in $G_1$ and hypertrophy without proliferation. AII may induce activation of TGF-beta by stimulating expression of t-PA by VSMC.

The VSMC involved in hypertension remain within the media of the vessel and are surrounded by a heparin-containing extracellular matrix. Therefore, any TGF-beta produced is freely available and will maintain VSMC in a contractile state.

In obliterative vascular disease, such as atherosclerosis, VSMC migrate from the media and proliferate in the intima. There they secrete extracellular matrix proteins and form a lipid-rich plaque that encroaches on the vascular lumen. This process is similar to, but slower than, the process that occurs following PICA, leading to restenosis. Such inappropriate intimal VSMC proliferation also occurs in vascular bypass grafts and the arteries of transplanted organs, leading to graft occlusion and organ failure, respectively. In atherosclerosis, the VSMC involved in the lesion are generally of the synthetic phenotype and localized in the intima, in contrast to the VSMC involved in hypertension.

For medial VSMC involved in atherosclerosis, VSMC migration is accompanied by an increase in synthesis and secretion of matrix proteins and by proliferation. TGF-beta may reduce or prevent the VSMC proliferative response to mitogens and/or may induce synthesis and secretion of extracellular matrix proteins. The effect of TGF-beta in this case would be reduction of cellularity and increase of the matrix component of an atherosclerotic plaque.

Alternatively, VSMC in the intima may arise from a population of neonatal-like VSMC that are capable of migration and preferential proliferation following vascular injury. This intimal phenotype may be either induced or selected in response to vessel injury. When these cells are exposed to TGF-beta, the neonatal-like, small cell phenotype should convert into intermediate sized, spindle-shaped cells that no longer produce an autocrine growth factor. Thus, cells of the intermediate size should have a decreased tendency to proliferate. Over time, a portion of this intermediate sized population of cells would convert to the large, non-proliferative VSMC phenotype.

If VSMC are producing autocrine TGF-beta, tamoxifen has minimal or no further inhibitory effect on VSMC proliferation. Moreover, these TGF-beta-producing VSMC exhibit responses to mitogenic stimuli that may differ from those of VSMC that are not producing TGF-beta. Such data provides further evidence of a complex interaction between the elements that are likely involved in atherosclerosis and vascular injury or trauma.

Transgenic mice that express the human apo(a) gene are useful tools for studying TGF-beta activation, VSMC proliferation and vascular lesions that mimic early human atherosclerotic lesions. In these mice, the apo(a) accumulates in focal regions in the luminal surface of vessel walls. These foci of apo(a) inhibit plasminogen activation, which leads to a decrease in production of plasmin. A low local concentration of plasmin results in reduced activation of TGF-beta This inhibition of TGF-beta activation is greatest at sites of highest apo(a) accumulation. Further, these effects are observed whether the transgenic mice are fed a normal diet or a lipid-rich diet. Serum levels of activated TGF-beta correlate with the immunofluorescence determinations performed on tissue sections. Osteopontin, a marker of activated VSMC, co-localized with focal apo(a) accumulation and regions of very low TGF-beta activation.

The formation of the atherosclerotic lesion can occur in five stages:

1. MIGRATION. In a healthy vessel, most or all of the smooth muscle cells (SMC) are contained in the vessel media. The appearance of SMC in the enlarged intima during lesion formation must therefore require migration of the SMC from the media to the intima of the vessel. Inhibition of this SMC migration would significantly alter the nature of the lesion, and may ameliorate the pathology associated with lesion formation.

2. LIPID ACCUMULATION. Medial SMC in healthy vessel walls do not significantly accumulate lipid. However, intimal SMC have an increased capacity for lipid uptake and storage. When exposed to elevated levels of circulating lipid (particularly low density lipoprotein; LDL), SMC may become saturated with fatty lipid and die. The accumulation of lipid is necessary for the progression of the lesion to clinical significance, since it forms the thrombogenic necrotic core of the lesion. Inhibition of lipid accumulation in the SMC should significantly reduce or prevent lesion formation and/or progression, thus reducing or preventing atherosclerosis and resultant myocardial infarction.

3. RECRUITMENT OF INFLAMATORY CELLS. Human lesions contain many macrophage-derived cells. The process of recruitment, the function of these cells, and their contribution to pathology are unclear. An oversimplified mechanism suggests that macrophages are attracted to the lipid accumulating in the lesion, in order to remove the lipid from the vessel wall. While inhibition of recruitment of macrophage-derived cells might reduce lesion pathology, it may also speed progression to the lipid-filled, rupture-prone state.

4. PROLIFERATION. Intimal SMC accumulation is accompanied by medial thinning in many cases. Therefore, total SMC-number may not increase significantly at the lesion site. Furthermore, the chronic nature of atherosclerosis makes it difficult to detect stimulation of proliferation in these lesions. Data obtained from transgenic apo(a) mice suggest that apo(a) may stimulate SMC proliferation. However, evidence that SMC hyperplasia is the major contributor to atherosclerosis is lacking. Thus, the ultimate effect that inhibition of apo(a) has on atherosclerosis is dependent on the contribution of SMC proliferation to initiation or progression of an atherosclerotic plaque.

5. EXTRACELLULAR MATRIX DEPOSITION. Atherosclerotic lesions are also rich in extracellular matrix (ECM), and in particular, collagen fibers.

Increased ECM synthesis may increase plaque stability. Early plaque rupture, leading to myocardial infarction, may be associated with low ECM deposition and resultant weakening of the fibrous cap that overlays the necrotic, lipid-rich core of the lesion.

Accordingly, atherosclerosis involves the complex interplay of various processes, some of which may be yet unidentified. Targeting a single process in an effort to reduce or prevent atherosclerosis depends on knowledge of the relative contribution of each process to the manifested pathology. For these reasons, a coordinated, therapeutic strategy is preferred. An exemplary strategy involves inhibition of SMC migration, lipid accumulation and proliferation, with possible beneficial effects of increasing ECM deposition.

A diagnostic assay for identifying patients at risk for atherosclerosis, and therefore for identifying suitable candidates for therapy, is also an embodiment of the invention. In addition, this diagnostic assay provides a means to monitor patients that are being treated for atherosclerosis. In one format, a sandwich ELISA for determining total TGF-beta, ELISA plates are coated with an antibody that binds both latent and active TGF-beta. Patient sera are incubated with these ELISA plates, then the plates are washed to remove unbound components of the patients' sera. Rabbit anti-TGF-beta antibody, capable of binding both latent and active TGF-beta, is then added to the plates and incubated. The plates are then washed to remove unbound antibody, and peroxidase-labeled anti-rabbit IgG is added. After incubation and washing, the plates are exposed to the chromogenic substrate, orthophenylenediamine. The presence of total TGF-beta in patients' sera is then determined colorimetrically at $A_{492}$ by comparison to a standard curve. In patients treated with an agent that modifies TGF-beta, a pretreatment determination of TGF-beta can be compared with post-treatment time points to monitor treatment results and effectiveness.

In an alternative format, TGF-beta type II receptor extracellular domain, which recognizes the active form of TGF-beta, is coated onto ELISA plates. Patient sera are added to the plates, and processed as above. This assay measures active TGF-beta present in sera In another alternate format, fluorescent-labeled anti-TGF-beta antibody or TGF-beta type I receptor extracellular domain is used in place of peroxidase labeled second antibody to detect the presence of TGF-beta in patients' sera. In yet another alternate format, anti-TGF-beta antibody or TGF-beta type II receptor extracellular domain is labeled with a radioactive moiety capable of detection by standard means. These latter two assays may be performed in an ELISA format, with or without using the additional anti-TGF-beta antibody described above. In addition, these latter two assays are amenable to other automated or non-automated assay and detection methods.

To determine whether an agent is a TGF-beta activator or TGF-beta production stimulator, an agent or mixture of agents is first tested on rat aortic vascular smooth muscle cells (rVSMCs) for their ability to stimulate the production of active TGF-β in the culture medium as originally described for tamoxifen. See Grainger et al. (*Biochem. J.,* 294, 109 (1993)). The key step in demonstrating that cells have a reduced proliferation rate as a result of TGF-β production and activation is that the effect can be fully reversed by neutralizing antibodies to TGF-β. Incomplete reversal of a decreased rate of proliferation is evidence for TGF-β independent effect(s), which may include toxicity. The effects of an agent are then tested on explant human aortic smooth muscle cells (HVSMC) as described in Example 3 to determine whether the agent also stimulates production of TGF-β by these cells. The use of explant hVSMCs, prepared and grown as described in Example 3, is essential because (i) explant hVSMCs grown under non-optimal conditions (particularly at low cell densities) will spontaneously produce TGF-β; (ii) hVSMC cultures from cells prepared by enzyme dispersal spontaneously produce substantial amounts of TGF-β in culture (Kirschenlohr et al., *Am. J. Physiol.,* 265, C571 (1993)) and therefore cannot be used for screening; and (iii) the sensitivity of rVSMCs and hVSMCs to agents which induce the cells to produce TGF-β differs by up to 100-fold.

In screening for agents likely to be effective for clinical purposes, it is therefore necessary to use hVSMCs to determine both potency and the therapeutic window between effective concentrations and toxic concentrations for human cells. Candidate agents which pass the in vitro cell culture screens are then tested on one or more mouse models of lipid lesion formation. Efficacy of candidate agents is tested by the protocols described in Example 7 for C57B16 mice and mice expressing the human apo(a) transgene that are fed a high fat diet, and also in apoE knockout mice fed a normal diet. Another animal model useful in screening agents is the cholesterol-fed Watanabe rabbit. Finally, small scale, pilot studies on candidate molecules are tested in patient groups with clinically significant coronary artery disease for the ability of the drug to increase circulating concentrations of active TGF-β or to activate latent forms of TGF-β.

The invention will be better understood by making reference to the following specific examples.

EXAMPLE 1

Impact of Tamoxifen on Vascular Smooth Muscle Cells and the Relationship thereof to TGF-Beta Production and Activation Cell culture, DNA synthesis assay and cell counting.

Rat vascular smooth muscle cells were cultured after enzymatic dispersion of the aortic media from 12–17 week old Wistar rats as described in Grainger et al., *Biochem. J., 277: 145–151, 1991*. When the cells reached confluence (after about 6 days) the cells were released with trypsin/EDTA (available from Gibco) and diluted 1:2 in Dulbecco's modification of Eagle's medium (DMEM; available from ICN/Flow) supplemented with 100 U/ml penicillin and 10% fetal calf serum (FCS). The cells were then replated on tissue culture plastic (available from ICN/Flow) at approximately $1\times10^4$ cells/cm². The cells were subcultured repeatedly in this way when confluence was attained (about every 4 days), and the cells were used between passages 6 and 12.

Rat adventitial fibroblasts were cultured as described in Grainger et al., *Biochem. J., 283: 403408, 1992*. Briefly, the aortae were treated with collagenase (3 mg/ml) for 30 minutes at 37° C. The tunica adventitia was stripped away from the media. The adventitia was dispersed for 2 hours in elastase (1 mg/ml) and collagenase (3 mg/ml) dissolved in medium M199 (available from ICN/Flow). The cells were then spun out (900×g, 3 minutes), resuspended in DMBM+ 10%.FCS and plated out at $8\times10^4$ cells/cm² on tissue culture plastic. When the cells reached confluence (after about 10 days), they were subcultured as described for vascular smooth muscle cells. Adventitial fibroblasts were subcultured every 3 days at 1:3 dilution and used between passages 3 and 9.

DNA synthesis was assayed by [³H]-thymidine incorporation as described in Grainger et al., *Biochem. J., 277:145–151, 1991*. Vascular smooth muscle cells were subcultured, grown in DMEM+10% FCS for 24 hours, made quiescent in serum-free DMEM for 48 hours and restimulated with 10% FCS at "0" hours. [³H]-thymidine (5 microcuries/ml; available from Amersham International) was added 12 hours after restimulation and the cells were harvested after 24 hours. DNA synthesis by adventitial fibroblasts was determined similarly, except that the cells were made quiescent in serum-free DMEM for 24 hours.

Cells were prepared for counting by hemocytometer from triplicate culture dishes as described in Grainger et al., *Biochem. J., 277:145–151, 1991*. Cells were also counted by direct microscopic observation of gddded culture dishes. The grids were scored into the plastic on the inner surface, so that the cells could not migrate into or out of the area being counted during the experiment. Cells in each of four squares in two separate wells were counted at each time point. All cell counting experiments were repeated on at least three separate cultures.

A stock solution of tamoxifen (5 mM; available from ICI Pharmaceuticals) was made up in 10% ethanol (EtOH) and diluted in DMEM and 10% FCS to give the final concentration. The effects of each tamoxifen concentration were compared with the effects observed in control wells containing the same final concentration of the ethanol vehicle. Recombinant TGF-beta (available from Amersham International) was dissolved in 25 mM Tris/Cl to give a 5 microgram/ml stock solution and sterile filtered through a Spinnex Tube (such as a Centrex Disposable Microfilter Unit available from Rainin Instrument Company, Inc., Wobum, Mass.). Neutralizing antiserum to TGF-beta (BDA19; available from R & D Systems) was reconstituted in sterile MilliQ water (available from Millipore Corporation, Bedford, Mass.). At 10 micrograms/ml, this antibody completely abolished the activity of 10 ng/ml recombinant TGF-beta on subcultured (8th passage) vascular smooth muscle cells.

Assays for TGF-Beta.

The TGF-beta activity present in medium conditioned on various cells was determined by DNA synthesis assay on mink lung endothelial (MvLu) cells; a modification of the assay described in Danielpour et al., *J. Cell. Physiol.*, 138: 79–83, 1989. MvLu cells were subcultured at 1:5 dilution in DMEM+10% FCS. After 24 hours, the medium was replaced with the conditioned medium to be tested in the absence or presence of the neutralizing antiserum to TGF-beta at 10 microgrms/ml. DNA synthesis during a 1 hour pulse of [$^3$H]-thymidine (5 microcuries/ml) was determined 23 hours after addition of the test medium. TGF-beta activity was calculated as the proportion of the inhibition of DNA synthesis which was reversed in the presence of neutralizing antibody, using a standard curve to convert the inhibition values into quantities of TGF-beta. The TGF-beta standards and conditioned media both contained 10% FCS in DMEM.

The total latent and active TGF-beta present was determined by a sandwich ELISA (see Example 8). Maxisorb 96well ELISA plates (available from Gibco) were coated with neutralizing antiserum against TGF-beta (B3DA19; available from R & D Systems) at 2 micrograms/cm in phosphate buffered saline (PBS) overnight at room temperature. The plates were washed between each step with tris-buffered saline containing 0.1% Triton X-100 (available from Sigma Chemical Company). The plates were incubated with samples for 2 hours, with a second antibody to TGF-beta (BDA5; available from R.& D Systems) at 0.1 micrograms/ml for 2 hours, with anti-rabbit IgG peroxidase-conjugated antibody (available from -Sigma Chemical Co.) for 1 hour, and with the chromogenic substrate o-phenylenediamine (Sigma), made up according to manufacturer's instructions, for 15 minutes. Absorbances at 492 nm were converted into quantities of TGF-beta protein using a standard curve. Both conditioned media and standards were assayed in the presence of 10% FCS in DMEM. This assay was linear for TGF-beta concentrations in the range from 0.1 ng/ml to 20 ng/ml in the presence of 10% FCS in DMEM.

RNA Prevaration and Northern Analysis.

Total cytoplasmic RNA was isolated from cultured vascular smooth muscle cells as described in Kemp et al., *Biochem. J.*, 277: 285–288, 1991. Northern analysis was performed by lectrophoresis of total cytoplasmic RNA in 1.5% agarose gels in a buffer containing 2.2 M formaldehyde, 20 mM 3-(N-morpholino)propanesulfonic acid, 1 mM EDTA, 5 mM sodium acetate and 0.5 micrograms/ml ethidium bromide. The integrity of the RNA was checked by visualizing the gel under UV illumination prior to transfer onto Hybond N (available from Pharmacia LKB) as specified by the manufacturer. Filters were hybridized as described in Kemp et al., *Biochem. J.*, 277: 285–288, 1991, using a [$^{32}$P]-oligolabeled mouse TGF-beta probe corresponding to amino acids 68–228 in the precursor region of the TGF-beta polypeptide as set forth in Millan et al., *Development*, 111: 131–144.

Results.

Vascular smooth muscle cells from the aorta of adult rats proliferate with a cell cycle time of approximately 35 hours in DMEM+10% FCS (see, for example, Grainger et al., *Biochem. J.*, 277: 145–151, 1991). Addition of tamoxifen decreased the rate of proliferation with maximal inhibition at concentrations above 33 micromolar. 50 micromolar tamoxifen concentrations produced an increase in cell number (96 hours following the addition of serum) that was reduced by 66%+/-52% (n=3). The slower rate of proliferation was hypothesized to stem from a complete blockage of proliferation for a proportion of the vascular smooth muscle cells or from an increase in the cell cycle time of all of the cells. To distinguish between these possibilities, the proportion of the cells passing through M phase and the time course of entry into cell division were determined.

Quiescent vascular smooth muscle cells were stimulated with DMEM+10% FCS in the absence or presence of 33 micromolar tamoxifen, with the cell number being determined at 8 hour intervals by time lapse photomicroscopy. In the presence of ethanol vehicle alone, more than 95% of the vascular smooth muscle cells had divided by 40 hours, whereas there was no significant increase in cell number in the presence of tamoxifen until after 48 hours. By 64 hours, however, more than 90% of the cells had divided in the presence of tamoxifen. The time taken for 50% of the cells to divide after stimulation by serum was increased from 35+/-3 hours (n=7) to 54+/-2 hours (n=3) by 33 micromolar tamoxifen. Since tamoxifen did not significantly reduce the proportion of cells completing the cell cycle and dividing, inhibition of vascular smooth muscle cells caused by tamoxifen appears to be the result of an increase in the cell cycle time of nearly all (>90%) of the proliferating cells.

To determine whether tamoxifen increased the duration of the cell cycle of vascular smooth muscle cells by increasing the duration of the $G_0$ to S phase, the effect of tamoxifen on entry into DNA synthesis was analyzed. Tamoxifen at concentrations up to 50 micromolar did not significantly affect the time course or the proportion of cells entering DNA synthesis following serum stimulation of quiescent vascular smooth muscle cells (DNA synthesis between 12 hours and 24 hours after stimulation was measured by [$^3$H]-thynidine incorporation: control at 17614+/-1714 cpm; 10 micromolar tarnoxifen at 16898+/-3417 cpm; and 50 micromolar tamoxifen at 18002+/-4167 cpm). Since the duration of S phase is approximately 12 hours (unpublished data), tamoxifen does not appear to have significantly impacted the time course of entry into DNA synthesis. These results therefore imply that tamoxifen decreases the rate of proliferation of serum-stimulated vascular smooth muscle cells by increasing the time taken to traverse the $G_2$ to M phase of the cell cycle.

Based upon these results, it appeared that tamoxifen exhibited effects similar to those previously described for TGF-beta (see, for example, Assoian et al., *J. Cell. Biol.*, 109: 441–448, 1986) with respect to proliferation of sub-cultured vascular smooth muscle cells in the presence of serum. Tamoxifen is known to induce TGF-beta activity in cultures of breast carcinoma cell lines as described, for example, in Knabbe, et al., *Cell*, 48: 417–425, 1987. Consequently, experimentation was conducted to determine whether tamoxifen decreased the rate of proliferation of vascular smooth muscle cells by inducing TGF-beta activity. When quiescent vascular smooth muscle cells were stimulated with 10% FCS in the presence of 50 micromolar tamoxifen and 10 microgramns/ml neutralizing antiserum against TGF-beta, the cells proliferated at the same rate as control cells in the presence of ethanol vehicle alone.

To confirm that the vascular smooth muscle cells produced TGF-beta in response to tamoxifen, such cells were treated with tamoxifen for 96 hours in the presence of 10% FCS. The conditioned medium was then collected and TGF-beta activity was determined by the modified mink lung epithelial (MvLu) cell assay described above. Tamoxifen increased the TGF-beta activity in the medium by >50fold. Addition of tamoxifen (50 micromolar) in fresh DMEM+10% FCS to the MvLu cells had no effect on DNA synthesis, demonstrating that tamoxifen did not induce production of active TGF-beta by the MvLu cells.

TGF-beta is produced as a latent propeptide which can be activated outside the cell by proteases such as plasmin. To determine whether tamoxifen increased TGF-beta activity by promoting the activation of latent TGF-beta or by stimulating the production of the latent propeptide which was subsequently activated, the total latent plus active TGF-beta present in the conditioned medium was determined by sandwich EUISA as described above. After 96 hours in the presence of tamoxifen (50 micromolar), the total TGF-beta protein present was increased by approximately 4-fold. Furthermore, the proportion of the TGF-beta present in active form was increased from <5% in the medium conditioned on vascular smooth muscle cells in the presence of ethanol vehicle alone to approximately 35% in the medium conditioned on cells treated with tamoxifen. Thus, tamoxifen appears to increase TGF-beta activity in cultures of rat vascular smooth muscle cells by stimulating the production of latent TGF-beta and increasing the proportion of the total TGF-beta which has been activated.

Heparin increases TGF-beta activity in medium conditioned on vascular smooth muscle cells (unpublished data). The mechanism of action of heparin in this regard appears to involve the release of TGF-beta from inactive complexes present in serum, because pretreatment of serum with heparin immobilized on agarose beads is as effective as direct addition of free heparin to the cells. To determine whether tamoxifen acts to release TGF-beta from sequestered complexes in serum which are not immunoreactive in the ELISA assay, 10% FCS +DMEM was treated with 50 micromolar tamoxifen for 96 hours at 37° C. in the absence of cells. Medium treated in this way contained similar levels of TGF-beta protein and activity to untreated medium. It appears, therefore, that tamoxifen, unlike heparin, does not act by releasing TGF-beta from inactive complexes present in serum.

The content of TGF-beta mRNA was also analyzed by Northern analysis at various time points after addition of tamoxifen. Subcultured rat vascular smooth muscle cells (6th passage in exponential growth) in the absence or presence of ethanol vehicle alone contain very little mRNA for TGF-beta. By 24 hours after addition of tamoxifen (10 micromolar), TGF-beta mRNA was increased approximately 10-fold.

Although TGF-beta decreases the rate of proliferation of vascular smooth muscle cells, it does not affect the rate of proliferation of fibroblasts. Tamoxifen at concentrations of up to 50 micromolar did not reduce the rate of proliferation of subeultured adventitial fibroblasts. Tamoxifen is therefore a selective inhibitor of vascular smooth muscle proliferation with an $ED_{50}$ at least 10-fold lower for vascular smooth muscle cells than for adventitial fibroblasts.

EXAMPLE 2

Heparin Effect on VSMC Proliferation and Differentiation

Heparins.

An unfractionated, high molecular weight, anticoagulant pig mucosal heparin, fragments of heparin devoid of anticoagulant activity, and fragments of heparin with anticoagulant activity were tested. In addition, heparin coupled to agarose beads (Sigma Chemical Co., St. Louis, Mo.) was examined (see also Grainger et al., *Cardiovascular Res.* 27:2238–47, 1993).

Effect on Proliferation.

Freshly dispersed rat VSMC, prepared as in Example 1, were cultured in medium containing serum (as in Example 1) in the presence or absence of heparin. The cells were counted at intervals. Depending on the heparin used, the increase in cell number at 144 hours (when control cells enter stationary phase) was reduced by between 27±4.2% and 76±3.2% ($p<0.0005$ compared with cell number in control wells for all heparins tested). Although the effects of the heparins at 100 $\mu$g/ml were similar, there was a trend to greater effectiveness with increasing molecular size. The four heparins of 20 kD or above inhibited proliferation by 60–76%, and the four heparins of 12.6–3 kD inhibited proliferation by 27–45%.

Entry into Cell Cycle Phases.

Heparin had no effect on the entry of cells into S phase, as determined by growing the cells in the presence of 10 $\mu$M bromodeoxyuridine from 0–72 hours. Similar results were obtained when the cells were pulse-labeled with [$^3$H]-thymidine. The proportion of cells completing mitosis in the presence or absence of heparin was determined. Defined fields of cells were photographed at eight hour intervals by time lapse microscopy of gridded culture dishes. The grids were scored into the plastic on the inner surface so that the cells could not migrate into or out of the area being counted. In the absence of heparin,-92±1% of primary cells divided by 60 hours, but there was no detectable cell division in the presence of heparin until 72 hours. By 88 hours, however, 96±2% of the cells had divided in the presence of heparin. In the presence or absence of heparin, the time to complete mitosis was less than 3 hours. The total cell cycle times in the presence and absence of heparin were determined. The data showed that the major effect of heparin was to extend selectively the duration of $G_2$ to M phase of the cell cycle.

The concentration of heparin required to inhibit S phase entry decreased as the serum concentration was reduced. This observation is consistent with the removal by heparin of components of serum required for progression to S phase.

Heparin and TGF-beta.

To determine whether TGF-beta mediated the effects of heparin, anti-TGF-beta antibody (10 $\mu$g/ml; R&D Systems) was added. Anti-TGF-beta antibody alone had no effect on VSMC proliferation stimulated by 10% FCS. This antibody completed reversed the inhibition of VSMC proliferation observed when cells were incubated in the presence of heparin. Heparin coupled to agarose beads at an extracellular concentration of 100 µg/ml was as effective as free heparin (100 µg/ml) at inhibiting VSMC proliferation. Agarose beads alone at the same concentration had no effect These results are consistent with extracellular action of heparin on VSMC to inhibit proliferation. Further cell cycle studies indicated that heparin must be present within the first 12 hours of $G_1$ to inhibit VSMC proliferation.

Heparin and Smooth Muscle-Specific Myosin Heavy Chain Expression.

Previous studies demonstrated that primary VSMC in culture lose both the 204 kD (SM-1) and the 200 kD (SM-2) isoforms of SM-MHC, whether the VSMC are cultured in serum or in serum-free medium onto fibronectin. In primary cultures stimulated by serum, 100 µg/ml heparin substantially inhibited the loss of both SM-1 and SM-2 proteins in all cells, as assayed by direct immunoperoxidase staining or Western blotting (*Cell Tissues Res.* 257:1137–39, 1989; *Biochem. J.* 277:145–51, 1991). If the cells were plated in serum-free medium onto fibronectin, the normal loss of SM-1 and MS-2 proteins was unaffected by the presence of heparin. The effect of heparin in preventing the de-differentiation of primary VSMC in serum was completely reversed by the addition of anti-TGF-beta antibody (10 µg/ml), indicating that this heparin effect was also mediated by TGF-beta-like activity. Although heparin prevented the loss of smooth muscle-specific myosin heavy chain from primary VSMC in the presence of serum, it did not promote its reexpression. Moreover, heparin did not promote reexpression of SM-MHC in subcultured cells that exhibit very low levels of this protein. Thus, the effects of heparin and TGF-beta on the expression of SM-MHC in primary VSMC are similar.

EXAMPLE 3

Comparison of Enzyme-Dispersed and Explant-Derived Human VSMC

Materials.

Collagenase (C0130), elastase (E-0258), anti-rabbit IgG peroxidase-conjugated antibody, the chromogenic substrate orthophenylenediamine, and streptomycin sulfate were obtained from Sigma. Tamoxifen (free base) was purchased from Aldrich. Dulbecco's modified Eagle's Medium (D-MEM) and medium M199 were purchased from Flow Laboratories. 6-[$^3$H]-thymidine and the cell proliferation kit were obtained from Amersham International. Anti-TGF-beta antibodies (BDA19 and BDA47) were purchased from R&D Systems. EGF, PDGF-AA and PDGF-BB were obtained from Bachem, and were dissolved in filter-sterilized 25 mM Tris-HCl, pH 7.5, containing 1% fatty acid-free bovine serum albumin (BSA). Basic fibroblast growth factor and insulin-like growth factor 1 (N-mer) were obtained from Bachem and dissolved in sterile MilliQ water. Antiotensin II and endothelin 1 were obtained from Sigma and dissolved in sterile MilliQ water. TGF-beta (0.5 µg, lyophilized solid) was purchased from Peninsula, dissolved in 5 mM HCl to yield a 5 µg/ml stock, and diluted with PBS +0.2% BSA.

Human Aortic VSMC Cultures.

Adult human VSMC were obtained from 6 transplant donors (either sex, age range from 3 to 54 years) using the enzyme dispersal or explant technique. In one case, the same donor (a 24 year old male) was used to establish both an enzymedispersed (ED) and-explant-derived (EX) cell culture. Prior to enzyme-dispersion or explanting treatment, human aortas were obtained within 18 hours of death. The endothelium layer was removed with a scalpel blade and strips of smooth muscle cells (tunica media) were removed with forceps and chopped into small pieces (1 mm$^3$).

ED Cultures.

The aortic pieces were washed once with serum-free Hanks Balanced Salt Solution, then enzyme-dispersed with collagenase and elastase, as described in Example 1. The cells were plated at an initial density of 1.5×10$^5$ cells/cm$^2$ and incubated in a humidified atmosphere at 37° C. in 5% $CO_2$ in air. The cells were subcultured every 6–7 days (at stationary phase) by releasing them with trypsin/EDTA and diluting them 1:1.5 in D-MEM+10% FCS. Subcultured ED cells were cultured with D-MEM+20% FCS 24 h after plating, and thereafter at 48 hour intervals.

EX Cultures.

The aortic pieces were washed once with D-MEM+10% FCS, resuspended in a small volume of fresh D-MEM+10% FCS, and transferred to culture flasks or Petri dishes. The pieces were allowed to sediment onto the plastic and were evenly distributed (≈4 pieces/cm$^2$). Cells started to grow out from the explants after 3–7 days in culture. The aortic pieces were removed during the third week in culture, and the cells adhering to the plastic were allowed to grow to confluence for a further week. The cells were then subcultured every 4–5 days by releasing them with trypsin/EDTA and diluting them 1:2 in D-MEM+10% FCS. Subcultured cells were incubated with fresh D-MEM+20% FCS as described for ED cultures.

ED and EX subcultures were used between passage 5–20.

Cell counting, DNA synthesis assays and assays for total and active TGF-beta were performed as described in Examples 1 and 8.

Results.

ED and EX cultures prepared from the aorta of a single individual displayed distinct morphologies and growth characteristics. The EX culture proliferated much more rapidly than the ED culture. After 6 weeks of subculturing the ED and EX culture whenever confluence was attained, the total yield of cells was 4 fold higher per gram wet weight of aorta in the EX culture than the ED culture. The ED culture had a longer population doubling time in D-MEM+20% FCS (71±5 hours) than the EX culture (35±2 hours).

The VSMC in the EX culture were spindle-shaped and grew to confluence with a characteristic "hills and valleys" pattern at confluence. The EX culture VSMC reached stationary phase at a high saturation density (2.0–4.0×10$^4$ cells/cm$^2$). In contrast, the VSMC in the ED culture had a stellate morphology with numerous long cytoplasmic projections. They reached stationary phase at a low saturation density (0.7–2.0×10$^4$ cells/cm$^2$) without reaching monolayer coverage of the substrate. The VSMC in the ED culture contained high levels of both SM-MHC and a-actin, while the VSMC in the EX culture contained much lower levels of both of these protein markers.

The longer population doubling time of human ED cultures compared to ED cultures from the rat aorta is due to autocrine production of active TGF-beta. These human ED cultures produced 15.2±1.6 ng/ml total TGF-beta protein, of which 64±12% was in the active form. In contrast, the human EX cultures did not produce detectable amounts of TGF-beta. Medium conditioned for 48 hours on EX cultures during exponential growth contained <1 ng/ml total TGF-beta When TGF-beta production was compared using ED and EX cultures obtained from the same donor, the ED culture produced 8.5 ng/ml total TGF-beta, of which 57% was in the active form. The corresponding EX culture produced <1 ng/ml total TGF-beta protein.

Exogenous TGF-beta (10 ng/ml) was added to EX cultures 24 hours after subculturing and cell number was determined at 24 hour intervals. After 96 hours in the presence of exogenous TGF-beta, the increase in cell number was inhibited by 34±2%. The population doubling time of the EX cultures increased from 32±1 hour to 42±3 hours in the presence of exogenous TGF-beta.

Because the addition of exogenous TGF-beta extended the population doubling time of EX cultures by less than 12 hours, TGF-beta activity alone cannot account for the difference in population doubling time between the ED and EX cultures. Therefore, the fraction of cells that entered DNA synthesis in a 6 day period was compared using bromodeoxyuridine incorporation with a cell proliferation kit. The proportion of EX culture nuclei demonstrating bromodeoxyuridine incorporation after a 6 day pulse was 86±4%, but for ED culture cells was 48±4%. Therefore, the population doubling time of ED cultures was further increased over that of EX cultures, because less of the ED cells than the EX cells were cycling in the presence of D-MEM+20% FCS.

Tamoxifen IM inhibits proliferation of rat ED VSMC by inducing TGF-beta production with a half-maximal inhibition of proliferation at 2–5 $\mu$M TMX. Because human ED cultures already produce autocrine TGF-beta, the addition of TMX would not be expected to reduce the rate of VSMC proliferation further. To confirm this prediction, various concentrations of TMX (1 nM to 100 $\mu$M) or ethanol vehicle only (20 ppm to 0.2%) were added to the human VSMC for 96 hours, and the cell number was determined by cell counting. Concentrations of TMX >33 $\mu$M caused cell death, but concentrations below 10 $\mu$M did not affect the rate of proliferation.

EX cultures of human VSMC did not produce autocrine TGF-beta, so TMX would be predicted to inhibit VSMC proliferation. Concentrations of >33 $\mu$M TMX caused cell death in human EX cultures, as observed with human ED cultures. The half-maximal inhibitory dose for EX cultures was 30–100 nM TMX. At 5 $\mu$M TMX, the increase in cell number in human EX cultures was inhibited 33±8%.

To confirm these observations, quiescent EX cultures were restimulated and cultured for 96 hours in D-MEM+ 20% FCS containing TMX (0.5 $\mu$M) in the presence or absence of anti-TGF-beta antibody (25 $\mu$g/ml). The increase in cell number in the presence of TMX alone was inhibited by 27±2%, as compared to control cells incubated with ethanol vehicle alone. The presence of anti-TGF-beta antibody completely reversed the inhibition of proliferation due to TMX. ELISA assays for TGF-beta confirmed that medium conditioned on human EX cultures in the presence of 5 $\mu$M TMX contained 6.0±2.0 ng/ml total TGF-beta protein, of which 55±5% was activated.

The effect of heparin on proliferation of human ED and EX cultures was examined. Heparin IC86-1771, known to inhibit proliferation of rat ED VSMC by releasing a TGF-beta-like activity from serum, partially inhibited the proliferation of human EX cultures, but not ED cultures. At 100 $\mu$g/ml and at 48 hours after addition, heparin inhibited the increase in cell number in EX cultures by 51±10%; at 96 hours after addition, by 71±15%. In ED cultures at 96 hours after addition of 100 $\mu$g/ml heparin, the increase in cell number was inhibited by 8±5%. Anti-TGF-beta antibody did not abolish the ability of heparin to inhibit the proliferation of human EX cultured VSMC. Therefore, human EX VSMC may release more TGF-beta from 20% FCS than could be neutralized by added antibody, or heparin affected TGF-beta DNA synthesis as well as TGF-beta activation at the heparin concentrations tested.

The effect of mitogens on the entry of ED and EX cells into DNA synthesis was examined. Quiescent ED and EX VSMC were restimulated with either 20% FCS or 100 ng/ml PDGF-BB in D-MEM, and entry into DNA synthesis was monitored during successive 8 hour pulses using VH]thymidine. EX cells entered DNA synthesis in response to both mitogenic stimuli more rapidly than ED cells. The EX cells reached peak rate of DNA synthesis in response to FCS 16–24 hours after stimulation. The ED cells reached peak rate of DNA synthesis 24–32 hours after mitogenic stimulation.

Quiescent EX cells were then exposed to various mitogens, and stimulation of DNA synthesis was determined by incorporation of [$^3$H]thymidine 16–32 hours after stimulation. DNA synthesis was stimulated by 20% FCS by 8.0±1.5 fold, compared to control cells that remained in serum-free D-MEM throughout PDGF-BB and PDGF-AA caused a 3.0 fold stimulation of DNA synthesis. Insulin-like growth factor (IGF-1; 25 ng/ml) provided a 1.2 fold stimulation. However, epidermal growth factor (EGF; 100 ng/ml), basic fibroblast growth factor (bFGF; 100 ng/ml), TGF-beta (10 ng/ml), angiotensin II (AII; 100 nM) and endothelin-1 (ET-1; 100 nM) did not significantly stimulate DNA synthesis.

Quiescent ED cells were exposed to various mitogens, and stimulation of DNA synthesis was determined by [$^3$H] thymidine incorporation 1640 hours after stimulation. DNA synthesis was stimulated by 20% FCS by 25±6 fold, compared to control cells that remained in serum-free D-MEM throughout. PDGF-BB stimulated ≈3.0 fold, but PDGF-AA stimulated only 2.0 fold. The latter response was also variable (1 of 3 cultures did not respond to PDGF-AA), in contrast to the stimulation of EX VSMC. IGF-1 and EGF stimulated DNA synthesis 1.3 fold, and bFGF, TGF-beta, AII and ET-1 did not stimulate DNA synthesis.

EXAMPLE 4

TGF-beta and Transgenic apo(a) Mice

Apo(a) Mice.

Human apo(a) has been expressed in transgenic mice (*Nature* 360:670–72,1992), a species that normally lacks apo(a). These mice were used to study whether inhibition of TGF-beta activation, resulting in enhanced VSMC proliferation, represents a key step in atherogenesis.

Apo(a) transgenic mice, when fed a lipid-rich diet, develop vascular lesions similar to the fatty streak lesions in early human atherosclerosis. Immunoperoxidase labeling showed that apo(a) accumulated in the vessel wall at strongly staining focal regions in the luminal surface of the vessel. This phenomenon was studied using the more sensitive technique of immunofluorescence labeling.

Briefly, transgenic apo(a) mice, confirmed for the presence of the apo(a) gene by Southern blotting, and normal litter mates were obtained by continued crossing of transgenic mice with C57/B16×SJL hybrids. The heart and attached aorta were dissected out, immediately frozen in liquid nitrogen, embedded, and 6 $\mu$m frozen sections were prepared. The sections were fixed in ice-cold acetone for 90 seconds and stored at −20° C. until used. AU fluorescent labeling procedures were performed at 4° C. For apo(a) immunolabeling, sections were incubated with 3% BSA in Tris-buffered saline (IBS) for 30 minutes, then with sheep anti-human Lp(a) antibody that had been adsorbed against human plasminogen diluted 1:1000 in TBS containing 3% BSA. The anti-human Lp(a) antibody had no detectable cross-reactivity with mouse plasminogen. The bound primary antibody was detected using fluorescein-conjugated rabbit anti-sheep IgG diluted 1:80 in TBS containing 3% BSA, and visualized by fluorescence microscopy at 400× magnification ($\lambda$exc=440 nm; $\lambda$em=510 nm); photomicrographs were taken with 5 second exposures (ASA 1600). The tissue sections were indistinguishable whether the mice were fed a normal diet (Techlad, Madison, Wis.; 4% mouse/rat chow) or a lipid-rich diet containing 1.25% cholesterol, 7.5% saturated fat as cocoa butter, 7.5% casein and 0.5% sodium chelate.

Immunofluorescence labeling for apo(a) showed strongly labeled foci of apo(a) in the luminal surface of the aortic wall, but apo(a) was also labeled at a substantially lower intensity throughout the media of the vessel. No apo(a) labeling was detected in the aortic sections from the normal litter mate mice. The serum concentration of apo(a) in the transgenic mice was 3.8±1.2 mg/dl. Analysis of human arteries and of mice injected with radiolabeled apo(a) showed that plasma-derived apo(a) penetrates the vessel wall. In situ hybridization suggested that little, if any, apo(a) in the vessel wall of the apo(a) mice was derived from local synthesis.

Total and Activated Plasminogen.

Activation of plasminogen in the aortic wall was assayed using the specific inhibitor, $\alpha$2-antiplasmin ($\alpha$2-AP), which forms a stable covalent conjugate with active plasmin, but does not bind covalently to plasminogen, apo(a) or other proteins in the vessel wall. Briefly, $\alpha$2-AP (Sigma) was labeled with either fluorescein isothiocyanate (Sigma) or trimethylrhodamine isothiocyanate (*Exrerimentia* 16:430, 1960), and separated from unincorporated label by two gel filtrations on Sephadex G25.

For determination of activated plasminogen, sections were incubated for 16 hours with $\alpha$2-AP-FITC (1 $\mu$g/ml) and washed. For determination of total plasminogen, the sections were incubated with $\alpha$2-AP-FITC, as above, washed thoroughly in TBS containing 0.2% Nonidet-P40 (NP-40) and 300 mM NaCl (wash buffer), and then incubated with 1 mg/ml recombinant human tissue plasminogen activator (rTPA) in TBS for 3 hours to activate the plasminogen. The sections were washed, incubated for 16 hours with $\alpha$2-AP-TRITC (1 $\mu$g/ml), then washed thoroughly in wash buffer, followed by TBS. Bound labeled $\alpha$2-AP was visualized by fluorescence microscopy at 400× magnification ($\lambda$exc=440 nm; $\lambda$em=510 nm for FTIC label; $\lambda$exc=490 nm; $\lambda$em=580 nm for TRITC label). The low level of background autofluorescence from the acetone-fixed sections was subtracted for each section from the fluorescence of the label. There were no significant differences in the autofluorescence intensity either between sections from the same mouse aorta, or between normal litter mate aortic sections and those from transgenic apo(a) mice. Photomicrographs of bound $\alpha$2-AP-FITC to detect active plasmin were exposed for 10 seconds, and of bound $\alpha$2-AP-TRITC to detect plasminogen were exposed for 1 second (1600 ASA).

Quantitation of Fluorescence.

A Magiscan image analysis system (Joyce-Loebl) with extended linear range TV camera (Photonic Science) attached to a Nikon Diaphor inverted fluorescence microscope was used to quantitate the fluorescence. The gain control on the photomultiplier was set so that the average pixel value over the area of the vessel wall was between 2–5% of full scale. For each section, four fields of aortic wall were selected randomly under phase contrast (400× magnification), and separate fluorescence images were captured using filters for fluorescein and trimethylrhodamine. For TGF-beta and plasminogen/plasmin, the average pixel value for the fluorescence intensity over the whole area of the vessel media was calculated, and the mean for the four sections from each mouse (i.e., 16 fields of view) was computed. For osteopontin, the vessel media was only partly labeled, and only pixels with intensity values >5% of full scale were included in the calculation of average pixel value. The number of pixels ($\times 10^{-2}$) above the threshold is shown as the area labeled for osteopontin.

The $\alpha$2-AP-FITC was detected in aortic sections of both the normal and apo(a) mice, predominantly associated with the elastic laminae of the vessels. Quantitation of the fluorescent label showed approximately 3 fold less active plasmin in the vessel wall of the apo(a) mice than in the normal mice, regardless of whether the mice had been fed a lipid-rich or normal diet, as shown in Table 1.

TABLE 1

Quantitative fluorescent data

| | Normal Mice | | Transgenic apo(a) Mice | |
|---|---|---|---|---|
| | Normal Diet | Lipid-Rich | Normal Diet | Lipid-Rich |
| TGF-$\beta$ | | | | |
| Total | 112 ± 7 | 95 ± 12 | 115 ± 1 | 109 ± 6 |
| % Active Plasminogen | 90 ± 6 | 90 ± 5 | 36 ± 3* | 46 ± 8* |
| Total | 702 ± 47 | 748 ± 95 | 789 ± 121 | 688 ± 133 |
| % Active Osteopontin | 6.3 ± 1.3 | 6.1 ± 0.6 | 1.7 ± 0.7* | 1.9 ± 1.2* |
| Total | 1.4 ± 0.8 | 0.4 ± 0.1 | 32.3 ± 4.4* | 12.6 ± 2.1*+ |
| Area | 0.7 ± 0.9 | 1.2 ± 1.6 | 80.3 ± 0.0* | 103 ± 31.7*+ |

*p < 0.05 for apo(a) mice compared with normal litter mate mice
+p < 0.05 for apo(a) mice on a lipid-rich diet compared with apo(a) mice on a normal diet (Student's unpaired t-test)

Control experiments demonstrated that the $\alpha$2-AP-FITC bound only to active plasmin in the sections. No fluorescence was detected in aortic sections that were incubated with $\alpha$2-AP-FITC in the presence of a large excess (1 mU) of exogenous active plasmin. Aortic sections were also incubated with $\alpha$2-AP-FITC after treatment with the plasmin inhibitor, aprotinin (100 $\mu$g/ml), and no fluorescence was detected, demonstrating that there was no interaction of the label with the sections in the absence of active plasmin.

To assay for plasminogen, active plasmin was first labeled with $\alpha$2-AP-FITC, as described above, then the same sections were treated with rTPA to activate the plasminogen. The sections were relabeled for active plasminogen using $\alpha$2-AP-TRITC. When the rt-PA was omitted, no further staining for active plasmin with $\alpha$2-AP-TRITC was observed. Quantitation of the two fluorescent labels of active plasmin before and after activation of the plasminogen provides a measure of the total amount of plasminogen and of the proportion of plasminogen that was already activated in the sections (see Table 1). There was no significant difference in the total amounts of plasminogen in the sections from the apo(a) mice and normal mnice. In the normal mice, 6% of the plasminogen was activated to plasmin, compared with only 2% in the apo(a) transgenic mice. Thus, apo(a) inhibits plasminogen activation.

TGF-beta.

To determine whether the low plasmin concentration in the aortic wall of the apo(a) mice resulted in reduced activation of TGF-beta, immunofluorescent labels were used to quantitate active TGF-beta and total TGF-beta (active+ latent). Briefly, sections prepared as described above were labeled for total TGF-beta for 2 hours with 25 jig/ml of BDA47 (R&D Systems), a rabbit polyclonal antiserum to TGF-beta that detects isoforms 1 and 3 with equal sensitivity, but does not distinguish between latent and active TGF-beta. The sections were washed 3 times in TBS, and incubated with goat anti-rabbit IgG (Sigma; 1:50 dilution) conjugated with TRITC. Both antibodies were diluted in TBS containing 3% BSA. The same section was then washed 3 times in TBS and labeled for active TGF-beta with R2X (TGF-beta type II receptor extracelular domain, which recognizes the active form of isoforms 1 and 3 only) that was conjugated with FITC, as described above. Sections were incubated for 16 hours, then washed 3 times in PBS. Bound label was visualized by fluorescence microscopy, as described above. Photomicrograph exposures were 5 seconds (1600 ASA). To calibrate the fluorescence intensities of the two labels, a solution containing various proportions of active TGF-beta (6 ng/ml of total TGF-beta) was spotted on gelatin-polylysine-coated slides and allowed to dry at room temperature. The protein spots were labeled for total and active TGF-beta, as described for the aortic sections, and the fluorescence intensity ratios (TRITC/FITC) were determined. False color images of the proportion of TGF-beta in the active form were computed from the fluorescence ratios of the aortic sections using the calibration.

TGF-beta was present throughout the aortic media, predominantly associated with the elastic laminae in both the normal and apo(a) mice. No fluorescent label was bound to the sections when the primary anti-TGF-beta antibody was omitted. Quantitation of the fluorescent label showed no significant difference in the total amount of TGF-beta present in the aortic wall of normal and apo(a) mice (see Table 1).

Active TGF-beta was assayed using a truncated extracellular domain of the type II TGF-beta receptor fused to glutathione-S-trnnsferase (R2X) that had been FITC labeled. This label was detected in sections from both normal and apo(a) mice in association with the elastic laminae. In the presence of 100 mg/ml recombinant active TGF-beta-1, the binding of R2X-FITC to the sections was completely blocked. In addition, glutathione-S-tmnsferase labeled with FITC did not detectably bind to aortic sections from either normal or apo(a) mice.

The TGF-beta present in the aortic wall from apo(a) mice was significantly less active than the TGF-beta in the aortic wall from normal mice, irrespective of whether the mice had been fed a lipid-rich diet or normal diet (see Table 1). Thus, TGF-beta activation in the aortic wall is significantly inhibited by the presence of apo(a). Moreover, activation of TGF-beta is most strongly inhibited at the sites of highest apo(a) accumulation. Therefore, changes in the vessel wall that are a consequence of reduced TGF-beta activity will occur preferentially at the sites of focal apo(a) accumulation, but will not be dependent on the accumulation of lipid.

The mouse serum was also assayed for inhibition of TGF-beta activation by apo(a), using ELISAs for total and active TGF-beta (see Example 8). The total TGF-beta in the serum of apo(a) mice was 14.4±4.7 ng/ml; in normal mice it was 14.2±3.5 ng/ml. However, the proportion of total TGF-beta that was active in the serum of apo(a) mice was 34±19%, compared with 92±12% active TGF-beta in the serum of normal mice.

Osteopontin. Aortic sections were assayed for osteopontin, a marker of activated smooth muscle cells. Osteopontin was detected by incubating sections with monoclonal antibody MPIIIB $10_1$ (National Institute of Health Developmental Studies Hybridoma Bank) at 10 µg/ml in TBS containing 3% BSA for 16 hours. The sections were washed 3 times in TBS, and bound antibody was detected using goat anti-mouse IgG conjugated to fluorescein (Sigma F-2012; 1:50 dilution; 2 hours). Photomicrographs were obtained with 2.5 sec exposure time (ASA 1600).

Fluorescent labeling of osteopontin was detected in the aortic sections from apo(a) mice on either a lipid-rich or normal diet. Although a small increase in labeling for osteopontin was detected throughout the media of the aortae from transgenic apo(a) mice, very high levels of osteopontin labeling were co-localized with regions of focal apo(a) accumulation and very low TGF-beta activation. Treatment of apo(a) mice with bromodeoxyuridine for 24 hours before sacrifice showed no significant mitotic activity in the aortic media Thus, in the absence of physical injury, replication rates in atheromatous plaques are low, reflecting the slow growth of the lesions. Areas of aortic sections from normal mice that showed high proportions of active TGF-beta did not show detectable labeling for osteopontin. The total intensity and area of osteopontin labeling in the normal mouse sections were also very low compared with the apo(a) mouse sections. Therefore, the presence of apo(a) induces osteopontin expression in VSMC in the aortic wall, similar to the changes that occur during the development of vascular lesions, regardless of whether the mice are fed a lipid-rich or normal diet. Accumulation of lipid into the vessel wall under conditions where circulating lipid is elevated may be a consequence, rather than a cause, of the changes in VSMC activation marked by the expression of osteopontin. Previous studies have shown that activated VSMC in culture accumulate about 20 fold more lipid than contractile VSMC.

The results of these experiments link apo(a) to the inhibition of plasminogen and latent TGF-beta activation. The inhibition of TGF-beta activation likely contributes to the subsequent development of fatty lesions when apo(a) containing subjects (mice or human) are subject to a lipid-rich diet.

EXAMPLE 5

Tamoxifen Inhibits Migration and Lipid Uptake in VSMC in vitro and in Transgenic Mice Cell Culture.

Rat aortic VSMCs from 12–20 week old Wistar male rats were prepared by enzyme dispersion, as described in Example 1. The cultured cells were confirmed as >99% SMC by staining for SM-MHC, and proliferated with a cell cycle time of 36 h. Cells were passaged as described in Example 1, and were used either in primary culture or between passages 6–12.

Human aortic SMC from donors of either sex, aged 15–60, were prepared by explanting 1 $mm^3$ of medial tissue, as described in Example 3.

Migration.

Migration was assayed using SMC grown to confluence on glass coverslips. A defined injury is performed on the confluent layer of cells, which are allowed to recover in D-MEM+10% FCS for 24 hours. Bromodeoxyuridine (10 µM) is added between 18–24 hours, to label proliferating cells. Cells migrating past the boundary of the wound edge at 24 hours are detected by propidium iodide (PI) staining of the cell nuclei (500 µM PI in PBS+0.5% NP-40 for 30 min at room temperature): Cells that synthesized DNA were detected by antibody staining for bromodeoxyuridine using fluorescein-conjugated anti-bromodeoxyuridine antibodies. Migrating and proliferating cells in each field of view were simultaneously counted by image analysis of the rhodamine emission from PI and fluorescein emission from bromodeoxyuridine.

Lipid Uptake.

Cells in 24 well plastic dishes were incubated with serum-free-D-MEM for 24 hours or 1 hour at 37° C., then washed in PBS +1% BSA at 4° C. on ice for 30 minutes. Cells were incubated with $^{125}$I-labeled LDL at various concentrations for 3 hours in the presence or absence of cold competitor LDL. The cells were washed six times with ice-cold PBS, lysed in 0.1 M NaOH or 0.1% SDS, and cell-associated counts of LDL were determined by gamma counting.

Apo(a) Transgenic Mice.

Apo(a) [human 500 kD isoform] was expressed from the transferrin promotor in C57/B16×SJL F1 cross mice. Mice were sacrificed at 24 weeks of age after 12 weeks on a lipid-rich or normal diet Heart/lung/aortae frozen blocks were prepared, and 6 µm frozen sections prepared on gelatin-coated slides. Sections were either fixed in acetone for 90 seconds (for quantitative immunofluorescence; QIF) or in formaldehyde vapor for 18 hours (for histology). Sections were stored at −20° C. until analyzed.

Histology.

Sections were stained with trichrome stain or hematoxylin/eosin or oil red O/light green for lipid accumulation. Slides fixed in paraformaldehyde were rehydrated, incubated for 18 minutes in fresh oil red O, rinsed, and then incubated 1–2 minutes in fresh light green SF yellowish. The slides were then dehydrated, mounted, and the quantity and position of lipid deposition was analyzed by image analysis.

Quantitative Imnuunofluorescence (QIF).

Sections fixed in acetone were rehydrated in TBS+3% BSA for 30 minutes. The sections were incubated with primary antibody (anti-apo(a) immunosorbed on plasminogen, from Immunex, 1:1000 dilution; anti-total TGF-beta BDA47, from R&D Systems, 1:200 dilution; MBPIIIB $10_1$ anti-osteopontin antibody, from NHDSHB, 1:200 dilution) in TBS+3% BSA. Sections were washed 3×3 minutes in PBS, then incubated with fluorescent-labeled second antibody for 2 hours. After washing 3×3 minutes and mounting, bound fluorescence was quantitated by image analysis. Two markers could be examined on the same section using fluorescein and rhodamine as distinct fluorescent labels with different excitation and emission characteristics.

Active TGF-beta was localized and quantitated following incubation of slides with fluorescent-labeled extracellular matrix domain of the TGF-beta type II receptor (R2X), expressed in E. coli as a glutathione-S-transferase fusion protein.

Results.

When confluent cells were injured in the presence of serum, many cells migrated into the wound area within 24 hours. Proliferation was also stimulated under these conditions (7% of cells entered DNA synthesis, compared with 3% in an uninjured, control confluent culture). The addition of TGF-beta-1 (10 ng/ml) or tamoxifen (TAX; 10 µM) to rat cells at the time of wounding substantially inhibited migration (approximately 90% less cells crossed the boundary of the wound), consistent with previous data that demonstrated that TGF-beta inhibited SMC migration in Boyden Chamber assays. The inhibition of migration by TMX was reversed (>90%) by a neutralizing antibody to TGF-beta-1 (25 µg/ml).

In contrast, TGF-beta and TMX did not significantly inhibit the entry into DNA synthesis that was stimulated upon wounding. This observation is consistent with previous data that showed that TGF-beta and TMX slow SMC proliferation by extending the cell cycle in the $G_2$ phase, rather than by inhibiting or slowing entry into DNA synthesis.

These data agree with previous work that showed that apo(a) inhibits TGF-beta activation in culture, thereby promoting SMC migration. As described in Example 4, apo(a) stimulated VSMC proliferation. Apo(a) is associated with atherogenesis in man and in apo(a) transgenic mice. When apo(a) accumulates in conjunction with reduced levels of active TGF-beta, both migration and proliferation will increase. TMX, which stimulates formation of active TGF-beta, should ameliorate atherogenesis, regardless of whether migration or proliferation (or both) play key roles in pathogenesis.

In adult rat aorta SMC, LDL accumulation is very low, both in freshly dispersed cell preparations and in primary and secondary cultures. This phenomenon is due to very low levels of LDL receptors (200–400 receptors/cell), irrespective of whether the cells were exposed to lipoproteins.

In contrast, intimal SMC derived from rats 14 days after balloon injury to the carotid artery have a greater (≈5 fold) uptake of LDL, due to increased LDL receptor numbers (1500–2000 receptors/cell). When intimal cells or neonatal cells (displaying very similar properties) are treated with 10 ng/ml TGF-beta for 48 hours, these cells modulate, apparently irreversibly, to the adult phenotype. This phenotypic modulation is accompanied by a down-regulation of LDL receptors (≈800 receptorstcell), with a reduction of LDL uptake of >80%. The presence of TGF-beta may therefore reduce lipid accumulation by SMC.

The data obtained with apo(a) transgenic mice are consistent with this prediction. In these mice, apo(a) is accumulated at high levels at the intimal surface of the aorta. TGF-beta activation is strongly down-regulated from >80% in control aortas to <20% in apo(a) aortas. Lipid accumulation occurred at these sites in transgenic mice that were fed a lipid-rich diet and had elevated circulating LDL levels. Thus, reduced TGF-beta activity correlates with increased SMC S accumulation of LDL from the circulation. TMX, which is capable of elevating TGF-beta in vivo, may inhibit lipid accumulation in vivo.

EXAMPLE 6

Effect of Idoxifene on Cultured Human VSMCs

Cultures of human VSMCs were prepared either by enzyme-dispersal using collagenase and elastase or using the explant technique in which cells migrate out from pieces of aorta (about 1 mm$^3$) and proliferate, essentially as described in Example 3. Both enzyme-dispersed (ED) and explant-derived (EX) cultures were prepared from the aortae of two individuals, and either EX or ED cultures were prepared from eight additional donors. The two types of cultures have distinct morphologies and growth characteristics. The EX cultures proliferated much more rapidly than the ED cultures. After six weeks of culturing both types of cultures whenever confluence was attained, the total yield of cells was approximately 4 fold higher per gram wet weight of aorta in the EX cultures than the ED cultures. Consistent with this observation, the ED cultures had a longer population doubling time in DMEM+20% FCS (68±2 hours; n=6) than the EX cultures (35±2 hours; n=6), p<0.001.

Idoxifene (IDX) is an analog of TMX which has been reported to have enhanced anti-tumor activity (Chardler et al., *Cancer Res.*, 51, 5851 (1991); McCague et al., *Organic Preparation & Proc. Int.*, 26, 343 (1994)). The reduced side-effects of IDX compared with TMX and other TMX-related analogs have prompted the selection of IDX for comparison with TMX. IDX at 5 µM inhibited increase in cell number by 30% and 28% (two EX cultures tested) compared to control, while cell growth in the presence of 5 µM IDX and the neutralizing antibody to TGF-β (25 µg/ml) was 95±6% and 92±0% of control. In summary, both TMX and IDX inhibited cell growth of EX-derived, but not ED-derived, hVSMCs to a similar extent ($ED_{50}$=5, 10 and 100 nM; n=3 experiments) and this effect was reversible with the neutralizing antibody to TGF-β.

Despite the increasing use of animal models for vascular diseases, such as transgenic mice and balloon-induced injury models, cell culture models of human VSMCs remain important tools because of species-to-species variation. One problem associated with human cell culture models is the potential for variability in properties between individuals due to gender and age, as well as genetic and environmental differences. In this study, it was demonstrated that properties of VSMC cultures derived from ten different donors were very similar. The rate of proliferation, degree of differentiation indicated by expression of the contacile proteins SMa-α-actin and SM-MHC and response to growth factors of the smooth muscle cells were not influenced by the age or sex or genetic differences between the individuals.

By contrast, the method of establishing the VSMC culture had marked effects on the properties of the cells. VSMCs derived by the explant technique had a spindle shaped morphology, proliferated rapidly (doubling time of about 35 hours) and lost expression of the contractile protein SM-actin and SM-MHC in culture. VSMCs derived from the same individual by the enzymedispersal technique were larger, with stellate morphology, proliferated more slowly (doubling time of about 68 hours) and retained high levels of expression of the contractile proteins SMe-α-actin and SM-MHC throughout many (>20) passages in culture. It is therefore important when comparing cell culture studies of human VSMCs to take into account the method used to establish the cultures.

The mechanisms which underlie the differences between the two types of human VSMC culture were investigated. All of the differences investigated the potential role of TGF-β result from production and activation of TGF-β by the ED, but not EX cultures. Addition of a neutralizing antiserum to TGF-β to ED cultures altered the properties of the cells so that they resembled EX cells. Conversely, addition of active TGF-β to EX cells resulted in properties resembling ED cells. Furthermore, agents previously shown to inhibit rat VSMC proliferation by increasing TGF-β activity, such as TMX (Grainger et al., *Biochem. J.*, 294, 109 (1993)) and heparin (Grainger et al., *Cardiovas. Res.* 2, 2238 (1993)), inhibited the proliferation of EX but not ED cells.

A number of recent studies have demonstrated that reduced TGF-β activity is correlated with the development of atherosclerosis both in transgenic mouse models (Grainger et al., *Nature*, 370, 450 (1994)) and in man (Grainger et al., *J. Cell. Biochem.*, 18A, 267 (1994)). The mechanisms which control TGF-β production in the ED and EX human VSMC cultures may therefore provide important clues as to the regulation of TGF-β activity in vivo. One possibility is that the VSMCs in the ED and EX cultures come from sub-populations of the VSMCs in the vessel wall which differ in their ability to produce TGF-β. Evidence is accumulating for heterogeneity of VSMCs both in culture and in vivo and it will be informative to determine whether equivalent sub-populations exist in vivo by identifying a number of the genes which are differentially expressed between the two types of culture.

If a reduction of TGF-β activity plays a role in atherogenesis, then agents which elevate TGF-β activity, such as TMX, would be expected to reduce the incidence of myocardial infarction. The results described above indicate that TMX stimulates TGF-β production by human VSMC at 10–100 fold lower concentrations than for rat VSMCs. Since TMX was shown to dramatically reduce the incidence of fatal myocardial infarction in a recent study of 1500 women (McDonald et al., *Brit. Med. J.*, 303, 435 (1994)), it is possible that an increase in active TGF-β operating in an autocrine inhibitory loop, was responsible for these effects.

EXAMPLE 7

Tamoxifen Elevates TGF-β and Suppresses Diet-Induced Formation of Lipid Lesions in Mouse Aortae Treatment of Mice with TMX and Preparation of Aortic Sections Adult (8–12 weeks old) male C57B16 mice in groups were weighed then fed ad libitum either normal mouse chow (ICN/Flow), or a high fat diet containing 1.25% cholesterol, 7.5% saturated fat as cocoa butter, 7.5% casein and 0.5% sodium cholate, or high fat diet containing 15 µg TMX per gram, or high fat diet containing 1 µg TMX per gram. Water was freely available throughout. After three months on the respective diets, each mouse was re-weighed before sacrifice. The heart and attached aorta were embedded in Cryo-M-bed (Bright Instrument Co., Huntington, U.K.) and snap frozen in liquid nitrogen, then 4 µm frozen sections were prepared as described previously (Paigen et al., *Proc. Nat'l. Acad. Sci.*, 84, 3763 (1987); Paigen et al., *Cancer Res.* 45, 3850 (1985)). Platelet-poor plasma was prepared by adding blood taken at the time of death to one tenth volume of 3.5% w/v trisodium citrate on ice. After 15 minutes, the samples were spun (5,000×g; 15 minutes) and the plasma supernatant retained. In the experiment with 4 groups of 15 mice, the plasma from 9 mice from each group was pooled for analysis of the lipid profile of each group. Separate Faliquots from the remaining 6 mice in each group were stored at −20° C. until assayed.

Measurement of TGF-§ in Plasma and Aortic Wall Sections

The (a+1)TGF-β in serum or platelet-poor plasma was measured by ELISA as described above in Example 4. Active TGF-β was measured by ELISA using truncated extracellular domain of the type II TGF-β receptor (R2X). Active and (a+1)TGF-β were measured in 4 µm frozen aortic sections by quantitative immunofluorescence as described above in Example 4. Active TGF-β was measured using fluorescein-labelled R2X, (a+1)TGF-β was measured using BDA19 antiserum (R & D Systems).

Analysis of Livid Lesion Formation by Oil Red O Staining

For each mouse, 5 sections separated by 80 µm were fixed in 10% buffered formalin, stained with oil red O and counter stained with light green as described by Paigen et al., supra. The first and most proximal section to the heart was taken 80

μm distal to the point where the aorta became rounded. The area of oil red O staining in each section was determined with a calibrated eyepiece, excluding lipid droplets less than 50 μm², and the mean lesion area per section per mouse was calculated for each mouse and each group of mice. Regions of focal lipid staining >500 μm² were defied as lipid lesions, and the number of such lesions per section per mouse was determined.

Lipoprotein Profile Analysis

One ml of pooled, platelet-poor plasma from each group of mice was diluted to 4 ml with buffer A (0.15 M NaCl, 0.01% (w/v) sodium EDTA and 0.02% (w/v) sodium azide at pH 7.2) and ultracentrifuged at d=1.215 g/ml for 48 hours at 4° C. 0.5 ml of the 2 ml lipoprotein fraction (d<1.215 g/ml) was gel filtered through a sepharose 6B column by FPLC at room temperature. The column was eluted with buffer A at 0.4 ml/minute and fractions of 0.2 ml were collected and analyzed for cholesterol. Cholesterol was measured by the cholesterol oxidase method (Sigma Diagnostics) by adding S pi from each column fraction to 200 μl assay reagent in an EUISA plate (Maxisorp plates; Gibco). The assay plate was incubated at 37° C. for 15 minutes and absorbance read at 492 nm Serum for calibration containing 200 mg/dL total cholesterol (Sigma Diagnostics) was used to convert absorbance readings to cholesterol concentrations according to the manufacturer's instructions. The positions of elution of the major lipoprotein classes in mouse platelet-poor plasma under the conditions described have been determined previously (Yokode et al., *Science,* 250, 1273 (1990)). Fractions 1–9 contained the very low density lipoprotein (VLDL), fractions 10 to 19 contained LDL and fractions above 20 contained HDL.

Assays for Plasma Triglycerides, Cholesterol and Sex Hormones

Total plasma triglycerides was measured by the UV end-point glycerol kinase enzymatic method (Sigma Diagnostics). Total plasma cholesterol was measured by the cholesterol oxidase method (Sigma Diagnostics) performed in ELISA plate wells as described above. 17-β-estradiol was measured by a specific sandwich EBLSA assay (Cascade Biochemicals) and total testosterone plus dihydrotestosterone by radio-immunoassay (Amersham International). All blood parameters (apart from the lipoprotein profile) were performed on six individual platelet-poor plasma aliquots in each group of mice.

Measurement of SM-α-actin and Osteopontin in Vessel Wall Sections

Four μm frozen sections were prepared from the heart/aorta blocks stained with oil red O for lipid lesions. One section adjacent to each section stained for lipid was stained for smooth muscle xactin by quantitative immunofluorescence except that the mouse monoclonal antibody to smooth muscle a-actin, A-2547 (Sigma Chemical Co.), was used as the primary antibody at 1:2000 dilution. Fluorescein-labelled anti-mouse IgG (Sigma Chemical Co.) was used as the second antibody at 1:64 dilution. Osteopontin was measured in the next adjacent frozen section, using the mouse monoclonal antibody MBPIIIB 10 (NIH Developmental Studies Hybridoma Bank) labelled with biotin followed by fluorescein-labelled streptavidin.

Results

To determine the effects of TWX on TGF-β in the aortic wall and in circulation, an initial study was performed to establish an effective dose. Adult (8 week old) male C57B 16 mice (a strain of mice susceptible to lipid lesion formation on a high fat diet and which develop fatty streak lesions which resemble the early stages of atherosclerosis in man) in 3 groups were fed ad libitum for 28 days on either a normal mouse chow (low fat diet), or a high fat chow containing 0.5% sodium cholate and 5% cholesterol (high fat diet), or high fat diet containing 15 μg TMX (high TMX diet). The mice on the high TMX diet received an average of 1.1±0.3 mg/kg/day of TMX. Groups of 6 mice each were killed at intervals up to 28 days after starting the high TV diet. Active TGF-β and active plus acid activatable latent TGFβ [(a+1) TGF-β] in serum samples and in the aortic wall were determined as described in Example 8. The (a+1)TGF-β increased detectably after 3 days reaching a maximum increase of 2.8-fold in serum and 10-fold in the aortic wall and compared with control groups of mice on the high fat diet After 7 days, (a+1)TGF-β in both the vessel wall and in serum declined slowly, so that by 28 days, it was elevated by 2.4-fold in serum and 5.8-fold in the aortic wall. Active TGF-β also increased in response to the high TMX diet and the kinetics of the initial increases in active TGF-β were very similar to those for (a+1)TGF-β, reaching a maximum at 7 days, with more than 90% of the (a+1)TGF-β in serum and in the aortic wall was in the active form at 7 days after starting the high TMX diet. However, between 7 and 28 days, the increase in active TGF-β in both serum and in the aortic wall decline more rapidly than the (a+1)TGF-β so that after 28 days, active TGF-β was only elevated by 1.5-fold in serum and 2.2-fold in the aortic wall. The decrease in the proportion of active TGF-β after 7 days appears to be due to the induction of plasminogen activator inhibitor-i.

In a further experiment, adult (8 week old) C57B16 mice in 3 groups of 15 were fed on the diets described above, together with a fourth group of 15 mice fed a high fat diet containing 1 μg/g TMX (low TMX diet). The mice on the high TMX diet received an average dose of 1.1±0.3 mg/kg/day of TMX on the low TMX diet received 0.08 a 0.02 mg/kg/day. The remaining mice were killed after 3 months on the diets and the heart, lungs and aortae were embedded and snap-frozen in liquid nitrogen. Platelet-poor plasma was prepared from a terminal bleed. None of the mice in the 4 groups showed anatomical abnormalities, although the mice fed TMX at the high or low doses gained less weight during the period of the experiment than the mice on either the low fat or high fat diet (Table 2). The concentrations of both active and (a+1)TGF-5 in plasma and in the aortic wall were significantly increased by the high TMX diet. On the low TMX diet, only the active TGF-β in plasma did not show a significant increase (Table 2). The effects of TMX on TGF-β after 3 months of the high TMX diet were significantly lower than in mice treated for 28 days.

TABLE 2

Effects of High Fat Diet and Tamoxifen on C571B16 Mice

| | Low Fat | High Fat | Low TMX | High TMX |
|---|---|---|---|---|
| TMX (mg/kg/day) | — | — | 0.08 ± 0.02 | 1.1 ± 0.3 |
| Weight gain over 3 months (g) | 8 ± 2 | 9 ± 1 | 5 ± 2** | 2 ± 1*** |
| (a + 1)TGF-β Plasma (ng/ml) | 11 ± 4 | 12 ± 3 | 18 ± 5** | 22 ± 6*** |
| Vessel Wall (arbitrary units) | 22 ± 4 | 20 ± 2 | 32 ± 4** | 44 ± 8*** |
| Active TGF-β Plasma (ng/ml) | 8 ± 3 | 8 ± 2 | 10 ± 3 | 12 ± 3*** |

TABLE 2-continued

Effects of High Fat Diet and Tamoxifen on C571B16 Mice

|  | Low Fat | High Fat | Low TMX | High TMX |
|---|---|---|---|---|
| Vessel Wall (arbitrary units) | 20 ± 3 | 18 ± 4 | 28 ± 3** | 33 ± 5*** |
| Lesions per mouse[a] | 0.7 ± 0.1 | 3.6 ± 1.0* | 2.6 ± 0.8** | 1.1 ± 0.3*** |
| Lesion area/section/mouse ($\mu m^2$) | 230 ± 50 | 6860 ± 1480* | 4660 ± 960** | 823 ± 220*** |
| 17β-estradiol (ng/ml) | 0.28 ± 0.10 | 0.39 ± 0.14 | 0.40 ± 0.20 | 0.25 ± 0.08 |
| Total Testosterone (ng/ml) | 16 ± 2 | 14 ± 3 | 13 ± 5 | 11 ± 7 |
| Total Plasma Cholesterol (mg/dl) | 71 ± 2 | 92 ± 4* | 79 ± 3** | 83 ± 4*** |
| VLDL Cholesterol (mg/dl) | 4 | 30 | 38 | 42 |
| LDL cholesterol (mg/dl) | 8 | 33 | 27 | 27 |
| HDL-cholesterol (mg/dl) | 58 | 27 | 11 | 14 |
| Total Triglycerides (mg/dl) | 142 ± 15 | 109 ± 5* | 111 ± 9 | 204 ± 36*** |
| SM-α-actin (arbitrary units) | 146 ± 6 | 138 ± 8 | 168 ± 14 | 204 ± 12*** |
| Osteopontin (arbitrary units) | 2 ± 1 | 46 ± 16* | 30 ± 11 | 5 ± 3*** |

Serial sections from the aortic sinus region were analyzed for lipid lesions using the oil red O staining protocol and sectioning strategy as described by Paigen et al., supra. Small regions of luminal lipid staining were detected in mice on the low fat diet, but most of the vessel wall was devoid of lipid deposits in this group. In mice fed the high fat diet, there was a 5-fold increase in the number of lipid lesions in the aortic wall but in the mice fed the TMX diets, there was a dose-dependent decrease in the number of lesions with a 86% decrease of diet-induced lesions on the high TV diet (Table 2). The aortic wall area stained with oil red O was measured for each group of mice. Mice on the high fat diet had lesion areas (per section per mouse) of 6860±1480 $\mu m^2$ (n=15) consistent with previous published results (Emerson et al., *Am. J. Path.*, 142, 1906 (1993); Paigen et al., *Arteriosclerosis*, 10, 316 (1990)). The high TMX diet and low TMX diets reduced the lesion areas by 88% (n=15; p<0.001) and 32% (n=15; p<0.01) respectively (Table 2). TVX therefore causes a dose-dependent inhibition of diet-induced lipid lesions in C57B16 mice.

High or low TMX diets significantly lowered total plasma cholesterol by approximately 10% compared with mice on the high fat diet. Analysis of the lipoprotein profiles showed that for the mice on the low fat diet, most of the cholesterol was in the HDL fraction. After 3 months on the high fat diet, however, there was a marked increase in very low density lipoprotein (VLDL) cholesterol of approximately 7-fold (Table 2) and LDL cholesterol (4-fold) whereas the amount of cholesterol in the HDL fraction was reduced by approximately 50% (Table 2). The high and low TMX diets had only small effects on the amount of cholesterol in VLDL or LDL, but further reduced the HDL cholesterol by approximately 50% (Table 2), accounting for most of the overall reduction in cholesterol. In contrast to the decrease in total plasma cholesterol concentration caused by the high TMX diet, there was an increase in plasma concentration of triglyceride (Table 2).

The high or low TMX diets did not affect the very low plasma concentrations of 17β-estradiol in the male mice (Table 2). The mean total testosterone concentration (assayed as testosterone plus dihydrotestosterone) was not significantly altered by the TMX diets, although the range of testosterone concentrations was larger than in the mice on the high fat diet, suggesting that TMX may affect testosterone levels in individual mice. However, it is unlikely that changes in the levels of the primary sex hormones in response to TMX are responsible for the inhibition of lipid lesion formation. Medial smooth muscle cells in transgenic apo(a) mice which expressed osteopontin, a marker of deifferentiated smooth muscle cells, are the site of focal apo(a) accumulation and very low TGF-β activity. The accumulation of osteopontin occurred in mice on a low fat or high fat diets and was therefore independent of the accumulation of lipid at the sites of low TGF-β activity. In the C57B16 mice fed the high fat diet, sections adjacent to the lipid lesions identified by oil red O staining showed regions of high osteopontin accumulation, whereas there was almost no osteopontin accumulation in the aortic sections from mice on the high TmX diet. The type(s) of cells in the aortic wall (e.g., VSMCs, macrophages, etc.) from which the osteopontin was derived, were not identified. Similar experiments in which the accumulation of smooth muscle xactin was assayed showed an inverse pattern to that for osteopontin. There were regions of low SM-α actin expression in adjacent sections to lipid lesions, whereas the amount of SM-α actin was increased in the sections from mice on the high TMX diet. Similar results to those described above for C57B16 mice have been observed in the transgenic apo(a) mouse when these mice were fed a high fat diet. That is, both the lesion areas and number of lesions for both strains of mice were reduced by approximately 90%.

This example demonstrates that TMX strongly inhibits the formation of lipid lesions induced by a high fat diet in a susceptible strain of mice. The data show that a major effect of TMX in the C57B 16 mice is to elevate TGF-β in aortic wall and in circulation. This is consistent with previous evidence that TMX increases the production of TGF-β by VSMCs and other types of cells in vitro and in breast tumor cells in vivo. The suppression of osteopontin accumulation and the increase in SM-α actin in mice treated with TMX is consistent with previous observations on the apo(a) transgenic mouse (Example 4). These mice showed large accumulations of osteopontin at sites where focal accumulations of high concentrations of apo(a) result in decreased TGF-β activity in the vessel wall. The activation of the smooth muscle cell was also marked by a decrease in local SM-α actin concentration and occurred in the mice on a low fat diet in the absence of lipid accumulation. On a high fat diet, lipid accumulation occurred at the sites of apo(a) accumulation and lesions formed in two stages: activation of the VSMCs as a result of low TGF-β activity and subsequently uptake of lipid by the activated cells when the mice are subjected to a high fat diet. Thus, the cardiovascular protective effect of TV in mice may be due to elevation of TGF-β in the artery wall which prevents VSMC activation and consequently inhibits lipid accumulation on a high fat diet. TVX causes an overall 2-fold increase in active TGF-β in the aortic wall in C57B16 mice and a similar increase in apo(a) transgenic mice would restore the overall TGF-β concentration to that observed in normal littermate mice lacking the apo(a) gene. This hypothesis therefore predicts that TMX would prevent lipid lesion formation in apo(a) mice on a high fat diet. It is of interest that the cardiovascular protective effects of TMX against diet-induced lipid lesions in mice reported here were obtained at doses similar to those used in breast cancer therapy.

EXAMPLE 8

Determination of Active and Acid Activatable TGF-β in Human Sera, Platelets and Plasma by Enzyme-Linked Immunosorbent Assays Antibodies The antibodies to TGF-β used for the ELISAs were BDA19 (a chicken polyclonal IgY antibody which neutralizes TGF-β activity) and BDA47 (an affinty purified rabbit polyclonal IgG antibody), both obtained from R&D Systems (Oxford, U.K.). Goat anti-rabbit IgG coupled to horseradish peroxidase was obtained from Sigma Chemical Co. (Poole, U.K.). TGF-β standards were obtained from Peninsula (St. Helens, U.K; purified porcine TGF-β1) and Amersham International (Amersham, U.K.; recombinant human TGF-β1). To refer the ELISA data obtained with these TGF-β1s to the interim international standard, bovine TGF-β1 (89/516) was obtained from the National Institute of Biological Standards and Control (Potters Bar, U.K.). TGF-β2 and TGF-β3 isoforms were obtained from R&D Systems). The TGF-β standards were dissolved in 25 mM Tris/HCl pH 7.4 containing 50 μg/ml fatty acid free bovine serum albumin (FAF-BSA) to give 5 μg/ml stock solutions. The concentration of the standard TGF-β solutions was checked against the bioassay of DNA synthesis in MvLu epithelial cells (see below). Both TGF-β standards gave an $ED_{50}$ for inhibition of DNA synthesis in the MvLu bioassay of between 2–3 pM which agrees well with the previously reported value of 2 pmol/L (Danielpur et al., *J. Cell Physiol* 138, 79 (1989)).

Growth Factors

Platelet-derived growth factor (PDGF) AA and BB homodimers and epidermal growth factor (Bachem Inc., Saffron Walden, U.K.) were dissolved in 25 mmol/L Tris/HCl, pH 7.4 containing 1% FAF-BSA to give 0.3 μmol/L stock solutions. Basic fibroblast growth factor (0.56 μmol/L) interleukin 1β (0.59 μmol/L), transforming growth factor α (1.81 μmol/L), interferon γ (0.59 μmol/L) and insulin-like growth factor I (0.59 μmol/L; all from Bachem Inc.) were dissolved in sterile MilliQ water to give stock solutions of the concentrations indicated. Angiotensin II and endothelin I (Sigma Chemical Co.) were dissolved in sterile MilliQ water to give 10 μmol/L stock solutions.

Recombinant Expression of the TGF-β Type II Receptor

The extracellular domain of the TGF-β type II receptor was amplified from the vector H2 3FF (Lin et al., *Cell*, 68, 775 (1992)) using the polymerase chain reaction (PCR). The vector DNA was linearized with Not I, precipitated and resuspended at 10 ng/,L. Amplification was carried out in a 50 μl reaction containing 2.5 μl DNA, 5 μl 10× TAQ buffer (LKB Pharmacia; Upsalla, Sweden), 250 ng of each oligonucleotide primer (GAATTCCCATGGGTCGGGGGCTGCTC (SEQ ID NO: 1) and GAATTCGTCAGGATrGCIGGTGTT (SEQ ID NO:2); Wellcome Protein and Nucleic Acid Chemistry Facility, University of Cambridge), 1 U TAQ polymerase and a mixture of dATP, dTTP, dCTP and dGTP to give a final concentration of 200 μM for each nucleotide. The sample was overlaid with 50 μL paraffin oil. The reaction was carried out using a thermal cycler (PREM; Cambridge, U.K) for 30 cycles (denaturing at 94° C. for 1 minute, annealing at 55° C. for 2 minutes, elongation at 72° C. for 2 minutes).

The 450 bp fragment produced was purified by electrophoresis in low gel temperature agarose, digested with EcoRi and cloned into the glutathione-S-transferase fusion vector pGEX 2T (LKB Pharmacia). Vectors carrying inserts in the required orientation were identified by plasmid mapping. The sequence of the insert was checked by subeloning the 450 bp EcoRi fragment from the chosen clone (pGT1C) into Bluescript Ks+ followed by double strand sequencing. The sequence showed a single base change (C to A at position +13 from the initiation codon) compared to the published sequence (Lin et al., supra.) which introduces a leu to met mutation in the protein.

Protein Purification

An overnight culture of *E. coli* TG1 containing pGT1C was diluted 1:100 into fresh 2YT medium (500 mL) containing 270 μmol/L ampicillin a and grown to an $OD_{600}$ of 0.5. Production of the fusion protein was induced by addition of 1 mM isopropylthiogalactoside and the cells were harvested 5 hours later by centrifugation. The bacteria were resuspended in 50 mL phosphate buffered saline (PBS; 150 mmol/L NaCl, 2 mmol/L $Na_2HPO_4$, 4 mmol/L $Na_2HPO_4$, pH 7.3) containing 1% Triton X-100 and 1 mmol/L PMSF and lysed by sonication for S minutes. The lysate was centrifuged (10,000×g; 5 minutes) and the fusion protein was purified from the Supernatant by the one step purification method of Smith and Johnson (*Gene*, 67, 31 (1988)). FPLC of the purified glutathione-binding proteins on a Superdex 200HR column in 20 mM ammonium bicarbonate, pH 8.0, demonstrated that >95% of the protein present was the desired 43 kDa TGF-β receptor fusion protein.

ELISA to Measure Total TGF-β

Maxisorp 96 well ELISA plates (Gibco; Uxbridge, U.K.) were coated with the capture antibody by incubating with 50 μL BDA19 anti-TGF-β chicken IgY (40 μg/mL) diluted in Tris-buffered saline (MBS; 137 mmol/L NaCl, 50 mmol/L Tris/HCl, pH 7.4) and shaking the plates until dry by evaporation at room temperature (approximately 12 hours). The plates were washed 3×3 minutes with PBS, blocked with 350 μL 3% FAF-BSA in TBS for 1 hour, washed 3×3 minutes with TBS and incubated for 2 hours with 100 μL of test samples or dilutions of a TGF-β stock solution for calibration. The purified porcine TGF-β stock solution diluted in TBS to concentrations between 0.4 pmol/L and 4000 pmol/L was used for calibration unless otherwise indicated.

The plates were washed (3×3 minutes) with TBS+3% FAF-BSA+0.1% Triton X-100 (wash buffer) and incubated with 20 μL detection antibody (BDA47; anti-TGF-β (rabbit IgG)) at 1 μg/mL in wash buffer for 1 hour. The plates were rinsed with wash buffer (3×3 minutes) and incubated with an antibody against rabbit IgG conjugated to horseradish peroxidase (Sigma A6154) at 1:2500 dilution in wash buffer for 1 hour. After washing (3×3 minutes with wash buffer), the plates were incubated for 15 minutes with the chromogenic substrate orthophenylenediamine (Sigma) according to the manufacturer's instructions. The reaction was stopped by addition of an equal volume of 3M HCl and the absorbances read on an ELISA plate reader (Titertek Multiscan; Flow Laboratories, High Wycombe, U.K) within 15 minutes of stopping the reaction. Absorbances were converted into quantities of TGF-β protein using the calibration curve from the TGF-β standard.

ELISA to Measure Active TGF-β

This ELISA was performed as for the ELISA to assay total TGF-β except: (i) the ELISA plates were coated with the purified TGF-β receptor fusion protein using 20 μL of a 50 μg protein per mL of solution in TBS and (ii) the detection reagent (BDA47) was used at 5 μg/mL.

Mink Lung Epithelial DNA Synthesis Bioassay

Mink lung epithelial cells (MvLu; American Type Culture Collection; passage 49–60) were subcultured at 1:5 dilution in DMEM+10% FCS. After 24 hours, the medium was replaced with DMEM+10% FCS containing the sample (<1% v/v) or standards in the presence and absence of neutralizing antiserum to TGF-$\beta$ (BDA19) at 10 $\mu$g/ml. DNA synthesis during a 1 hour pulse of 6-[$^3$H]-thymidine (5 $\mu$Ci/ml; Amersham International) was determined 23 hours after addition of test medium. TGF-$\beta$ activity was calculated as the proportion of the inhibition of DNA synthesis which was reversed in the presence of neutralizing antibody, using a standard curve to convert the inhibition values into quantities of active TGF-$\beta$. Purified porcine TGF-$\beta$ diluted in TBS was used as the standard unless otherwise indicated.

Preparation of Conditioned Culture Media, Human Platelets, Platelet-Poor Plasma and Serum Medium (DMEM+20% FCS) was conditioned for 24 hours on cultures of adult human aortic VSMCs obtained by enzymatic dispersion of aortic media as described above.

Twenty mL of peripheral venous blood was collected from 12 healthy male volunteers (aged 23–54); 10 mL were aliquoted immediately into tubes containing 1.1 mL of sterile 3.8% (w/v) trisodium citrate in MilliQ water at room temperature. The samples were centrifuged (250×g; 15 minutes) to remove red blood cells. Apyrase (Sigma) was added to the platelet-rich plasma to a final concentration of 100 mg/L to prevent platelet degranulation; PMSF (1 mmol/L) and aprotinin (1 mg/L) were added to prevent proteolytic activation or degradation of TGF-$\beta$. These samples were centrifuged (700×g; 15 minutes) and the supernatant platelet-poor plasma was separated from the platelet pellet The platelet-poor plasma was kept at room temperature until assayed by ELISAs within 2 hours of preparation or was stored in 0.5 mL aliquots at −80° C. The platelet pellet was resuspended in 10 mL (i.e., the original volume of blood) of a buffered saline solution (145 mmol/L NaCl, 5 mmol/L KCl, 10 mmol/L glucose, 10 mmol/L MgSO$_4$, 0.5 mmo/L EGTA, 1 mmol/L PMSF, 1 mg/L aprotinin, 10 mmol/L HEPES, pH 7.4) and recentrifuged as before. The washed platelet pellet was resuspended in 10 mL of buffered saline solution and the platelet concentration was determined by hemocytometer. Platelets were lysed by ultrasonication until <10% of unlysed platelets were detected by hemocytometer. Human platelet suspensions were also obtained form the Blood Transfusion Service, Cambridge, U.K The platelets were collected by centrifugation (3,000×g; 3 minutes) and approximately 0.1 g of platelets were resuspended in 0.5 mL MilliQ water and lysed by three cycles of freeze-thawing. The membrane fragments were removed by centrifugation (14,000×g; 10 minutes) and the supernatant was mixed with an equal volume of 2×TBS.

The remaining 10 mL of freshly drawn blood samples were dispensed immediately into polypropylene tubes and allowed to clot at room temperature for 2 hours. The clotted samples were centrifuged (1,000×g; 4 minutes), the serum was removed and either stored on ice until assayed within 2 hours or stored at −80° C. until assayed. The clot was washed three times by centrifugation (1000×g; 4 minutes) in 5 mL of 150 mM phosphate buffer, pH 7.0, and the third wash was retained for TGF-$\beta$ assays. The washed clot was dissolved in 5 mL of 150 mM phosphate buffer, pH 2.0, for 30 minutes, then neutralize by addition of 5 mL of 150 mM phosphate buffer, pH 12.0. The samples were assayed for TGF-$\beta$ immediately or stored in 1 mL aliquots at −80° C.

All blood-derived samples, stored at −80° C., were not thawed until assayed. The initial freeze-thaw cycle resulted in less than 10% loss of total or active TGF-$\beta$ activity in the ELISAs. However, three additional freeze-thaw cycles of samples containing TGF-$\beta$ in active or latent form was sufficient to cause loss of approximately 90% activity.

Bioassays of PDGF

PDGF was bioassayed by its mitogenic activity on human VSMCs derived by explant as described previously (Kocan et al., *Methods in Cell Biology,* eds. Harris, C. C., Trump, B. F., and Stenes, G. D., Academic Press (1980)). VSMCs were made quiescent by incubation in serum-free DMEM for 48 hours. Samples of serum or platelet-poor plasma were added at a final concentration in DMEM of 5% or 20%, respectively. DNA synthesis was assayed by [$^3$H]-thymidine (Amersham International; 5 $\mu$Ci/mL) incorporation between 12 hours and 36 hours after addition of the test samples to the cells. The proportion of DNA synthesis due to PDGF was estimated by the addition of polyclonal antibody (50 mg/L) which neutralizes all forms of PDGF to replicate cell samples.

Results

An ELISA was set up to detect total ($\alpha$+1) TGF-$\beta$ using the polyclonal chicken IgY antibody BDA19 as the capture reagent. The assay detected purified porcine TGF-$\beta$ in TBS in the range of 4 pmol/L to 2000 pmol/L with half-maximal change in absorbance ($\Delta A_{50\%}$) of 280±80 pmol/L (n=7). Using recombinant human TGF-$\beta$1 in TBS, the assay detected TGF-$\beta$ in the range 8 pmol/L to 2000 pmol/L with a $\Delta A_{50\%}$ of 320±120 pmol/L (n=3). Direct comparison of the TGF-$\beta$1% (R&D Systems) was made with the interim international bovine TGF-$\beta$ (89/516). An ampoule of 89/516 containing 1500 units (approximately 80 ng protein; 32 pmol) was dissolved in sterile water to 800 $\mu$l and serially diluted in TBS and similar dilutions of the R&D Systems TGF-$\beta$1 made. Comparison of the calibration curves showed that a nominal 1.0 pmol at R&D TGF-$\beta$1 had an activity of 130±8 units.

To test the specificity of the capture antibody in the total TGF-$\beta$ assay, it was replaced with nonimmune chicken IgY (R&D Systems). The change in absorbance in the presence of 4000 pmol/L of purified porcine TGF-$\beta$1 was less than 5%, i 15 indicating that TGF-$\beta$ binding under the assay conditions was specific to the capture agent.

To test whether the ELISA detected acid activatable, latent forms of TGF-$\beta$, a sample of human platelets from the blood bank was lysed and assayed before and after activation of the TGF-$\beta$ (Wakefield et al., *J. Biol. Chem.,* 263, 7646 (1985); Assoian et al., *J. Cell Biol.,* 102, 1031 (1986)). The latent TGF-$\beta$ was converted to active TGF-$\beta$ by addition of 5% vol/vol 150 mmol/L sodium phosphate buffer at pH 2.0 for 5 minutes, then neutralized by addition of 5% vol/vol 150 mmol/L sodium phosphate buffer at pH 12.0 (Barnard et al., *Biochim Biophys. Acta,* 1032, 79 (1990)). Control samples were treated with 10% vol/vol 150 mmol/l sodium phosphate buffer at pH 7.0. The MvLu cell bioassay of the untreated and acid-treated platelet lysate showed that the amount of active TGF-$\beta$ was increased 5.1-fold after acid activation of the latent TGF-$\beta$, indicating that approximately 80% of the TGF-$\beta$ present in the unactivated sample was in the acid activatable, latent form. When assayed by the total TGF-$\beta$ ELISA, the control aliquot contained 680±80 pmol/L TGF-$\beta$ (n=3) by ELISA and the acid-activated aliquot contained 600± 120 pmol/L TGF-$\beta$ (n=3). These results show that the total TGF-$\beta$ ELISA does not distinguish between active and acid activatable TGF-$\beta$ from human platelets.

The precise conditions for activation of the small and large complexes of latent TGF-$\beta$ have not been characterized and there is some evidence for the existence of two pools of latent TGF-β which differ in the conditions required for activation. Therefore, TGF-β is defined as that pool of latent TGF-β which is acid-activatable by the treatment described above (i.e., exposure to pH 2.0 for 5 minutes before neutralization to pH 7.0 without overshoot). Longer exposure to pH 2.0 did not significantly affect the concentration of activated TGF-β and it remains to be determined which form(s) of latent TGF-β are activated under the defined conditions.

A second ELISA was established to measure active TGF-β in the presence of latent TGF-β using a truncated TGF-β type II receptor protein fused to glutathione-S-transferase as the capture reagent. This assay detected purified porcine TGF-β1 in TBS in the range of 20 pmol/L to 4000 pmol/L with a $\Delta A_{50\%}$ of 680±160 pmol/L (n=4) and recombinant human TGF-β1 in -TBS in the range of 40 pmol/L to 4000 pmol/L with a $\Delta A_{50\%}$ of 720±120 pmol/L (n=3). To test the specificity of the truncated receptor fusion protein as the capture agent, it was replaced with glutathione-transferase. The change in absorbance in the present of 4000 pmol/L of purified porcine TGF-β1 was less than 5%, indicating that TGF-β binding was specific to the capture agent under the assay conditions.

To confirm that the active TGFT ELISA did not detect acid activatable, latent TGF-β, samples of human platelet TGF-β before and after acid activation were assayed. The active TGF-β ELISA gave 160±40 pmol/L (n=3) in the unactivated sample and 640±80 pmol/L (n—3) TGF-β in the acid-activated sample, consistent with the data obtained from the (α+1) TGF-β ELISA and the MvLu cell bioassay described above. The ability of the ELISA to discriminate between active and latent TGF-β was further defined in studies on TGF-β in fresh human platelets (see below).

To test the reproducibility of both ELISAs, 24 aliquots of a sample of lysed human platelets from the blood bank was assayed simultaneously by both assays. The value for active TGF-β was 200 pmol/L with a coefficient of variation of 7.4% and the corresponding value for (α+1) TGF-β was 640 pmol/L with a coefficient of variation of 6.8%. Further aliquots of the same platelet lysate were also analyzed blind by four independent operators using both ELISAs on eight separate occasions. The inter-assay coefficient of variation was 13.2% for the active TGF-β assay and 12.2% for the (α+1) TGF-β assay.

The relative sensitivity of each ELISA to the three isoforms of TGF-β was determined. Recombinant human TGF-β1, TGF-β2 and TGF-β3 (400 pmol/L) in TBS were assayed using each ELISA, expressing the absorbance for TGF-β2 and TGF-β3 as a percentage of the absorbance for TGF-β1. Both ELISAs detect TGF-β1 and TGF-β3 with similar sensitivity, but TGF-β2 was detected with approximately 10-fold less sensitivity than the other isoforms in the (α+1) TGF-β ELISA and 100-fold less sensitivity in the active TGF-β ELISA. The relative sensitivities for the isoforms in the active TGF-β ELISA are qualitatively consistent with the relative TGF-β isoform affinities of the type II TGF-β receptor (Massagué, *Ann. Rev. Cell Biol.*, 6, 597 (1990)). The slightly greater relative sensitivity of the active TGF-β ELISA to TGF-β3 than the (α+1) TGF-β ELISA would result in an overestimate of the proportion of active TGF-β in a sample which was composed mostly of TGF-β3 if the assays were calibrated using a TGF-β1 standard. The proportion of active TGF-β in samples containing only the TGF-β2 isoform cannot be determined accurately by these ELISAs at concentrations below 4000 pmol/L. The concentration of TGF-β2 in human serum has been reported as <5 pmol/L (Danielpur et al., *Annals N.Y. Acad. Sci.*, 593, 300 (1990)).

The cross-reactivity of both ELISAs to a variety of other peptide growth factors was determined at concentrations which have a maximal biological effect in cell culture. Neither assay gave a change of greater than 5% in absorbance in response to PDGF-AA (3.3 nmol/L), PDGF-BB (3.3 nmol/L), basic fibroblast growth factor (5.6 nmol/L), epidermal growth factor (15.9 nmol/L), insulin-like growth factor I (1.3 nmol/L), angiotensin II (100 nmol/L), endothelin I (100 mnol/L), interleukin 1i (588 pmol/L), transforming growth factor a (1.8 mmol/L), or interferon γ (588 pmol/L).

There are several reports that TGF-β binds to serum components and extracellular matrix components with high affinity. For example, McCaffrey and co-workers demonstrated that TGF-β associates non-covalently with the major serum protein, α2-macroglobulin (*J. Cell Biol.*, 109, 441 (1986)). However, preparation of the TGF-β standard solutions in the presence of 1.4 μmol/L human α2-macroglobulin or 10% FCS did not affect the $\Delta A_{50\%}$ by more than 10% compared with the $\Delta A_{50\%}$ for the standard TGF-β solutions diluted in TBS in either ELISA. Therefore, any non-covalent interactions formed between TGF-β and α2-macroglobulin or with components of FCS do not prevent active TGF-β from binding to the type II TGFP receptor in the active TGF-β ELISA or to the capture antibody in the (α+1) TGF-β ELISA, nor do they inhibit binding by the detection antibody. It has been noted in a previous report that purified TGF-β and α2-macroglobulin may not interact in the same way as endogenous serum TGF-β and α2-macroglobulin (O'Conner-McCorua et al., *J. Biol. Chem.*, 262, 14090 (1987)).

The active TGF-β concentration was measured in three samples of medium (DMEM containing 10% FCS) conditioned for 24 hours on human VSMCs which produce active TGF-β. The values obtained with the active TGF-β ELISA were compared with those obtained using the MvLu cell bioassay (Table 3).

TABLE 3

| | Active TGF-β concentration in medium conditioned on human VSMCs Active TGF-β (pM) | |
|---|---|---|
| Sample | MvLu Assay | Active TGF-β ELISA |
| 1 | 584 ± 24 | 552 ± 32 |
| 2 | 356 ± 32 | 400 ± 24 |
| 3 | 488 ± 40 | 484 ± 16 |

The amount of active TGF-β present in three different samples of DMEM + 20% FCS which had been conditioned on human VSMC cultures for 24 hours was determined in quadruplicate using the DNA synthesis bioassay in MvLu epithelial cells and the active TGF-β ELISA.

The results obtained by the two assays were not statistically different for any of the three samples tested (p=0.88, 0.48 and 0.99, using students unpaired t-test). Thus, the ELISA gives values for active TGF-β concentrations in conditioned medium which are closely consistent with the MvLu cell bioassay used previously. Where possible, it is important to demonstrate consistency between the active TGF-β ELISA and the bioassay for conditioned media and other biological fluids. For example, it has recently been reported that direct addition of conditioned media to ELISA microwells can lead to inaccurate measurement of TGF-β for reasons that are not fully understood (Danieipur, *J. Immunol. Methods.* 158, 17 (1993)). Protocols which activate and concentrate TGF-βs to partially purify the samples and exchange the buffer were recommended (Danielpur, supra).

Another factor which might interfere with the assays is any peroxidases present in serum which bind to the capture reagents. To test for peroxidases, the capture antibody in the (α+1) TGF-β assay was replaced with non-immune chicken IgY, and the truncated receptor fusion protein in the active TGF-β assay was replaced with glutathione-S-transferase. The change in absorbance in either assay was less than 5% in the presence of either DMEM containing 10% FCS or human serum from donors A, E, K, or N in Table 5. These data indicated that any peroxidase activity in FCS or human serum did not significantly affect the assays of (α+1) or active TGF-βs.

TABLE 4

Active and (α + 1) TGF-β concentrations in human sera

| | TGF-β (pmol/L) | | | |
|---|---|---|---|---|
| | Unactivated serum | | Acid-activated serum | |
| Donor | Active | (α + 1) | Active | (α + 1) |
| A | <40 | 240 | 240 | 240 |
| B | 120 | 120 | 120 | 120 |
| C | 200 | 320 | 320 | 320 |
| D | 240 | 240 | 240 | 240 |

Serum samples from four male donors were assayed in a single experiment for active and total TGF-β by the ELISAs before and after acid activation. All samples were assayed in quadruplicate.

The above experiments suggested that the ELISAs could be used to measure TGF-β in human serum and the use of the assays for sera was therefore characterized. It was found that the calibration curves for both the active and (α+1) TGF-β assays were not affected when purified porcine TGF-β was added to human serum (donor E in Table 5) which contained very little TGF-β by either ELISA.

TABLE 5

(α + 1) and active TGF-β concentrations in human serum samples

| | TGF-β (pmol/L) | | |
|---|---|---|---|
| Donor | Active | (α + 1) | % active |
| E | <20 | <4 | — |
| F | <20 | <4 | — |
| A | <20 | 240 | <8 |
| G | 20 | 80 | 25 |
| H | 80 | 80 | 100 |
| I | 80 | 80 | 100 |
| J | 80 | 120 | 66 |
| K | 160 | 1120 | 14 |
| C | 280 | 320 | 88 |
| L | 320 | 320 | 100 |
| M | 360 | 320 | 113 |
| N | 1400 | 1400 | 100 |

Serum samples from 12 male donors aged between 23 and 54 were assayed immediately after preparation for active and (α + 1) TGF-β by the ELISAs described. All samples were assayed in quadruplicate by each ELISA in a single experiment.

For human sera comparisons of active TGF-, concentrations by the ELISA and the MvLu cell bioassay were not possible because human serum inhibited MvLu DNA synthesis by a mechanism independent of TGF-β. The presence of 10% (v/v) serum from any of 4 donors (A, H, J, and K in Table 5) inhibited DNA synthesis in MvLu cell cultures by more than 95%. This inhibition was not reversed by the presence of neutralizing antibodies to TGF-β, indicating that the human sera contained an inhibitor of DNA synthesis in MvLu cells which masked any effect of TGF-β. The MvLu cell bioassay cannot therefore be used to determine the concentration of active TGF-β in unfractionated human serum samples.

Alternative approaches were therefore required to validate the ELISA assays for direct use with human serum. The main requirement was to determine whether human sera contain non-TGF-β components which significantly affected the TGF-β concentrations estimated by either assay. Overestimated values of TGF-β would be obtained if a serum component was bound specifically or nonspecifically by the capture agent in either assay and was also recognized by the detection antibody or by the antibody to rabbit IgG linked to horseradish peroxidase. Alternatively, underestimated values would result if a serum component competed with TGF-β for the capture agent in either assay but was not recognized by the detection antibody. In a previous study in which TGF-β in unfractionated serum (after transient acidification) was determined by a radio-receptor assay, it was found that components in the serum interfered with the assay (O'Connor-McCourt et al., *J. Biol. Chem.*, 262, 14090 (1987). This resulted in a dilution curve which was not parallel to the standard dilution curve and estimates of TGF-β were 20 to 40 times lower than those obtained by acid-ethanol extraction of the same samples. Thus, it is possible that serum components which result in either over-estimated or underestimated TGF-β values in our ELISAs would also interfere with other assays (receptor binding or radio-immunoassays) used to validate serum TGF-β concentrations estimated by the ELISAs. Therefore, a more rigorous test for interfering components in serum was required. This was achieved by determining whether the concentrations of active and (α+1) TGF-β concentrations in sera were internally consistent before and after activation of latent TGF-β by acid treatment. Only under very implausible circumstances would consistent accounting of active and (α+1) TGF-β be obtained in the presence of serum components which interfered with either or both assays.

ELISAs of (α+1) and active TGF-β concentrations were performed on the sera from 4 male donors before and after the sera were acidified to pH 2.0 and neutralized to pH 7.0 as described for the lysed human platelet samples. For each of the sera in Table 4, there was no difference within the accuracy of the assays between the amount of (α+1) TGF-β before and after acid treatment. Furthermore, after acid treatment, the amount of active TGF-β was not significantly different from the amount of (α+1) TGF-β. These results imply that it is very unlikely that the sera tested contained components which interfered with either TGF-β ELISA since they would cause significant imbalances in the quantitative accounting of the amounts of active and (α+1) TGF-β before and after acid treatment. The use of acid treatment of the sera and reassay of the active and (α+1) TGF-β concentrations therefore provides an important internal control for the TGF-β assays when used directly for sera or complex biological fluids.

The sera from 12 male donors (aged 23 to 54) were assayed for active and (α+1) TGF-β by the ELISAs (Table 5). The mean (α+1) TGF-β concentration was 330 pmol/L, but the variation was very large (range less than 4 pmol/L to 1400 pmol/L). Similarly, the mean active TGF-β concentration was 230 pmol/L, and the range was from less than 20 pmol/L to 1400 pmol/L. The proportion of the (α+1) TGF-β present which was active ranged from <10% to 100% with a mean of 73% for the samples for which percent activation could be determined. These data for the amount of TGF-β in human serum can be compared with several previous reports. A value of 4.2±0.7 pmol/L (n=10) active TGF-β was obtained using the IL-4 dependent HT-2 cell proliferation assay (Chao et al., Cytokine, 3, 292 (1991)). However, when the serum was treated with acid, an increase of greater than 100-fold in TGF-β values was detected by the same proliferation assay. This implies a mean value for activatable (i.e., (α+1)) TGF-β of >420 pmol/L. In an earlier study (O'Connor-McCourt et al., supra.) using both a two-step competitive radio-receptor assay and the NRK cell-soft agar growth system, it was reported that acidethanol extraction of serum (FCS, calf and human) gave (α+1) TGF-β concentrations of 200–1000 pmol/L. A value for human serum for TGF-β1 of 1,300 pmol/L and <5 pM for TGF-β2 measured by specific ELISAs has also been reported (Dasch et al., Annals N.Y. Acad. Sci., 593, 303 (1990)). Of these data, only the low active TGF-β value of 4.2±0.7 pmol/L (n=10) differs substantially from the range of our ELISA values for human sera (Chao et al., supra).

Platelet-poor plasma samples were prepared from the same blood samples used to prepare sera from the 4 donors in Table 4. There was no difference within the accuracy of the assays between the amount of (α+1) TGF-β before or after acid treatment of the plasma samples, and after acid treatment, the amount of active TGF-β was not significantly different from the amount of (α+1) TGF-β (Table 6).

TABLE 6

Active and (α + 1) TGF-β concentrations in human platelet-poor plasma

| | TGF-β (pmol/L) | | | |
|---|---|---|---|---|
| | Unactivated plasma | | Acid-activated plasma | |
| Donor | Active | (α + 1) | Active | (α + 1) |
| A | <40 | 240 | 240 | 240 |
| B | 120 | 120 | 120 | 120 |
| C | 160 | 320 | 320 | 320 |
| D | 200 | 240 | 240 | 280 |

Platelet-poor plasma were derived from the same blood samples as the sera for Table 4 and were assayed in the same experiment for active and (α + 1) TGF-β by ELISA before and after acid activation. All samples were determined in quadruplicate.

These data demonstrate that the plasma did not contain components which interfered with either ELISA, consistent with the finding for the sera derived from the same blood samples.

Comparison of the data in Tables 4 and 6 also shows that (α+1) TGF-β concentrations and the proportions of TGF-β which were active were very similar in serum and platelet-poor plasma prepared from the same blood samples. These data implied that either the platelets had degranulated to release their TGF-β during the preparation of the platelet-poor plasma so that the amounts of TGF-β were the same in plasma and in serum, or that platelet degranulation during clotting in the preparation of serum did not release active or latent TGF-β into the serum. The serum and plasma TGF-β concentrations would then be similar because the serum and plasma did not contain a significant amount of active or latent TGF-β from platelets which had degranulated after drawing the blood samples.

To examine whether the active or latent TGF-β in the serum and plasma samples was derived from degranulation of platelets after drawing blood, (α+1) TGF-β concentrations in the sera, acid-extracted clots, platelet-poor plasma and platelets from seven donors were compared (Table 7).

TABLE 7

(a + 1) TGF-β concentrations in human serum, plasma, platelets, and acid-treated clots

| | (α + 1) TGF-β (pmol/L) | | | |
|---|---|---|---|---|
| Donor | Serum | Platelet-poor plasma | Platelets | Acid-treated clot |
| E | <40 | 40 | 1000 | 960 |
| N | 80 | 80 | 880 | 760 |
| B | 120 | 120 | 1000 | 1200 |
| D | 280 | 280 | 1600 | 1600 |
| A | 320 | 360 | 1200 | 1200 |
| C | 440 | 440 | 1000 | 720 |
| M | 1200 | 1400 | 760 | 760 |

Serum, platelet-poor plasma and platelets were prepared from blood from 7 male donors. Clots were removed from the serum samples by centrifugation, washed, dissolved by acidification and neutralized. TGF-β was released from platelets by sonication which lysed >90% of the platelets present. (α + 1) TGF-β in each sample was assayed by ELISA in quadruplicate. TGF-β concentrations for platelets and clots are calculated for the volume of blood from which they were derived.

The (α+1) TGF-β concentrations in serum and plasma derived from the same blood samples were very similar, consistent with the data in Tables 4 and 6. The average concentration of (α+1) TGF-β from the degranulated platelet samples was 1063 pmol/L and the average platelet concentration by hemocytometer in the platelet preparations was $3.0 \times 10^{11}$/L, equivalent to an average of 2,100 molecules of TGF-β per platelet. This may be compared with a previous estimate of 500 to 2,000 molecules of TGF-β per platelet recovered from "platelet secretate" (Wakefield et al., J. Biol. Chem., 263, 7646 (1988)). However, the surprising observation was that the (α+1) TGF-β concentrations of the degranulated platelets and the acid-extracted clots derived from the same blood samples were very similar. This observation implies that any active or latent TGF-β released by platelets which degranulated in the clots was almost entirely retained within the clot, since quantitative recovery of the (α+1) TGF-β was obtained from the clot after acid treatment. The retention of (α+1) TGF-β in the clot would account for the close similarity of the (α+1) TGF-β concentrations in the sera and plasma and this conclusion was tested further as described below. However, it should be noted that the data do not preclude the possibility that platelets contain substantial amounts of latent TGF-β informs which are not detected by the (α+1) TGF-β ELISA because they are not activated by the defined acid-activation procedure.

No active TGF-β could be detected in the platelet releasate from freshly prepared platelets, unlike the TGF-β obtained from blood bank platelets. When active recombinant human TGF-β1 was added to the platelet releasate containing the highest concentration of (α+1) TGF-β (1600 pmol/L) from donor D), the calibration curve for active TGF-β was superimposed on the curve for the recombinant human TGF-β1 in TBS. These observations show that the selectivity of the active TGF-β assay is at least 50-fold greater for active TGF-β1 than latent TGF-β1.

The mean value for (α+1) TGF-β in platelet-poor plasma was 389±177 pmol/L (n=7). Some of the reported values of TGF-β in platelet-poor plasma are similar to those described here. In two separate studies using acid-ethanol extraction of-platelet-poor plasma and the MvLu cell bioassay, TGF-β concentrations of 212±132 pmol/L (n=9) and 244±40 pmol/L (range >80 to <400 pmol/L; n=10) were recently reported. Previously, Wakefield et al. (supra.) reported that human plasma contains significant levels of TGF-β (60 i 24 pmol/L;

n=10) and concluded that latent TGF-β does circulate in normal individuals (*J. Clin. Invest.*, 86, 1976 (1990)). One much lower value of 2.3 pmol/L (range 2.1 to 2.7 pmol/L; n—9) for TGF-β1 in platelet-poor plasma assayed by a TGF-β1 ELISA on acid-ethanol extracts has also been reported (Anderson et al., *Kidney International*, 40, 1110 (1991)).

The similarity of both the (ac+l) and active TGF-β concentrations in platelet-poor plasma and serum from the same donor (Tables 4, 6, and 7) prompted the question of whether the TGF-β had been released by a partial degranulation of platelets when the blood samples were drawn and before the onset of clot formation in the serum samples. Since PDGF is contained in the same platelet a-granules as latent TGF-β, a bioassay for PDGF activity as a mitogen for human VSMCs was used to determine the extent of platelet degranulation during the preparation of the platelet-poor plasma (Table 8).

TABLE 8

Mitogenic indices of human serum and plasma on human vascular smooth muscle cells

| Donor | Mitogenic index | |
|---|---|---|
| | Serum | Plasma |
| B | 45 | 0.7 |
| H | 52 | 1.4 |
| C | 60 | 0.9 |
| D | 65 | 1.0 |
| A | 83 | 1.2 |

DMEM containing 5% serum or 20% platelet-poor plasma from five male donors was added to quiescent. explant-derived human smooth muscle cells and DNA synthesis was assayed in triplicate by incorporation of [$^3$H]-thymidine between 12 hours and 36 hours after addition of the samples. The mitogenic indices are the ratios of $^3$H counts incorporated in the test cell samples to $^3$H counts in control cells treated with medium alone (1,506 ± 123 cpm). The mitogenic indices for the plasma samples were unaffected by neutralizing antiserum to PDGF but were reduced by more than 52% for each of the serum samples.

Platelet-poor plasma had no significant mitogenic activity on human VSMCs measured as a ratio of [$^3$H]-thymidine incorporation in the presence or absence of plasma (Table 8) and the ratio was unaffected by neutralizing antibody to PDGF. However, addition of 3.3 pmol/L PDGF to the plasma samples caused an increase in the average mitogenic index from 1.0 to 1.6 and this increase was blocked by neutralizing PDGF antibody. The platelet-poor plasma samples therefore contained less than 3.3 pmol/L of active PDGF. In contrast, the human serum samples gave large mitogenic indices of 45 to 83 for the same cell preparation and at least 52% of the mitogenic activity was reversed by neutralizing antibody to PDGF (50 mg/L).

This mitogenic activity attributable to PDGF is consistent with previous estimates that PDGF accounts for approximately 50% of plateletderived mitogenic activity of human serum, as assayed on glial cells or fibroblasts (Singh et al., *J. Cell Biol.*, 95, 667 (1982)). The mitogenic stimulation reversible by neutralizing PDGF antibody (50 mg/L) in the serum samples corresponds to concentrations of human PDGF of greater than 300 pmol/L and less than 600 pmol/L in the human sera. This value may be compared with a reported concentration of PDGF in human serum of 500 pmol/L by radio-receptor assay (Heldin et al., *Exp. Cell. Res.*, 136., (1981)). A serum concentration of greater than 300 pmol/L therefore implies degranulation of most of the platelets during clot formation to release PDGF into the serum under conditions in which the TGF-β remains associated with the clot. The undetectable PDGF activity in the plasma samples indicates that the amount of PDGF in the plasma corresponds to degranulation of less than 5% of the platelets after bleeding.

Most previous work has shown that normal human plasma contains undetectable levels of PDGF. However, in one report (Heldin et al., supra.), PDGF in human platelet-poor plasma was estimated at 33 pmoVL by radio-receptor assay with a corresponding serum concentration of 500 pmol/L. Thus, the preparation of platelet-poor plasma contained little or no detectable PDGF from platelet degranulation during preparation in our experiments is consistent with previous data.

Taken together, these observations strongly imply (i) that the TGF-β in platelet-poor plasma and serum do not result from platelet degranulation which occurs on or after taking the blood samples and (ii) that the concentrations of (α+1) TGF-β in serum and plasma are very similar because platelet degranulation on clotting does not release (α+1) TGF-β into the serum which can be detected by the (α+1) TGF-β assay. Similar (α+1) TGF-β concentrations in serum were obtained from repeated bleeds from the same donors. For example, donor A gave (α+1) TGF-β concentrations of 240, 240, 320, 240, and 280 pmol/L from five bleeds at intervals of at least seven days. Furthermore, similar proportions of (α+1) TGF-β were active in repeated bleeds from the same donors. These observations are consistent with negligible platelet degranulation after the blood samples are drawn since degranulation would be unlikely to be sufficiently controlled to yield reproducible amounts of (α+1) TGF-β in sera prepared from separate bleeds.

The data leave open the question of the origin -of the TGF-β in platelet-poor plasma It is generally assumed that the plasma TGF-β is mainly derived from platelets and although plausible, this has not been demonstrated experimentally. However, the ELISAs described here should facilitate analysis of the mechanisms controlling platelet-poor plasma concentrations of active and (α+1) TGF-β. They should also allow examination of correlations between TGF-β concentrations in plasma or serum and various diseases in which TGF-, may be implicated.

All publications, patents and patent applications are incorporated herein by reference, except to the extent that the definitions in prior applications and patents are inconsistent with the definitions herein. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A theraputic method comprising treating non-aortal procedural vascular trauma comprising administering to a mammal, subjected to said procedural vascular trauma, an effective cytostatic antiproliferative amount of a structural analog of tamoxifen, or a pharmaceutically acceptable salt thereof.

2. The method of claim 1 wherein the structural analog of tamoxifen is droloxifene, idoxifene, 4-iodotamoxifen, 3-iodotamoxifen, raloxifene, toremifene, or a pharmaceutically acceptable salt thereof.

3. The method of claim 1 wherein the administration is before or after said procedure, or both before and after said procedure.

4. The method of claim 1 wherein the administration is in a series of spaced doses.

5. The method of claim 1 wherein the administration is parenteral.

6. The method of claim 1 wherein the administration is oral.

7. The method of claim 1 wherein the administration is systemic.

8. The method of claim 1 wherein the analog of tamoxifen or the salt thereof is administered via a sustained release dosage form.

9. The method of claim 1 wherein the administration is localized at the site of the vascular trauma.

10. The method of claim 1 wherein the procedure is organ transplantation.

11. The method of claim 10 wherein the organ is kidney.

12. The method of claim 10 wherein the organ is a liver.

13. The method of claim 1 wherein the procedure is a biopsy.

14. The method of claim 1 wherein the procedure is thrombectomy.

15. The method of claim 1 wherein the procedure is a vascular bypass graft.

16. The method of claim 1 wherein the cells comprise ocular tissue.

17. A therapeutic method comprising inhibiting vascular smooth muscle cell proliferation comprising administering to a mammal an effective cytostatic antiproliferative amount of a compound selected from the group consisting of tamoxifen, a tamoxifen analog, a pharmaceutically acceptable salt of tamoxifen, and a pharmaceutically acceptable salt of a tamoxifen analog, wherein the administration is by placement of a vascular shunt or intravascular stent comprising the compound.

18. The method of claim 17 wherein the compound is droloxifene, raloxifene, toremifene, tamoxifen, idoxifene, or a pharmaceutically acceptable salt thereof.

19. The method of claim 17 wherein the shunt or stent matrix is impregnated with the compound.

20. The method of claim 19 wherein the shunt or stent comprises a coating incorporating the compound.

21. The method of claim 17 wherein the shunt or stent comprises a coating incorporating the compound.

22. The method of claim 19, 20, or 21 wherein said matrix or said coating is biodegradable.

23. The method of claim 1 wherein the procedure is vessel anosthomosis.

* * * * *

UNITED STATES PATENT AND TRADEMARK OFFICE
CERTIFICATE OF CORRECTION

PATENT NO. : 6,262,079 B1
DATED : July 17, 2001
INVENTOR(S) : David J. Grainger, James C. Metcalfe, Lawrence L. Kunz, Robert W. Schroff and Peter L. Weissberg It is certified that error appears in the above-identified patent and that said Letters Patent is hereby corrected as shown below:

Title page,
Item [57], ABSTRACT, delete "$R^4FR^5$," and insert -- $R^4$, $R^5$, --, therefor.

Column 2,
Line 55, delete "—" after "production".

Column 7,
Line 53, insert --. -- between "R" and "McCaque".

Column 8,
Line 20, delete "1,2,3,4–tetrahydrohthalene," and insert -- 1,2,3,4–tetrahydronaphthalene, --, therefor.
Lines 20-21, delete "2–phenylhydroxy–1,2,3,4" and insert -- 2-phenyl-6-hydroxy-1,2,3,4- --, therefor.
Lines 21-22, delete "1-t4M(2-pyol-N-ylethoxy)-phenyl]" and insert -- 1-[4-(2-pyrrol-N-ylethoxy)-phenyl] --, therefor.
Line 22, delete "2-phenylmethoxy-3," and insert -- -2-phenyl-6-methoxy-3, --, therefor.
Line 23, delete "diydronaphthalene" and insert -- 4-dihydronaphthalene --, therefor.
Lines 23-24, delete "1-[4(2,3(hydroxypropoxy) phenyl]" and insert -- 1-[4-(2,3-dihydroxypropoxy)phenyl] -- therefor.
Line 25, delete "4dihydronaphthalene" and insert -- 4-dihydronaphthalene --, therefor.
Line 65, delete "mr,NA" and insert -- mRNA --, therefor.

Column 13,
Line 15, delete "-" between "stimulators)" and "that".
Line 38, insert -- be -- after "then".

Column 17,
Line 41, delete "thedosage" and insert -- the dosage --, therefor.

UNITED STATES PATENT AND TRADEMARK OFFICE
CERTIFICATE OF CORRECTION

PATENT NO. : 6,262,079 B1
DATED : July 17, 2001
INVENTOR(S) : David J. Grainger, James C. Metcalfe, Lawrence L. Kunz, Robert W. Schroff and Peter L. Weissberg It is certified that error appears in the above-identified patent and that said Letters Patent is hereby corrected as shown below:

Column 18,
Line 67, delete "14" and insert -- 1-4 --, therefor.

Column 19,
Line 13, insert -- . -- after "agent" and insert ¶ beginning with "The local…".
Line 53, insert -- . -- after "form".
Line 62, delete "-" after "in".

Column 20,
Line 3, delete "rat" and insert -- rats --, therefor.
Line 36, delete "PICA" and insert -- PTCA --, therefor.

Column 24,
Line 2, insert -- . -- after "TGF– beta".

Column 25,
Line 30, insert -- . -- after "sera" and insert ¶ beginning with "In another…".
Line 32, delete "type I" and insert -- type II --, therefor.
Line 55, delete "(HVSMC)" and insert -- (hVSMC) --, therefor.

Column 26,
Line 29, delete italics of "277:145-151, 1991".
Line 41, delete "403408" and insert -- 403-408 --, therefor.
Lines 47-48, delete "DMBM+10%.FCS" and insert -- DMEM+10%FCS --, therefor.

UNITED STATES PATENT AND TRADEMARK OFFICE
CERTIFICATE OF CORRECTION

PATENT NO. : 6,262,079 B1
DATED : July 17, 2001
INVENTOR(S) : David J. Grainger, James C. Metcalfe, Lawrence L. Kunz, Robert W. Schroff and Peter L. Weissberg It is certified that error appears in the above-identified patent and that said Letters Patent is hereby corrected as shown below:

Column 27,
Line 1, delete "gddded" and insert -- gridded --, therefor.
Line 18, delete "Wobum" and insert -- Woburn --, therefor.
Line 45, insert "-" between "96" and "well".
Line 46, delete "B3DA19" and insert -- BDA19 --, therefor.
Line 47, delete "2 micrograms/cm" and insert -- 2micrograms/cm$^2$ --, therefor.
Line 53, delete "." after R.
Line 55, delete "-" after "from".

Column 28,
Line 2, delete "lectrophoresis" and insert -- electrophoresis --, therefor.
Line 57, delete "tarnoxifen" and insert -- tamoxifen --, therefor.

Column 29,
Line 21, insert -- - -- between ">50" and "fold".
Line 32, delete "EUISA" and insert -- ELISA --, therefor.

Column 30,
Line 42, insert ¶ beginning with "The proportion…".
Line 48, delete -- - -- after "heparin," and insert -- had -- after "cells".

Column 31,
Line 5, insert -- . -- after "effect".
Line 42, delete "(C0130)" and insert -- (C-01030) --, therefor.

Column 32,
Line 55, delete "a-actin" and insert -- ∝-actin --, therefor.
Line 66, insert -- . -- between "beta" and "When".

UNITED STATES PATENT AND TRADEMARK OFFICE
CERTIFICATE OF CORRECTION

PATENT NO. : 6,262,079 B1
DATED : July 17, 2001
INVENTOR(S) : David J. Grainger, James C. Metcalfe, Lawrence L. Kunz, Robert W. Schroff and Peter L. Weissberg It is certified that error appears in the above-identified patent and that said Letters Patent is hereby corrected as shown below:

Column 33,
Line 5, insert -- the -- after "and".
Line 24, delete "IM" and insert -- (TMX) --, therefor.

Column 34,
Line 10, delete "VH]thymidine" and insert -- [$^3$H]thymidine --, therefor.
Line 22, delete "a3.0" and insert -- a≈3.0 --, therefor.
Line 32, insert -- - -- between "16" and "40".

Column 35,
Line 1, delete "(IBS)" and insert -- (TBS) --, therefor.
Line 35, delete "Exrerimentia" and insert -- Experimentia --, therefor.

Column 36,
Line 64, delete "mnice" and insert -- mice --, therefor.
Line 65, delete "6%" and insert -- ≈ 6% --, therefor.

Column 37,
Line 7, delete "jig/ml" and insert -- µg/ml --, therefor.
Line 41, delete "trnnsferase" and insert -- transferase --, therefor.
Line 46, delete "tmnsterase" and insert -- transferase --, therefor.

Column 38,
Line 20, insert -- . -- after "media".

Column 39,
Line 38, delete "Imnuunofluorescence" and insert -- Immunofluorescence --, therefor.
Line 44, delete "NHDSHB" and insert -- NIHDSHB --, therefor.

UNITED STATES PATENT AND TRADEMARK OFFICE
CERTIFICATE OF CORRECTION

PATENT NO.   : 6,262,079 B1
DATED        : July 17, 2001
INVENTOR(S)  : David J. Grainger, James C. Metcalfe, Lawrence L. Kunz, Robert W. Schroff
               and Peter L. Weissberg It is certified that error appears in the above-identified patent and that said Letters Patent is hereby corrected as shown below:

Column 40,
Line 38, delete "(≈800 receptorstcell)", and insert -- (≈800 receptors/cell) --, therefor.

Column 41,
Line 7, delete "Chardler" and insert -- Chandler --, therefor.
Line 32, delete "Sma-∝-actin" and insert -- SM–∝–actin --, therefor.
Lines 40-41, delete "SM-actin" and insert -- SM–∝–actin --, therefor.
Line 42, insert -- - -- between "enzyme" and "dispersal".
Line 45, delete "e" after "SM".

Column 42,
Line 53, delete "TGF-§" and insert -- TGF-β --, therefor.

Column 43,
Line 20, delete "Spi" and insert -- 5µI --, therefor.
Line 21, delete "EUISA" and insert -- ELISA --, therefor.
Line 40, delete "EBLSA" and insert -- ELISA --, therefor.
Line 51, delete "xactin" and insert -- ∝-actin --, therefor.
Line 53, delete "a-actin" and insert -- ∝-actin --, therefor.

Column 44,
Line 4, delete "15µg" and insert -- 15µg/g --, therefor.
Line 7, delete "TV" and insert -- TMX --, therefor.
Line 28, delete "inhibitor-i" and insert -- inhibitor-1 --, therefor.
Line 43, delete "(a+1)TGF-5" and insert -- (a+1)TGF-β --, therefor.
Line 52, in the title of Table 2, delete "C571B16" and insert -- C57B16 --, therefor.

UNITED STATES PATENT AND TRADEMARK OFFICE
CERTIFICATE OF CORRECTION

PATENT NO. : 6,262,079 B1
DATED : July 17, 2001
INVENTOR(S) : David J. Grainger, James C. Metcalfe, Lawrence L. Kunz, Robert W. Schroff and Peter L. Weissberg It is certified that error appears in the above-identified patent and that said Letters Patent is hereby corrected as shown below:

Column 45,
Line 4, in the title of Table 2, delete "C571B16" and insert -- C57B16 --, therefor.
Line 44, delete "TV" and insert -- TMX --, therefor.
Line 53, delete "TVX" and insert -- TMX --, therefor.

Column 46,
Line 26, delete "TmX" and insert -- TMX --, therefor.
Line 42, delete "C57B 16" and insert -- C57B16 --, therefor.
Line 59, delete "TV" and insert -- TMX --, therefor.

Column 47,
Line 54, delete "10ng/,L." and insert -- 10ng/$\mu$L. --, therefor.
Line 59, delete "GAATTCGTCAGGATrGCIGGTGTT" and insert -- GAATTCGTCAGGATTGCTGGTGTT --, therefor.

Column 48,
Line 8, delete "Ks$^+$" and insert -- KS$^+$ --, therefor.
Line 15, delete "a" after "ampicillin".
Line 22, delete "S" and insert -- 5 --, therefor.
Line 34, delete "(MBS;" and insert -- (TBS; --, therefor.
Line 51, insert -- - -- between "A" and "6154)".

Column 50,
Line 29, delete "%" after "TGF-β1".
Line 37, "To test the specificity…" should not be a new ¶.
Line 41, delete "i15".
Line 53, delete "150mmol/l" and insert -- 150mmol/L --, therefor.

UNITED STATES PATENT AND TRADEMARK OFFICE
CERTIFICATE OF CORRECTION

PATENT NO.     : 6,262,079 B1
DATED          : July 17, 2001
INVENTOR(S)    : David J. Grainger, James C. Metcalfe, Lawrence L. Kunz, Robert W. Schroff and Peter L. Weissberg It is certified that error appears in the above-identified patent and that said Letters Patent is hereby corrected as shown below:

Column 51,
Line 16, delete "-" between "in" and "TBS".
Line 24, delete "TGFT" and insert -- TGF-β --, therefor.
Line 28, delete "(n-3)" and insert -- (n=3) --, therefor.

Column 52,
Line 9, delete "1i" and insert -- 1β --, therefor.
Line 10, delete "a" and insert -- ∝ --, therefor.

Column 53,
Line 27, delete "ELJSAs" and insert -- ELISAs --,
Line 57, delete "TGF-," and insert -- TGF-β --, therefor.

Column 56,
Line 67, delete "60i24" and insert -- 60±24 --, therefor.

Column 57,
Line 4, delete "n-9)" and insert -- n=9) --,
Line 8, delete "(ac+1)" and insert -- (∝+1) --, therefor.
Line 32, delete "." between "quiescent" and "explant" and insert -- , --, therefor.

UNITED STATES PATENT AND TRADEMARK OFFICE
CERTIFICATE OF CORRECTION

PATENT NO. : 6,262,079 B1
DATED : July 17, 2001
INVENTOR(S) : David J. Grainger, James C. Metcalfe, Lawrence L. Kunz, Robert W. Schroff and Peter L. Weissberg It is certified that error appears in the above-identified patent and that said Letters Patent is hereby corrected as shown below:

Column 58,
Line 31, delete "-" between "origin" and "of".
Line 32, insert -- . -- after "plasma".
Line 40, delete "TGF-," and insert -- TGF-$\beta$ --, therefor.
Line 45, insert -- , -- after "specification".

Column 59,
Line 14, in claim No. 11, insert -- a -- between "is" and "kidney."

Signed and Sealed this

Eighteenth Day of June, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,262,079 B1
DATED : July 17, 2001
INVENTOR(S) : Grainger et al.

It is certified that error appears in the above-identified patent and that said Letters Patent is hereby corrected as shown below:

Title page,
Item [60], "Related U.S. Application Data," delete ", which is a continuation-in-part of application No. 08/011,669, filed on Jan. 28, 1993, now abandoned, which is a continuation-in-part of application No. PCT/US92/08220, filed on Sep. 25, 1992".

Column 1,
Lines 14-18, delete "which is a continuation-in-part of U.S. Ser. No. 08/011,669, filed Jan. 28, 1993, now abandoned, which is a continuation-in-part of PCT/US92/08220, filed Sep. 25, 1992,".

Signed and Sealed this

Tenth Day of September, 2002

Attest:

JAMES E. ROGAN
Attesting Officer  Director of the United States Patent and Trademark Office